(12) United States Patent
Hensley et al.

(10) Patent No.: US 9,796,931 B1
(45) Date of Patent: Oct. 24, 2017

(54) CATALYSTS AND METHODS FOR CONVERTING CARBONACEOUS MATERIALS TO FUELS

(71) Applicant: Alliance for Sustainable Energy, LLC, Golden, CO (US)

(72) Inventors: Jesse Hensley, Arvada, CO (US); Daniel A. Ruddy, Lafayette, CO (US); Joshua A. Schaidle, Arvada, CO (US); Mayank Behl, Lakewood, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 15/617,074

(22) Filed: Jun. 8, 2017

Related U.S. Application Data

(62) Division of application No. 14/731,673, filed on Jun. 5, 2015, now Pat. No. 9,714,387.

(Continued)

(51) Int. Cl.
*C10L 1/16* (2006.01)
*C10L 1/04* (2006.01)
(Continued)

(52) U.S. Cl.
CPC ............ *C10G 3/49* (2013.01); *B01J 29/7057* (2013.01); *B01J 29/7615* (2013.01); *C01B 3/02* (2013.01); *C01B 3/22* (2013.01); *C01B 3/34* (2013.01); *C07C 29/1518* (2013.01); *C07C 31/04* (2013.01); *C07C 41/01* (2013.01);
(Continued)

(58) Field of Classification Search
CPC .. C10G 3/49; C10G 3/50; C10G 50/00; C01B 3/34; C01B 3/22; C01B 3/02; C01B 2203/1241; C01B 2203/061; C01B 2203/06; C07C 41/01; C07C 29/1518;
(Continued)

(56) References Cited

U.S. PATENT DOCUMENTS

| 4,025,575 A | 5/1977 | Chang et al. |
| 4,708,786 A | 11/1987 | Occelli |

(Continued)

FOREIGN PATENT DOCUMENTS

| EP | 2 137 130 B1 | 4/2014 |
| WO | WO 2008/109877 A1 | 9/2008 |
| WO | WO 2013/032672 A1 | 3/2013 |

OTHER PUBLICATIONS

"The Dimerization of Triptene with Sulfuric Acid" by F C Whitmore W S Roopp and N C Cook (Apr. 1950) Whitmore Laboratory School of Chemistry and Physics of Pennsylvania State College vol. 72 pp. 1507-1511.*

(Continued)

*Primary Examiner* — Pamela H Weiss
(74) *Attorney, Agent, or Firm* — Michael A. McIntyre

(57) ABSTRACT

This disclosure relates to catalysts and processes designed to convert DME and/or methanol and hydrogen ($H_2$) to desirable liquid fuels. These catalysts produce the fuels efficiently and with a high selectivity and yield, and reduce the formation of aromatic hydrocarbons by incorporating $H_2$ into the products. This disclosure also describes process methods to further upgrade these fuels to higher molecular weight liquid fuel mixtures, which have physical properties comparable with current commercially used liquid fuels.

2 Claims, 42 Drawing Sheets

Related U.S. Application Data

(60) Provisional application No. 62/112,584, filed on Feb. 5, 2015, provisional application No. 62/057,754, filed on Sep. 30, 2014, provisional application No. 62/008,357, filed on Jun. 5, 2014.

(51) Int. Cl.

| | |
|---|---|
| *C10G 3/00* | (2006.01) |
| *C01B 3/22* | (2006.01) |
| *C10G 50/00* | (2006.01) |
| *C07C 41/01* | (2006.01) |
| *C07C 29/151* | (2006.01) |
| *C07C 31/04* | (2006.01) |
| *C07C 43/04* | (2006.01) |
| *C01B 3/02* | (2006.01) |
| *B01J 29/70* | (2006.01) |
| *B01J 29/76* | (2006.01) |
| *C01B 3/34* | (2006.01) |

(52) U.S. Cl.
CPC ............. *C07C 43/043* (2013.01); *C10G 3/50* (2013.01); *C10G 50/00* (2013.01); *C10L 1/04* (2013.01); *C01B 2203/02* (2013.01); *C01B 2203/025* (2013.01); *C01B 2203/0216* (2013.01); *C01B 2203/0222* (2013.01); *C01B 2203/0266* (2013.01); *C01B 2203/0283* (2013.01); *C01B 2203/06* (2013.01); *C01B 2203/061* (2013.01); *C01B 2203/1241* (2013.01); *C10J 2300/1665* (2013.01); *C10L 2200/0492* (2013.01); *C10L 2290/02* (2013.01); *C10L 2290/04* (2013.01); *C10L 2290/42* (2013.01); *Y02P 20/52* (2015.11); *Y02P 30/20* (2015.11)

(58) Field of Classification Search
CPC ..... B01J 29/7057; B01J 29/7615; C10L 1/04; Y02P 20/52
See application file for complete search history.

(56) References Cited

U.S. PATENT DOCUMENTS

| | | | |
|---|---|---|---|
| 4,912,281 | A | 3/1990 | Wu |
| 7,459,412 | B2 | 12/2008 | Lercher et al. |
| 7,825,287 | B2 | 11/2010 | Ahn et al. |
| 2009/0247803 | A1 | 10/2009 | Ahn et al. |
| 2009/0299109 | A1* | 12/2009 | Gruber ..................... C10L 1/04 585/14 |
| 2010/0025298 | A1 | 2/2010 | Hommeltoft et al. |
| 2010/0240938 | A1 | 9/2010 | Daniel et al. |
| 2010/0298616 | A1 | 11/2010 | Kettunen et al. |
| 2011/0136924 | A1 | 6/2011 | Fujimoto et al. |
| 2012/0088944 | A1 | 4/2012 | Buijs et al. |
| 2013/0324761 | A1 | 12/2013 | Hutchings et al. |
| 2015/0353840 | A1 | 12/2015 | Hensley et al. |

OTHER PUBLICATIONS

"Synthetic Middle Distillate Range Hydrocarbons via Catalytic Dimerization of Branched C6-C8 Olefins Derived from Renewable Dimethyl Ether" Energy & Fuels (2015), 29 pp. 6078-6087.*
Abbot et al., "Catalytic Cracking of Linear Paraffins: Effects of Chain Length", Industrial & Engineering Chemistry Research, Jan. 1997, vol. 36, No. 1, pp. 76-82.
Ahn, et al., "Selective Homologation Routes to 2,2,3-Trimethylbutane on Solid Acids", Angewandte Chemie International Edition, 2009, vol. 48, pp. 3814-3816.
Alonso et al., "Production of Liquid Hydrocarbon Transportation Fuels by Oligomerization of Biomass-derived $C_9$ Alkenes", Green Chemistry, 2010, vol. 12, pp. 992-999.
Bercaw et al., "Conversion of Methanol to 2,2,3-Trimethylbutane (Triptane) over Indium(III) Iodide", Inorganic Chemistry, 2007, vol. 46, No. 26, pp. 11371-11380.
Bermudez et al., "The structure of low-index surfaces of β-$Ga_2O_3$", Chemical Physics, Apr. 2006, vol. 323. Nos. 2-3, pp. 193-203.
Busca, "Acid Catalysts in Industrial Hydrocarbon Chemistry", Chemical Reviews, 2007, vol. 107, pp. 5366-5410.
Busco, et al., "Characterisation of Lewis and Brønsted Acidic Sites in H-MFI and H-BEA Zeolites: a Thermodynamic and Ab Initio Study", Thermochimica Acta, 2004, vol. 418, pp. 3-9.
Camblor et al., "Synthesis and Characterization of Gallosilicates and Galloaluminosilicates Isomorphous to Zeolite Beta", Zeolites, Mar. 1992, vol. 12, No. 3, pp. 280-286.
Chen et al., "Evidence of Autocatalysis in Methanol to Hydrocarbon Reactions Over Zeolite Catalysts", Journal of Catalysis, Aug. 1979, vol. 59, No. 1, pp. 123-129.
Cheung et al., "Site Requirements and Elementary Steps in Dimethyl Ether Carbonylation Catalyzed by Acidic Zeolites", Journal of Catalysis, 2007, vol. 245, No. 1, pp. 110-123.
Corma et al., "Characterization of Acid Surfaces by Adsorption of 2,6-9 dimethylpyridine", Journal of Catalysis, 1984, vol. 88, pp. 374-381.
Cruz et al., "Acid Ion-exchange Resins Catalysts for the Liquid-phase Dimerization / Etherification of Isoamylenes in Methanol or Ethanol Presence", Reactive and Functional Polymers, 2005, vol. 65, pp. 149-160.
Cruz et al., "Conversion, Selectivity and Kinetics of the Liquid-phase Dimerisation of Isoamylenes in the Presence of C1 to C5 Alcohols Catalysed by a Macroporous Ion-Exchange Resin", Journal of Catalysis, 2006, vol. 238, pp. 330-341.
Dutta et al., "Process Design and Economics for Conversion of Lignocellulosic Biomass to Ethanol", NREL Technical Report, NREL/TP-5100-51400, May 2011, pp. 1-187.
Gee et al., "Dimerization of Linear Olefins on Amberlyst® 15: Effects of Chain Length and Double-bond Position", Journal of Catalysis, Jul. 2013, vol. 303, pp. 1-8.
Harmer et al., "Solid Acid Catalysis Using Ion-Exchange Resins", Applied Catalysis A: General, 2001, vol. 221, Nos. 1-2, pp. 45-62.
Hauge et al., "Oligomerization of Isobutene Over Solid Acid Catalysts", Catalysis Today, 2005, vol. 100, Nos. 3-4, pp. 463-466, Aug. 15, 2017.
Hazari et al., "Selective Homogeneous and Heterogeneous Catalytic Conversion of Methanol/Dimethyl Ether to Triptane", Accounts of Chemical Research, Jan. 25, 2012, vol. 45, No. 4, pp. 653-662.
Honkela et al., "Comparison of Ion-Exchange Resin Catalysts in the Dimerisation of Isobutene", Applied Catalysis A: General, 2005, vol. 295, pp. 216-223.
Ilias et al., "Mechanism of the Catalytic Conversion of Methanol to Hydrocarbons", ACS Catalysis, 2013, vol. 3, No. 1, pp. 18-3.
Jacobs et al., "Will Zeolite-Based Catalysis be as Relevant in Future Biorefineries as in Crude Oil Refineries?", Angewandte Chemie International Edition, Jul. 2014, vol. 53, No. 33, pp. 8621-8626.
Jae et al., "Investigation into the Shape Selectivity of Zeolite Catalysts for Biomass Conversion", Journal of Catalysis, 2011, vol. 279, pp. 257-268.
Kazansky, "The Nature of Adsorbed Carbenium Ions as Active Intermediates in Catalysis by Solid Acids", Accounts of Chemical Research, 1991, vol. 24, pp. 379-383.
Langner et al., "Reactions of Methanol on Zeolites with Different Pore Structures", Applied Catalysis, Apr. 1982, vol. 2, Nos. 4-5, pp. 289-302.
Li et al., "Hierarchical SAPO-34/18 Zeolite with Low Acid Site Density for Converting Methanol to Olefins", Catalysis Today, 2014, vol. 233, pp. 2-7.
Lilja et al., "The Selective Sorption of Solvents on Sulphonic Acid Polymer Catalyst in Binary Mixtures", Reactive & Functional Polymers, Aug. 2005, vol. 64, No. 2, pp. 111-118.
Meitzner et al., "The Chemical State of Gallium in Working Alkane Dehydrocyclodimerization Catalysts. In situ Gallium K-Edge X-Ray Absorption Spectroscopy", Journal of Catalysis, Mar. 1993, vol. 140, No. 1, pp. 209-225.

(56) References Cited

OTHER PUBLICATIONS

Mendes et al., "Determination of Octane Numbers in Gasoline by Distillation Curves and Partial Least Squares Regression", Fuel, Jul. 2012, vol. 97, pp. 131-136.
Mokrani et al. "Gas Conversion to Liquid Fuels and Chemicals: The Methanol Route-Catalysis and Processes Development", Catalysis Reviews: Science and Engineering, 2009, vol. 51, No. 1, pp. 1-145.
Morterra et al., "Revisiting the Use of 2,6-Dimethylpyridine Adsorption as a Probe for the Acidic Properties of Metal Oxides", Langmuir, 2001, vol. 17, pp. 7053-7060.
Olsbye et al., "Conversion of Methanol to Hydrocarbons: How Zeolite Cavity and Pore Size Controls Product Selectivity", Angewandte Chemie International Edition, Jun. 2012, vol. 51, No. 24, pp. 5810-5831.
Pereira et al., "Effect of the Zeolite Cavity on the Mechanism of Dehydrogenation of Light Alkanes over Gallium-Containing Zeolites", The Journal of Physical Chemistry C, Apr. 2011, vol. 115 pp. 10104-10113.
Phillips et al., "Gasoline from Wood via Integrated Gasification, Synthesis, and Methanol-to Gasoline Technologies", National Renewable Energy Laboratory Technical Report NREL/TP-5100-47594, Jan. 2011, pp. 1-102.
Pietrzyk, "Ion-exchange Resins in Non-aqueous Solvents-III: Solvent-uptake Properties of Ion-exchange Resins and Related Absorbents", Talanta, Feb. 1969, vol. 16, pp. 169-179.
Rajagopal et al., "Nafion® SAC-13: Heterogeneous and Reusable Catalyst for the Activation of HMDS for Efficient and Selective O-silylation reactions under solvent-free Condition", Tetrahedron, 2009, vol. 65, pp. 4735-4741.
Russo et al., "Mesoporous Carbon-silica Solid Acid Catalysts for Producing Useful Bio-products Within the Sugar-platform of Biorefineries", Green Chemistry, Jul. 2014, vol. 16, pp. 4292-4305.
Russo et al., "Solid Acids with SO3H Groups and Tunable Surface Properties: Versatile Catalysts for Biomass Conversion", Journal of Materials Chemistry A, 2014, vol. 2, pp. 11813-11824.
Ryzhikov et al., "Reactive Adsorption of Thiophene on Ni/ZnO: Role of Hydrogen Pretreatment and Nature of the Rate Determining Step", Applied Catalysis B: Environmental, 2008, vol. 84, pp. 766-772.
Saravanamurugan et al., "Solid Acid Catalysed Formation of Ethyl Levulinate and Ethyl Glucopyranoside from Mono- and Disaccharides", Catalysis Communications, 2012, vol. 17, pp. 71-75.
Shah et al., "Dimerization of Isoamylene: Ion Exchange Resin and Acid-treated Clay as Catalysts", Reactive Polymers, 1993, vol. 19, No. 3, pp. 181-190.
Shibata et al., "Acid Property and Catalytic Activity of Silica Gel Treated with Ammonium Salts", Journal of the Research Institute for Catalysis, Hokkaido University, 1971, vol. 19, No. 1, pp. 29-34.
Simonetti et al., "Acid strength and Solvation Effects on Methylation, Hydride Transfer, and Isomerization Rates During Catalytic Homologation of C1 Species", Journal of Catalysis, 2012, vol. 285, No. 1, pp. 19-30.
Simonetti et al., "Catalytic Co-Homologation of Alkanes and Dimethyl Ether and Promotion by Adamantane as a Hydride Transfer Co-Catalyst", ChemCatChem, Apr. 11, 2011, vol. 3, No. 4, pp. 704-718.
Simonetti et al., "Mechanistic Details of Acid-catalyzed Reactions and Their Role in the Selective Synthesis of Triptane and Isobutane from Dimethyl Ether", Journal of Catalysts, 2011, vol. 277, pp. 173-195.
Srimani et al., "Direct Catalytic Olefination of Alcohols with Sulfones", Angewandte Chemie International Edition, Oct. 2014, vol. 53, No. 41, pp. 11092-11095.
Sun et al., "A Review of the Different Techniques for Solid Surface Acid-base Characterization", Advances in Colloid and Interface Science, Sep. 18, 2003, vol. 105, Nos. 1-3, pp. 151-175.
Sun et al., "On Reaction Pathways in the Conversion of Methanol to Hydrocarbons on HZSM-5", Journal of Catalysis, 2014, vol. 317, pp. 185-197.
Tzvetkova et al., "Modified and Unmodified Silica Gel Used for Heavy Metal Ions Removal from Aqueous Solutions", Journal of the University of Chemical Technology and Metallurgy, 2012, vol. 45, No. 5, pp. 498-504.
Weingarten et al., "Design of Solid Acid Catalysts for Aqueous-phase Dehydration of Carbohydrates: The Role of Lewis and Brønsted Acid Sites", Journal of Catalysis, Apr. 2011, vol. 279, No. 1, pp. 174-182.
Whitmore et al., "The Dimerization of Triptene with Sulfuric Acid", Contribution from The Whitmore Laboratory of the School of Chemistry and Physics of the Pennsylvania State College, Apr. 1950, vol. 72, pp. 1507-1511.

\* cited by examiner

A.

B.

CATALYSTS AND METHODS FOR CONVERTING CARBONACEOUS MATERIALS TO FUELS

CROSS-REFERENCE TO RELATED APPLICATIONS

This application is a divisional of U.S. Non-Provisional patent application Ser. No. 14/731,673, which claims priority to, and the benefit of, U.S. Provisional Patent Application Nos. 62/008,357, 62/057,754, 62/112,584 filed on Jun. 5, 2014, Sep. 30, 2014, and Feb. 5, 2015 respectively, which are all incorporated herein by reference in their entireties.

CONTRACTUAL ORIGIN

The United States Government has rights in this invention under Contract No. DE-AC36-08GO28308 between the United States Department of Energy and the Alliance for Sustainable Energy, LLC, the Manager and Operator of the National Renewable Energy Laboratory.

BACKGROUND

The conversion of dimethyl ether (DME) and/or methanol to hydrocarbons may provide a route to transportation fuels from $C_1$ intermediates produced from synthesis gas (syngas) derived from diverse resources such as natural gas, coal, or biomass. The production of a mixture of linear and branched hydrocarbons from DME has been recently demonstrated at relatively low temperatures and pressures over large-pore acidic zeolites. This process provides high selectivity to branched $C_4$-$C_8$ paraffins and olefins. The gasoline-range product stream holds further potential for use as transportation fuel via coupling to distillate-range hydrocarbons. However, due to the hydrogen deficiency of DME homologation to $C_4$-$C_8$ paraffin and olefin products, unsaturated products are also formed, including alkylated aromatics such as hexamethylbenzene (HMB), which decrease the yield of the desired branched $C_4$-$C_8$ products, and may result in catalyst deactivation. Thus, there remains a need for improved catalysts and processes for the conversion of DME and/or methanol to liquid fuels. Specifically, the development of a catalyst and process that can incorporate hydrogen into the product, via activation of molecular $H_2$, with only minimal effect on the high selectivity to $C_4$-$C_8$ hydrocarbons represents a significant improvement to the original process. Further, the development of a catalyst and process to convert the gasoline-range product to a distillate-range product is required to broaden the pathway from DME and/or methanol to multiple transportation fuels.

SUMMARY

An aspect of the present invention is a catalyst including an aluminosilicate crystal structure and a first active metal deposited on a surface of the crystal structure. The catalyst has a content of total acid sites ranging from about 1000 µmol/g to about 2500 µmol/g and a ratio of Brønsted acid sites to Lewis acid sites ranging from about 0.1 to about 30.

In some embodiments of the present invention the catalyst may have a content of total acid sites ranging from about 1900 µmol/g to about 2100 µmol/g. In some embodiments, the catalyst may have a ratio of Brønsted acid sites to Lewis acid sites ranging from about 0.5 to about 2.5. In further embodiments, the crystal structure may include a zeolite with a 10-membered ring or larger pore. In further embodiments, the crystal structure may include a zeolite with a 12-membered ring pore. In still further embodiments, the zeolite may have a silicon to aluminum ratio ranging from about 100:1 to about 5:1. In yet further embodiments, the silicon to aluminum ratio may range from about 10:1 to about 5:1. In some embodiments, the aluminosilicate includes a hydrogen form of a beta-type zeolite.

In some embodiments of the present invention, the first active metal of the catalyst may include at least one of copper, zinc, iron, gallium, lanthanum, and/or platinum. In some embodiments, the first active metal may be present at a weight percent ranging from about 0.1% to about 10%. In further embodiments, the catalyst may have a second active metal incorporated into the crystal structure of the catalyst. In yet further embodiments, the second active metal may include at least one of copper, zinc, iron, gallium, lanthanum, and/or platinum.

A further aspect of the present invention is a catalyst that includes a beta-type zeolite and a first active metal deposited on the zeolite. The zeolite has an acid content ranging from about 1900 µmol/g to about 2100 µmol/g and a ratio of Brønsted acid sites to Lewis acid sites ranging from about 0.5 to 2.5, and the first active metal includes at least one of copper, zinc, iron, gallium, lanthanum, and/or platinum. In some embodiments of the present invention, the catalyst may include a second active metal of gallium incorporated into the zeolite.

A further aspect of the present invention is a method for producing liquid fuels, where the method includes converting a carbonaceous material to a mixture that includes syngas, converting at least a portion of the syngas to at least one of dimethyl ether or methanol, and contacting the at least one of the dimethyl ether and/or methanol and a hydrogen stream with a catalyst. The contacting of the at least one of the dimethyl ether or methanol and a hydrogen stream with a solid catalyst produces a first product mixture that includes $C_4$+ olefins and paraffins. The catalyst includes a beta-type zeolite and at least one metal of copper, zinc, iron, gallium, lanthanum, and/or platinum, and the zeolite has an acid content ranging from about 1900 µmol/g to about 2100 µmol/g, and a ratio of Brønsted acid sites to Lewis acid sites ranging from about 0.5 to about 2.5, and the metal is deposited on a surface of the zeolite.

In some embodiments of the present invention, the first product mixture includes at least one of 2,2,3-trimethylbutane (triptane) or 2,3,3-trimethyl-1-butene (triptene). In some embodiments of the present invention, the method also includes contacting at least a portion of the first product mixture with an acid catalyst, such that the contacting couples a first fraction of the first product mixture with a second fraction of the product mixture to produce a higher molecular weight second product mixture. In some embodiments, the second product mixture includes 2,2,3,5,5,6,6-heptamethyl-3-heptene, 2,2,4,6,6-pentamethyl-3-heptene, 2,2,3,5,6-pentamethyl-3-heptene, 2,3,5,5,6-pentamethyl-3-heptene, 2,2-dimethyl-3-octene, and/or 2,2,4,6,6,8,8-heptamethyl-4-nonene. In still further embodiments of the present invention, the carbonaceous material includes at least one of biomass, natural gas, process tail gas, coal, or oil.

A further aspect of the present invention is a liquid fuel that includes a fuel having a density ranging from about 0.7 g/cm³ to about 0.85 g/cm³, a boiling point ranging from about 180° C. to about 400° C., a heat of combustion ranging from about 40 MJ/kg to about 50 MJ/kg, and a cloud point of less than −50° C. In some embodiments of the present invention, the fuel may include 2,2,3,5,5,6,6-heptamethyl-3-heptene.

BRIEF DESCRIPTION OF DRAWINGS

Exemplary embodiments are illustrated in referenced figures of the drawings. It is intended that the embodiments and figures disclosed herein are to be considered illustrative rather than limiting.

REFERENCE NUMBERS

Figure 1:
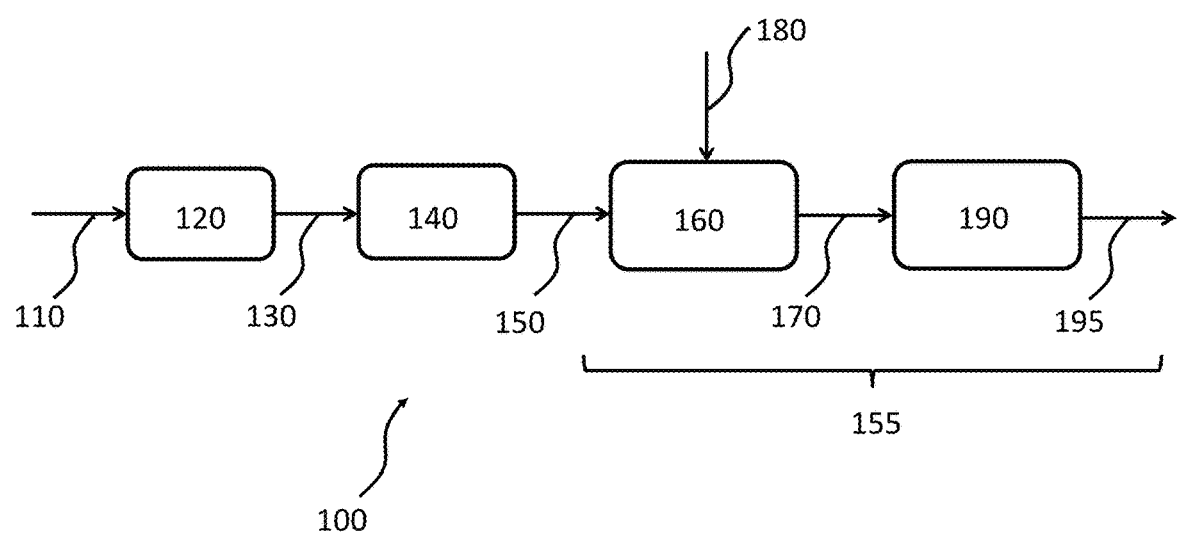
FIG. 1 illustrates a process for converting carbonaceous materials to liquid fuels, according to exemplary embodiments of the present invention.

100 . . . fuel refinery
110 . . . carbonaceous feedstock
120 . . . syngas production process
130 . . . syngas
140 . . . DME and/or methanol production process
150 . . . DME and/or methanol stream
155 . . . liquid fuel production plant
160 . . . $C_1$-$C_9$ linear and branched olefin and paraffin production process
170 . . . $C_4$-$C_9$ linear and branched olefin and paraffin fuel stream
180 . . . hydrogen ($H_2$)
190 . . . $C_4$-$C_9$ linear and branched olefin and paraffin coupling process
195 . . . gasoline and distillate-range hydrocarbon fuel
200 . . . methanol storage
210 . . . $H_2$ production plant
220 . . . $C_1$-$C_9$ linear and branched olefin and paraffin production reactor
230 . . . crude reaction product stream
240 . . . effluent flash vessel
250 . . . first $C_1$ and $C_2$ stream
260 . . . first $C_2$+ stream
270 . . . first distillation column
275 . . . second $C_1$ and $C_2$ stream
280 . . . $C_3$+ stream
285 . . . second distillation column
290 . . . $C_3$ and $C_4$ stream
297 . . . third distillation column
298 . . . $C_4$ stream
299 . . . $C_3$ and $C_4$ stream
300 . . . zeolite
310 . . . framework
320 . . . pore
330 . . . first active metal site
340 . . . second active metal site

DETAILED DESCRIPTION OF EXEMPLARY EMBODIMENTS

FIG. 1 illustrates a fuel refinery 100 for converting carbonaceous feedstock 110 to liquid fuels. Examples of carbonaceous feedstock 110 include biomass, municipal solid waste, natural gas, process tail gas, coal, and/or oil. Examples of biomass include wood, bagasse, corn stover, wheat straw, municipal yard waste, and any other suitable agricultural and/or municipal waste. The carbonaceous feedstock 110 may be converted to syngas 130 in a syngas production plant 120, for example by pyrolysis, gasification, steam reforming, dry reforming, and/or partial oxidation. The syngas 130 may then be fed to a methanol and/or dimethyl ether (DME) production process 140 to convert at least a portion of the syngas 130 to methanol and/or DME 150. The methanol and/or DME 150 produced may be subsequently fed to a first step, a $C_1$-$C_9$ linear and branched olefin and paraffin production process 160, of a liquid fuel production plant 155 where the methanol and/or DME 150 may be reacted using a solid catalyst (not shown) to produce a $C_4$-$C_9$ linear and branched olefin and paraffin fuel stream 170. In some cases, the $C_1$-$C_9$ linear and branched olefin and paraffin production process 160 may react hydrogen ($H_2$) 180 with the methanol and/or DME 150 to produce the $C_4$-$C_9$ linear and branched olefin and paraffin fuel stream 170. The $C_4$-$C_9$ linear and branched olefin and paraffin fuel stream 170 may be further processed in a second step of the liquid fuel production plant 155, a coupling process 190, to yield a higher molecular weight liquid fuel product, referred to herein as a gasoline and distillate-range hydrocarbon fuel 195. The term gasoline range refers to a mixture containing linear and branched $C_4$-$C_8$ paraffins and olefins. The term distillate-range refers to a mixture containing linear and branched $C_8$-$C_{22}$ (and larger) paraffins and olefins. The gasoline and distillate-range hydrocarbon fuel 195 may be produced, for example, by coupling reactions of at least one or more of the components contained in the $C_4$-$C_9$ linear and branched olefin and paraffin fuel stream 170. In some cases, all of the processing steps shown in FIG. 1 may occur in series at a single processing site. In other cases, intermediate components, for example syngas 130, DME and/or methanol 150, and/or the $C_4$-$C_9$ linear and branched olefin and paraffin fuel stream 170, may be produced at one or more separate locations and transported to other intermediate and/or final processing steps.

Figure 2:
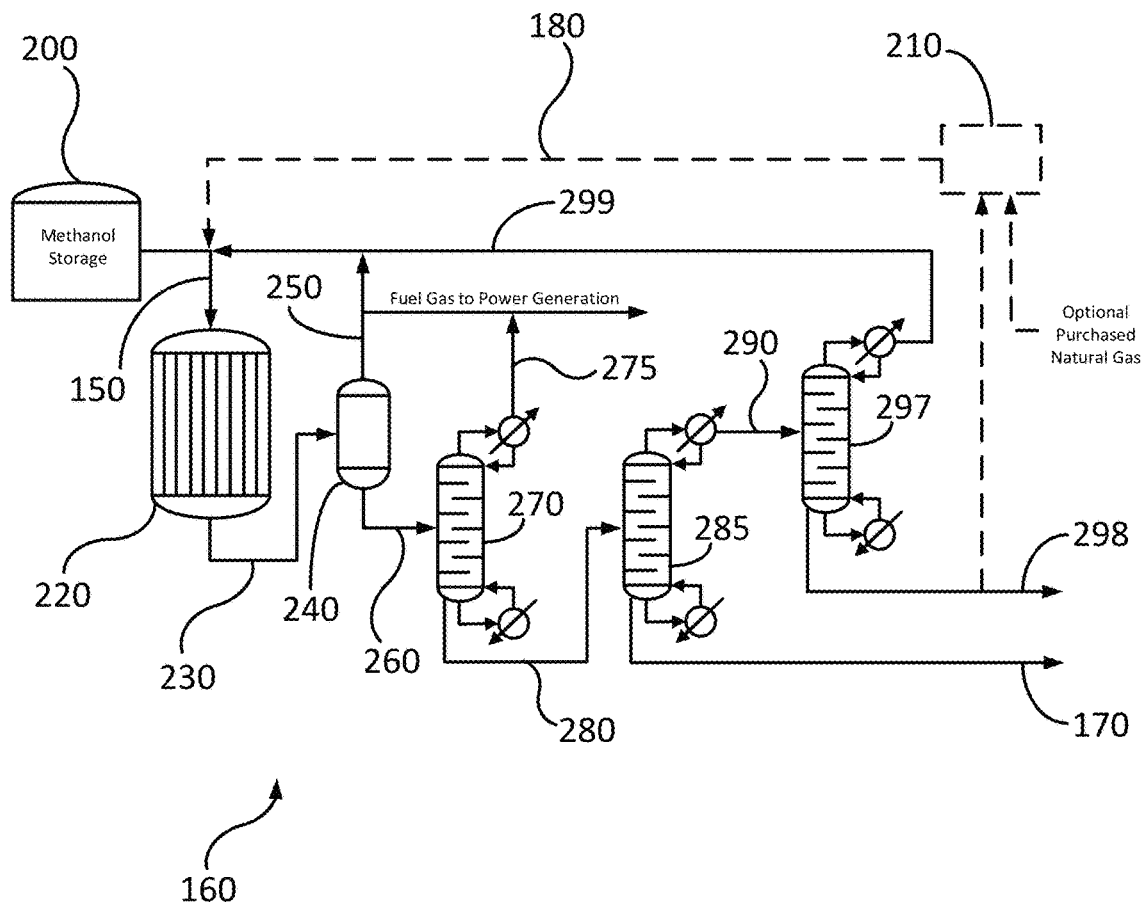
FIG. 2 illustrates a process for converting DME and/or methanol and $H_2$ to liquid fuels, according to exemplary embodiments of the present invention.

FIG. 2 illustrates additional features of an exemplary $C_1$-$C_9$ linear and branched olefin and paraffin production process 160. A $C_1$-$C_9$ linear and branched olefin and paraffin production process 160 for converting DME and/or methanol and $H_2$ to liquid fuels may include a methanol storage tank 200 and/or a DME storage tank (not shown) for receiving these reactants from a methanol and/or DME production process 140 (not shown). In addition, a $C_1$-$C_9$ linear and branched olefin and paraffin production process 160 may also include a hydrogen ($H_2$) production plant 210 for providing $H_2$ 180 to at least one $C_1$-$C_9$ linear and branched olefin and paraffin production reactor 220. FIG. 2 illustrates that the reactant streams may be mixed before feeding to one or more $C_1$-$C_9$ linear and branched olefin and paraffin production reactor(s) 220, which may contain a solid catalyst for converting the methanol and/or DME and $H_2$ into a crude reaction product stream 230, for example, a $C_1$-$C_9$ linear and branched olefin and paraffin containing stream. Alternatively, the individual reactants, for example the DME and methanol, may be individually fed to the $C_1$-$C_9$ linear and branched olefin and paraffin production reactor 220 and mixed within the reactor. The reactants may be fed to the $C_1$-$C_9$ linear and branched olefin and paraffin production reactor 220 in a top-down configuration or, alternatively, in a bottom-up configuration. In some examples, the $C_1$-$C_9$ linear and branched olefin and paraffin production reactor 220 may be operated at sufficient pressure such that the crude reaction products stream 230 may be substantially in the liquid phase.

The crude reaction products stream 230 may then be fed to an effluent flash tank 240, which may operate at a pressure substantially lower than the operating pressure of the $C_1$-$C_9$ linear and branched olefin and paraffin production reactor 220. In some cases, the effluent flash tank 240 may operate at a pressure that is from about 0.1 atm to about 0.5 atm lower than the $C_1$-$C_9$ linear and branched olefin and paraffin production reactor 220. As a result of this lower pressure, low molecular weight $C_1$ and $C_2$ components may be removed as a gas phase in a first $C_1$ and $C_2$ stream 250, which may either be recycled to the $C_1$-$C_9$ linear and branched olefin and paraffin production reactor 220 and/or removed as fuel gas for power generation or $H_2$ production. The non-flashed, higher molecular weight components, e.g. $C_2$+ components, may then be fed as a first $C_2$+ stream 260 to a first distillation column 270. The first distillation column 270 may split the first $C_2$+ stream 260 into a second $C_1$ and $C_2$ stream 275 and a $C_3$+ stream 280. The second $C_1$ and $C_2$ stream 275 may be removed from the $C_1$-$C_9$ linear and branched olefin and paraffin production process 160 as fuel gas for power generation or $H_2$ production. The $C_3$+ stream 280 may be fed to a second distillation column 285, which may separate $C_3$ and $C_4$ components from $C_4$+ components, in a $C_3$ and $C_4$ stream 290 and a $C_4$-$C_9$ linear and branched olefin and paraffin fuel stream 170 respectively. The $C_3$ and $C_4$ stream 290 may then be fed to a third distillation column 297, which may separate the $C_3$ and $C_4$ stream 290 into a $C_4$ stream 298 (bottoms) and a $C_3$-$C_4$ stream 299 (overheads). The $C_3$-$C_4$ stream 299 may then be recycled to the $C_1$-$C_9$ linear and branched olefin and paraffin production reactor 220 and the $C_4$ stream 298 removed from the $C_1$-$C_9$ linear and branched olefin and paraffin production process 160 for use elsewhere. The $C_4$-$C_9$ linear and branched olefin and paraffin fuel stream 295 may be subsequently fed to a downstream coupling process 190 (see FIG. 1) for conversion to higher molecular weight gasoline and distillate-range hydrocarbon fuels 195, as shown in FIG. 1 and described below in more detail.

Figure 3A:
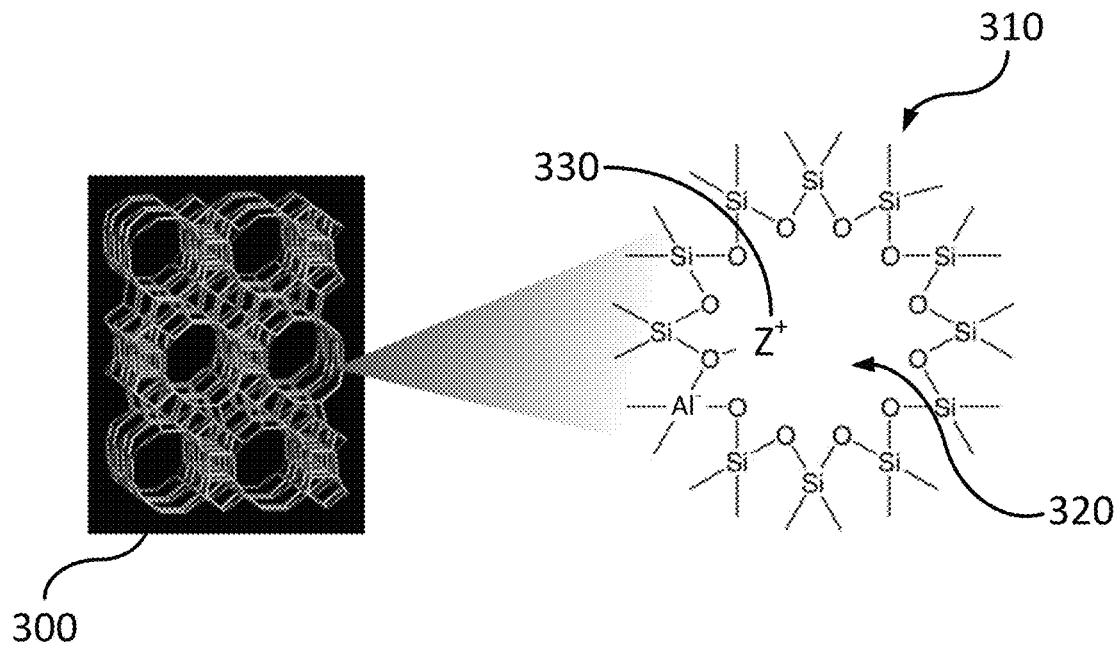
FIGS. 3a and 3b illustrate solid catalysts for converting DME and/or methanol and $H_2$ to liquid fuels, according to exemplary embodiments of the present invention.
Figure 3B:
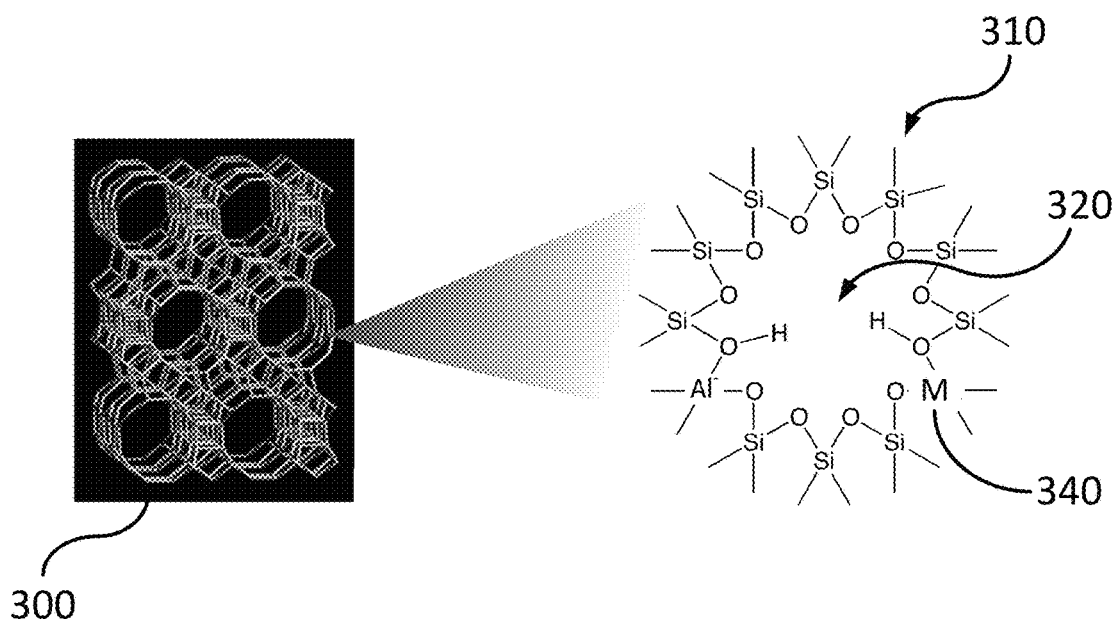

In some cases, the $C_1$-$C_9$ linear and branched olefin and paraffin production reactor 220 of the liquid fuel production plant 155 may include a solid catalyst to convert DME and/or methanol and $H_2$ to a $C_1$-$C_9$ linear and branched olefin and paraffin fuel stream 230. Such a solid catalyst may include a zeolite 300 as shown in FIGS. 3a and 3b. The zeolite may be a framework 310 of silicon and/or aluminum atoms with each silicon and/or aluminum atom covalently bound to four oxygen atoms. The framework 310 of silicon and oxygen atoms in the zeolite 300 may form a substantially circular and/or tubular-shaped pore 320 and corresponding surfaces upon which catalysis can occur. FIGS. 3a and 3b also illustrate that a zeolite's pore 320 may be outlined by a ring of repeating silicon and oxygen atoms (and/or aluminum and oxygen atoms). The number of pairs is often referred to as the ring number. For example, the zeolites in FIGS. 3a and 3b are characterized by a 12-membered ring pore. In addition, the zeolite framework 310 may contain aluminum atoms that have replaced some of the silicon atoms. The aluminum atoms may provide a negative charge imbalance that may be balanced by a positively charged atom and/or species, represented as $Z^+$ in FIG. 3a. Examples include protons ($H^+$) hydronium ions ($H_3O^+$), ammonium ions ($NH_4^+$), and positively charged metal atoms ($M^+$). Thus, in some cases, the $C_1$-$C_9$ linear and branched olefin and paraffin production reactor 220 may include a zeolite solid catalyst in which the $H^+$ and/or $NH_4^+$ cations of a starting zeolite have been replaced (or exchanged) with a first active metal component, $M^+$. Examples of $M^+$ include copper, zinc, iron, lanthanum, gallium, and platinum. Note that $M^+$ may include one or more positive charges; e.g. n+.

Referring now to FIG. 3b, a zeolite 300 may also be modified by exchanging an aluminum framework 310 atom with a second active metal component, shown in FIG. 3b, as M. Thus, by carefully choosing the zeolite and silicon to aluminum ratio, and by careful selection of the first active metal and/or the second active metal, and with subsequent oxidation and/or reduction steps, zeolite catalysts have been synthesized that effectively convert DME and/or methanol and $H_2$ to $C_4$-$C_9$ linear and branched olefin and paraffin-containing liquid fuels.

Figure 4A:
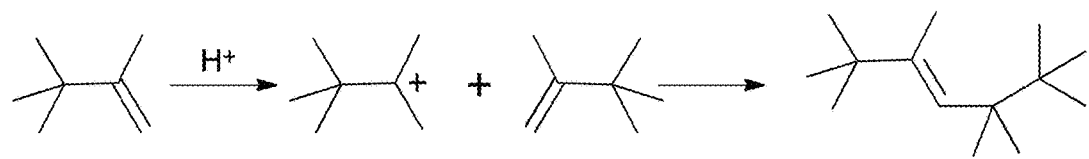
FIGS. 4a and 4b illustrate a second reaction for producing liquid fuels, according to exemplary embodiments of the present invention.

In addition, referring again to FIG. 1, a $C_4$-$C_9$ linear and branched olefin and paraffin fuel stream 170 may be converted to a second fuel, a gasoline and distillate-range hydrocarbon fuel 195, in a coupling process 190. The resultant higher molecular weight liquid fuels, the gasoline and distillate-range hydrocarbon fuel 195, may closely approximate the physical properties and performance metrics of some commonly utilized liquid fuels, for example diesel and jet fuel. For example, FIG. 4a illustrates an acid-catalyzed coupling reaction of two 2,3,3-trimethyl-1-butene (triptene) molecules to form a 2,2,3,5,5,6,6-heptamethyl-3-heptene (di-triptene). In some examples, a coupling reaction of one or more olefins to at least one coupled product may be accompanied by at least one of an isomerization reaction, an additional coupling reaction (oligomerization) and/or a cracking reaction. The conversion of a $C_4$-$C_9$ linear and branched olefin and paraffin fuel stream 170 to a gasoline and distillate-range hydrocarbon fuel 195 may be carried out, for example, by passing the $C_4$-$C_9$ linear and branched olefin and paraffin fuel stream 170, in liquid form, over a solid catalyst. Examples of such a solid catalyst include acid catalysts such as acid functionalized ion exchange resins.

Figure 4B:
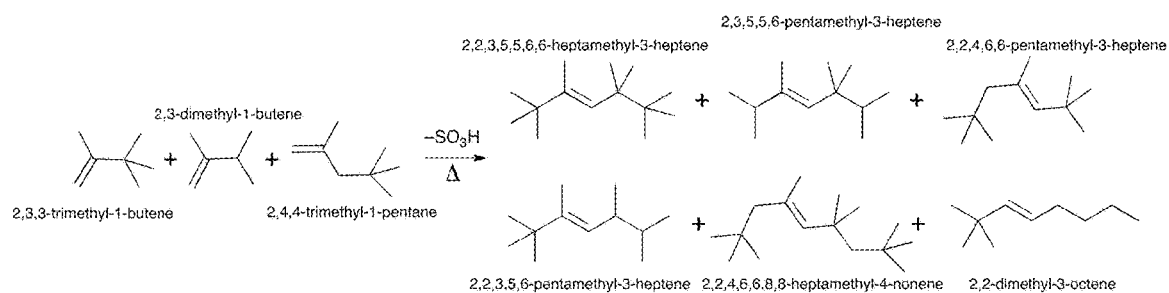

However, the reactions occurring in the coupling process 190 may involve a mixture of components entering with the $C_4$-$C_9$ linear and branched olefin and paraffin fuel stream 170 and, as a result, may involve a mixture of components leaving in the gasoline and distillate-range hydrocarbon fuel 195. A further example, illustrating potential components that may be involved in reactions for converting the $C_4$-$C_9$ linear and branched olefin and paraffin fuel stream 170 to a gasoline and distillate-range hydrocarbon fuel stream 195 is shown in FIG. 4b. In this case, a $C_4$-$C_9$ linear and branched olefin and paraffin fuel stream 170 may include 2,3,3-trimethyl-1-butene (triptene), 2,3-dimethyl-1-butene, and/or 2,4,4-trimethyl-1-pentene, among other olefins. The gasoline and distillate-range hydrocarbon fuel stream 195 resulting from coupling reactions occurring with the coupling process 190 may then include 2,2,3,5,5,6,6-heptamethyl-3-heptene (di-triptene), 2,2,4,6,6-pentamethyl-3-heptene, 2,2,3,5,6-pentamethyl-3-heptene, 2,3,5,5,6-pentamethyl-3-heptene, 2,2-dimethyl-3-octene, and/or 2,2,4,6,6,8,8-heptamethyl-4-nonene, among other coupled products.

Conversion of DME and/or Methanol to $C_4$-$C_9$ Linear and Branched Olefins and Paraffins In some embodiments of the present invention, a solid catalyst for the conversion of DME and/or methanol and $H_2$ to a $C_1$-$C_9$ linear and branched olefins and paraffins may include an aluminosilicate. As used herein, "aluminosilicate" refers to materials containing aluminum, silicon, and oxygen. Examples of aluminosilicates include clay minerals and zeolites. Examples of clay minerals include kaolin, smictite, illite, chlorite, sepiolite, and attapulgite. A zeolite is a microporous crystalline aluminosilicate, composed of $TO_4$ tetrahedra, wherein T is a silicon or aluminum atom, with oxygen atoms connecting neighboring tetrahedral. The extra-framework cations in zeolites and molecular sieves are ion exchangeable. The amount of aluminum within the framework can vary over a wide range, with silicon to aluminum ratios varying from 1 to 1 to infinity to 1 for the case where the zeolite contains no aluminum, the completely siliceous form of $SiO_2$.

As the amount of trivalent aluminum is increased in a zeolite's framework, the zeolite's physical properties may change. In some examples, Brønsted acid sites may catalyze the reaction of DME and/or methanol and $H_2$ to produce a $C_1$-$C_9$ linear and branched olefin and paraffin stream. These protons are labile as evidenced by their ability to be ion-exchanged with with other cations such as ammonium ($|(NH_4^+)_3|$ $[Al_3Si_{33}O_{72}]$—CHA) or sodium ($|Na^+|_3$ $[Al_3Si_{33}O_{72}]$—CHA). In addition, zeolites may have several water molecules coordinated to their cations to form hydrated zeolites.

Thus, cations may be placed (or deposited) onto the surfaces and/or within the pores of a zeolite and/or a molecular sieve. Examples of such ion-exchangeable cations that may be deposited onto a zeolite crystalline surface include monovalent cations such as $H^+$, $Li^+$, $K^+$, $Rb^+$, $Cs^+$, $Ag^+$, and $Tl^+$, divalent cations such as $Cd^{2+}$, $Ca^{2+}$, $Sr^{2+}$, $Cu^{2+}$, $Pt^{2+}$, and $Ba^{2+}$, rare earth ions such as $La^{3+}$, transition metal ions such as Cr, Mo, W, Mn, Fe, Ni, Cu, Zn, Ag, Al, and Ga, having a variety of valence charges, noble metals such as Pt and Pd in the form of $Pt(NH_3)_4^{2+}$ and $Pd(NH_3)_4^{2+}$ respectively, inorganic ions such as ammonium ($NH_4^+$), tetramethylammonium ion (TMA), tetraethylammonium ion (TEA), tetrapropylammonium (TPA), benzyltrimethylammonium (BTMA), and $C_1$-$C_4$ mono-n-alkylammonium, and/or di-n-alkylammonium (MA, EA, PA, BA, M2A, E2A, P2A, B2A) ions. These various elements and/or compounds may serve as active sites that may catalyze the reaction of DME and/or methanol and $H_2$ to produce a $C_1$-$C_9$ linear and branched olefin and paraffin stream. In some cases, a metal active site may function as a "hydrogenation" catalyst, to aid in the $H_2$ addition to unsaturated hydrocarbons As used herein, the term "molecular sieves" refers to crystalline aluminosilicate materials (e.g. zeolites) that incorporate other elements instead of or in addition to silicon and aluminum. For example, aluminophosphates (AlPOs) have strictly alternating $AlO_2^-$ and $PO_2^+$ units, and the framework is neutral, organophilic, and nonacidic. The alternation of aluminum or phosphorus leads to structures lacking in odd-numbered rings. Substitution of phosphorus by silicon leads to silicoaluminophosphates (SAPOs), with cation-exchange abilities. Thus, some examples of catalysts for converting DME and/or methanol and $H_2$ to a $C_1$-$C_9$ linear and branched olefin and paraffin stream may include molecular sieves. Some molecular sieves may also include one or more elements and/or compounds as catalytic active sites, as described above for zeolites.

Zeolites and molecular sieves may be characterized as small, medium, or large pore types. Non-limiting examples of these zeolites/molecular sieves include the small pore zeolites/molecular sieves, AEI, AFT, APC, ATN, ATT, ATV, AWW, BIK, CAS, CHA, CHI, DAC, DDR, ED1, ER1, GOO, KFI, LEV, LOV, LTA, MON, PAU, PHI, RHO, ROG, THO, and substituted forms thereof; the medium pore zeolites/molecular sieves, AFO, AEL, EUO, HEU, FER, MEL, MFI, MTW, MTT, TON, and substituted forms thereof; and the large pore zeolites/molecular sieves, including BEA, EMT, FAU, and substituted forms thereof. Other zeolites/molecular sieves include ANA, CFI, CLO, DON, GIS, LTL, MER, MOR, MWW, SOD, faujasites, pentasils, mordenite, beta, VPI, MCM, SAPO, MeAPO, ELAPO, and ELAPSO, zeolite X, zeolite Y, VPI-5, MCM-41, ZSM-5, ZSM-11, ZSM-14, ZSM-17, ZSM-18, ZSM-20, ZSM-31, ZSM-34, ZSM-41 and ZSM-46. In some examples, a BEA zeolite and/or another large pore zeolite and/or molecular sieve may be used to catalyze the reaction of DME and/or methanol and $H_2$ to produce a $C_1$-$C_9$ linear and branched olefin and paraffin stream.

A zeolite may contain pores formed from 6-membered ring, 8-membered ring, 10-membered ring, 12-membered ring, 18-membered ring, and/or a larger membered ring of silicon (or aluminum) and oxygen pairs. For example, the term "8-membered ring" refers to a closed loop that is built from eight tetrahedrally coordinated silicon (or aluminum) atoms and 8 oxygen atoms. These rings form pores with characteristic diameters. By way of example 8-membered ring ZK-5 (KFI) has a characteristic pore size of about 4 Å, 10-membered ring ZSM-5 has a characteristic pore size of about 5.5 Å, and 12-membered ring beta (BEA) zeolite has a characteristic pore size of about 7.5 Å. In some examples at least one of a 10-membered ring and/or a 12-membered ring zeolite may be used to catalyze the reaction of DME and/or methanol and $H_2$ to produce a $C_4$-$C_9$ linear and branched olefin and paraffin stream. In other cases, a 12-membered ring BEA zeolite may be used.

Solid catalysts, including zeolites and molecular sieves, may be incorporated in another material referred to herein as a "matrix" or "binder". Such matrix materials may include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with zeolite and/or molecular sieves include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. In some cases, a matrix or binder may also act as a catalyst.

As described above, a zeolite may contain Brønsted acid sites. A zeolite may also contain Lewis acid sites. Thus, a catalyst for reacting DME and/or methanol with $H_2$ may possess a combination Lewis acid sites, which may aid in hydrogen abstraction from hydrocarbon molecules, and Brønsted acid sites, which may aid in the alkylation and formation of successively larger hydrocarbon products. In general, a "Brønsted acid" is a substance that is a proton donor and a "Lewis acid" is a substance that can accept an electron. As used herein, "hydrogenation" refers to the addition of hydrogen atoms to a molecule.

By way of example only, and not intending to be bound by theory, a Brønsted acid site may be present within a zeolite pore. The number of sites (site density) and strength of the sites may define the speed and selectivity of catalyst embodiments of the present invention. Also by way of example only, Lewis acid sites may help re-incorporate alkanes back into a chain growth process. A catalyst, such as a zeolite, may include a Lewis acid, a Brønsted acid, and hydrogenation functions, with the strengths of the three balanced such that the hydrocarbon products synthesized using these catalysts may not be insufficiently Brønsted acidic (which may slow or stop hydrocarbon production), insufficiently Lewis acidic (which may minimize yields of desired hydrocarbon products), or excessively active in hydrogenation (which may quench the reaction and result in the production of only light ($C_2$-$C_3$) hydrocarbon products). In some cases, a solid catalyst may include Brønsted:Lewis ratios ranging from about 100:1 to about 1:1. In other examples, a solid catalyst may include Brønsted:Lewis ratios ranging from 15:1 to about 2:1.

Thus, various embodiments of the solid catalysts described above may be utilized for converting methanol and/or DME to a $C_4$-$C_9$ linear and branched olefin and paraffin fuel stream 170, as illustrated in FIG. 1. For example, a process for manufacturing a $C_4$-$C_9$ linear and branched olefin and paraffin fuel stream may utilize a solid catalyst that includes a hydrogen-exchanged zeolite with a framework of aluminum, silicon, and oxygen atoms, and a silica to alumina ratio ranging from about 100:1 to about 500:1. The solid catalyst may also include, a first active material of at least one of gallium, lanthanum, iron, zinc, and/or mixtures thereof deposited onto a surface and/or within the pores of the zeolite. The solid catalyst may also include a second active material incorporated into the framework of the zeolite, where the second active material includes at least one of silver, copper, platinum, gallium, palladium and/or mixtures thereof. Further, a first portion of the first active material may be present in elemental form, while a second portion of the first active material may be present in ionic form.

The catalyst, e.g. zeolite, may be provided in a reactor such as a fixed bed, a fluidized bed, a moving bed, an ebullient bed, a bubble column, and/or combinations thereof, for contacting DME and/or methanol and $H_2$ with the catalyst to produce a $C_1$-$C_9$ linear and branched olefin and paraffin stream. In addition, several reactors may be provided in series and/or in parallel. Also, multiple relatively small tubular reactors may be configured in parallel for advantages such as minimizing heat transfer limitations. Contacting of the reactants with the solid catalyst may be achieved in a reactor in continuous mode and/or batch mode. Continuous reactor residence times may range from about 0.1 seconds to about 1 hour. Batch reactor residence times may range from about 1 minute to about 48 hours. The reactor may be maintained at a reaction temperature ranging from about 150° C. to about 300° C. for contacting the reactants with the solid catalyst. Alternatively, the reactor may be maintained at a reaction temperature ranging from about 150° C. to about 200° C. for contacting the reactants with the solid catalyst. The reactor may be maintained at a reaction pressure ranging from about one atmosphere to about 100 atmospheres for contacting the reactants with the solid catalyst. Alternatively, the reactor may be maintained at a reaction pressure ranging from about one atmosphere to about 10 atmospheres for contacting the reactants with the solid catalyst.

In some cases, the $C_4$-$C_9$ linear and branched olefin and paraffin production process (numeral 160 in FIG. 1) may include, prior to the contacting the reactants with the solid catalyst, an activating step, where the solid catalyst undergoes substantial oxidation by exposing the solid catalyst to air at an elevated temperature. For example, the solid catalyst may be activated by contacting the solid catalyst with air at a temperature ranging from about 300° C. to about 700° C. Alternatively, the solid catalyst may be activated by contacting it with air at a temperature ranging from about 400° C. to about 600° C. Activation of the solid catalyst may also include contacting the catalyst with $H_2$ at a temperature ranging from about 50° C. to about 400° C. Alternatively, activation of the catalyst may include contacting it with $H_2$ at a temperature ranging from about 150° C. to about 300° C. Thus, in some cases, the solid catalyst may be activated in a two-step process, where the first step is an air-activation step, and the second step is a $H_e$-activation step.

Referring again to FIG. 1, the DME and/or methanol stream 150 and the $H_2$ stream 180 provided to the $C_4$-$C_9$ linear and branched olefin and paraffin process 160 may be varied as needed. In some examples, a reactant stream provided to a $C_1$-$C_9$ linear and branched olefin and paraffin production reactor may include a stoichiometric ratio ranging from about a half mole of DME for every mole of $H_2$ to about two moles of DME for every mole of $H_2$. In other examples, a reactant stream provided to a $C_1$-$C_9$ linear and branched olefin and paraffin production reactor may include a stoichiometric ratio that ranges from about a half mole of methanol for every mole of $H_2$ to about two moles of methanol for every mole of $H_2$. Alternatively, a reactant stream may include a stoichiometric ratio that ranges from about a half mole of methanol for every mole of DME to about two moles of methanol for every mole of DME. In addition, a reactant feed stream may include a stoichiometric ratio of $H_2$ to DME/methanol that ranges from about 100:1 to about 1:100. Alternatively, a reactant feed stream may include a stoichiometric ratio of $H_2$ to DME/methanol that ranges from about 10:1 to about 1:10. However, the DME to methanol stoichiometric ratio may be varied as needed for a particular product mixture. In some examples, the $C_1$-$C_9$ linear and branched olefin and paraffin production process may have a reactant feed stream of $H_2$ and DME (no methanol). Alternatively, the reactant feed stream may include $H_2$ and methanol (no DME). So, in some cases, the reactant stream to be brought into contact with the solid catalyst (e.g. zeolite) for $C_1$-$C_9$ linear and branched olefin and paraffin production may be free from $H_2$. In addition, the reactant stream for contacting with the solid catalyst for $C_1$-$C_9$ linear and branched olefin and paraffin production may also include an inert diluent, such as nitrogen ($N_2$), helium (He), and/or argon (Ar).

Thus, while not intending to limit the present invention by theory, some embodiments of a catalyst for converting DME and/or methanol and $H_2$ to a $C_4$-$C_9$ linear and branched olefin and paraffin fuel may include catalytic activities beyond Brønsted acidity and local confinement (e.g. zeolite HBEA) to include Lewis acid centers and metal centers capable of adsorbing and dissociating $H_2$ and hydrogenating olefins and/or isomerizing paraffins. The Lewis function may serve to remove hydrogen from paraffins (e.g., isobutane) to produce olefins that may reenter the catalytic cycle (as proposed by Simonetti et al.). The metal function may serve to add hydrogen to olefins to form saturated paraffins and possibly replenishes protons at Brønsted sites that may otherwise be removed by reactions in the catalytic cycle and may be unable to be replenished by $H_2$ without the metal function.

Simulation studies have identified numerous other potential benefits that may result from the use of some of the zeolite catalyst embodiments described herein. For example, the zeolite catalysts described herein may result in increased apparent rates of reaction (productivities), and/or the increased overall turnover due to the replenishment of Brønsted protons. The practical implication resulting from these improvements may be that less catalyst (smaller reactor volume) may be required to perform the same level of reactant conversion, which may lower plant capital costs and improve process economics.

Another potential advantage resulting from some embodiments of the zeolite catalysts described herein is that 'dead-end' products like isobutane are dehydrogenated to regenerate active olefins that subsequently reenter the catalytic cycle, potentially resulting in less "waste" to butanes. In a recycle scenario where all $C_4$— products are sent back to the reactor, in theory, all of these intermediate products may be homologated to larger, more desirable products (like triptane), which may result in increased yields of high-value product and less waste. Some catalysts described herein may also raise the paraffin to olefin ratios. The paraffin products have a higher value than the olefin products (as a mixture) and a higher degree of saturation in the product may increase the octane rating and may potentially eliminate the need for a separate hydrogenation reactor downstream to saturate the olefins.

In addition, some of the catalysts described herein may affect the relative production rates of aromatic byproducts by reducing their production by as much as one-third relative to current technologies. This may result in lower carbon losses to byproducts and a higher yield of preferred high value products. An additional potential advantage resulting from the use of some of the catalysts described herein is that the "coke" formed, which may deactivate the catalyst, may be more easily removed than the coke formed using typical catalysts, thus reducing the temperature at which oxidation of coke occurs, potentially by several hundred degrees Celsius.

Figure 5A:
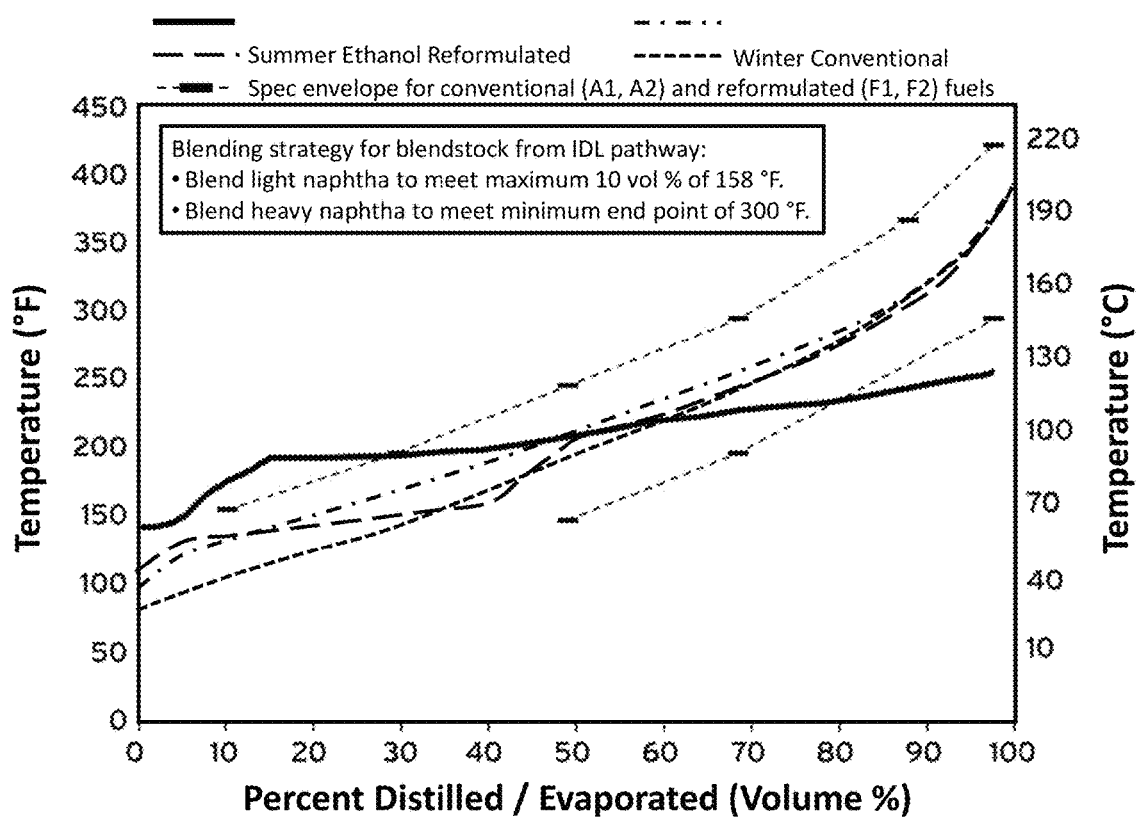
FIGS. 5a and 5b summarize predicted physical property values for some of the gasoline range fractions produced by the reaction of DME and/or methanol with $H_2$, according to exemplary embodiments of the present invention.
Figure 5B:
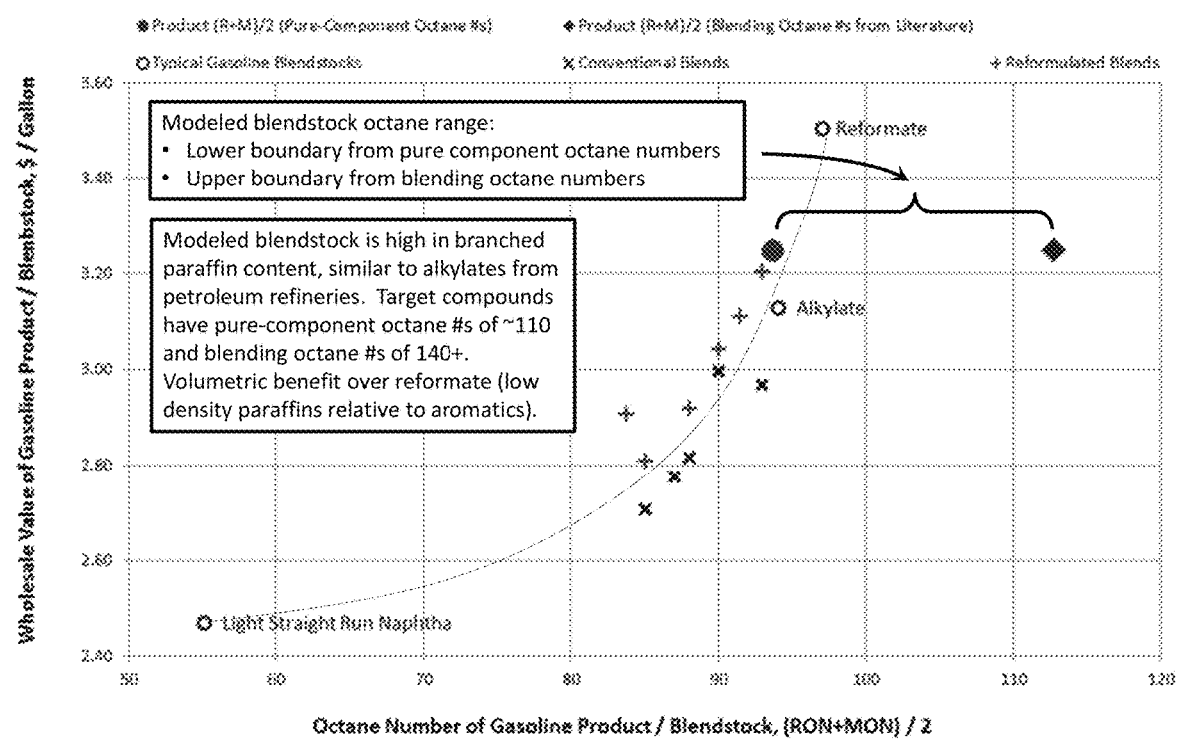
Figure 36:
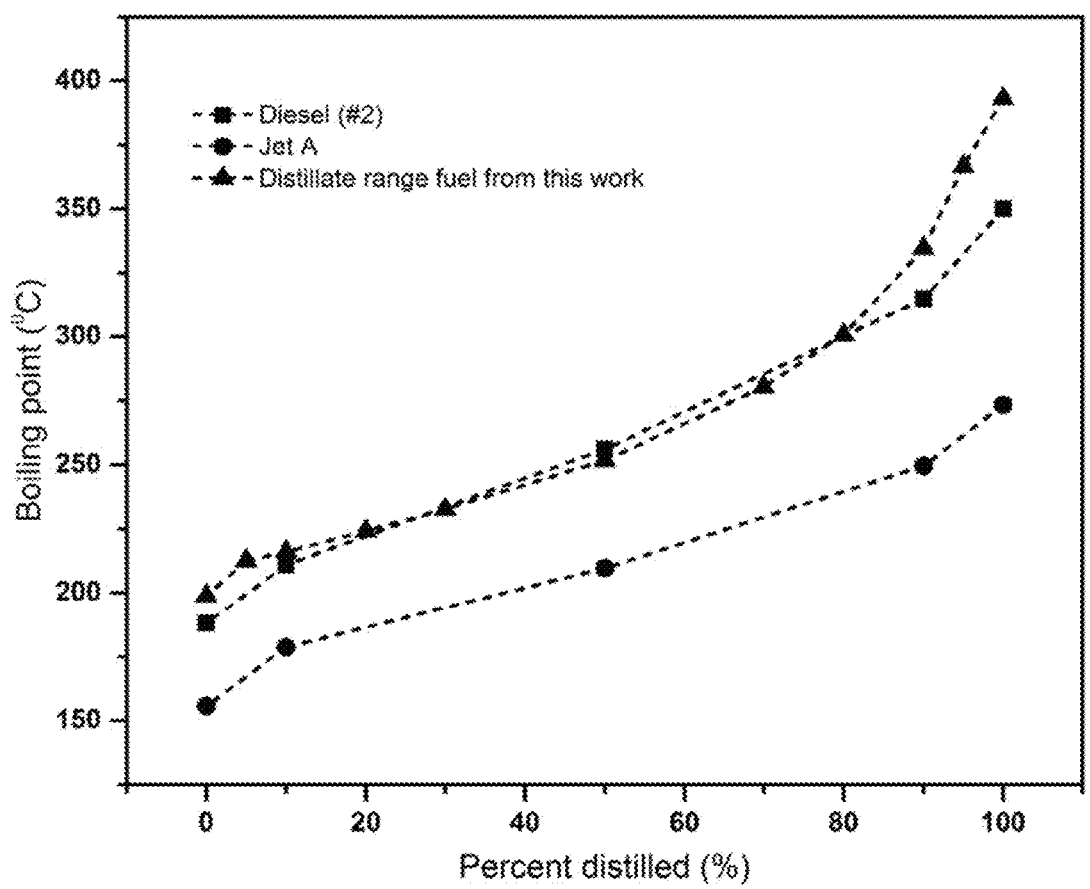
FIG. 36 illustrates the boiling point range of distillate fractions from the final product mixture as obtained from the simulated gas chromatographic distillation performed following ASTM-D2887, according to exemplary embodiments of the present invention.

Coupling of $C_4$-$C_9$ Linear and Branched Olefin and Paraffin Fuels to Gasoline and Distillate-Range Hydrocarbon Fuels Referring again to FIG. 1, the $C_4$-$C_9$ linear and branched olefin and paraffin fuel 170 produced in the $C_4$-$C_9$ linear and branched olefin and paraffin production process 160 may be used as fuels themselves. FIGS. 5a and 5b illustrate some predicted physical property values for an exemplary $C_4$-$C_9$ linear and branched olefin and paraffin fuel that approximates the performance and physical properties of a gasoline fuel. Specifically, FIG. 5a illustrates the predicted boiling point range for an exemplary $C_4$-$C_9$ linear and branched olefin and paraffin fuel 170 and FIG. 5b illustrates predicted octane ratings for an exemplary $C_4$-$C_9$ linear and branched olefin and paraffin fuel. An example of a gasoline fuel is a mixture of aliphatic hydrocarbons typically ranging in length from about 4 to about 7 carbon atoms ($C_4$ to $C_7$). Alternatively, the $C_4$-$C_9$ linear and branched olefin and paraffin fuel 170 may be further processed in a downstream coupling process 190 to produce higher molecular weight fuels, gasoline and distillate-range hydrocarbon fuel 195. So, for example, at least one of 2,2,3-trimethylbutane, 2,3,3-trimethyl-1-butene, or mixtures thereof may be further reacted to produce higher molecular weight compounds. FIGS. 36 and 39 illustrate some predicted physical property values for the distillate-range hydrocarbon fuel within the mixture 195. In some examples, an alcohol may be included in a mixture of at least one of 2,2,3-trimethylbutane and/or 2,3,3-trimethyl-1-butene. Examples of alcohols include methanol, ethanol, propanol, isopropyl alcohol, butyl alcohol, and/or pentanol. In some cases, the gasoline and distillate-range hydrocarbon fuel 195 may be produced by one or more coupling reactions of one or more paraffins and/or olefins. In other cases, a gasoline and distillate-range hydrocarbon fuel may be obtained by coupling reactions of a renewable, biomass-derived deoxygenated olefinic precursor or mixture.

For example, the $C_4$-$C_9$ linear and branched olefin and paraffin fuel stream 170 may be reacted to produce higher molecular weight hydrocarbons streams, gasoline and distillate-range fuels 195, that approximate the performance and physical properties of diesel, jet fuel, and/or mixtures thereof. These hydrocarbons fuels may be produced by various reactions including, but not limited to, the reactions of at least one of an olefin, a triptene, 2,3-dimethyl-1-butene, 2,3,3-trimethyl-1-butene, 2,4,4-trimethyl-1-pentene, and/or mixtures thereof. Reactions may include the dimerization of identical compounds, the coupling of different compounds, and/or combinations thereof. An example of a diesel fuel or jet fuel is a mixture of hydrocarbons typically ranging in length from about 8 to about 21 carbon atoms ($C_8$ to $C_{21}$).

Referring again to FIG. 1, in some examples, the gasoline and distillate-range hydrocarbon fuel 195 produced by treating the $C_4$-$C_9$ linear and branched olefin and paraffin fuel stream 170 in the coupling process 190 may include branched $C_4$ to $C_7$ paraffins and olefins. In other examples, the gasoline and distillate-range hydrocarbon fuel 195 may include branched paraffins and olefins larger than $C_7$. In still other example, the gasoline and distillate-range hydrocarbon fuel 195 may include $C_7$+ paraffins and olefins, which may be produced by reacting at least two $C_4$ to $C_7$ olefins together to form $C_7$+ paraffins and olefins. In addition, the gasoline and distillate-range hydrocarbon fuel may include straight-chained and/or branched paraffins and/or straight-chained and/or branched olefins.

The conversion of a $C_4$-$C_9$ linear and branched olefin and paraffin fuel to a distillate-range hydrocarbon fuel may be catalyzed by at least one of a homogeneous catalyst, a heterogeneous catalyst, or a mixture thereof. In some examples, the catalyst may be a solid acid catalyst. Examples of solid acid catalysts include acid-functionalized ion-exchange resins, aluminosilicates, and/or hydrogen containing oxides. An example of an ion-exchange resin for reacting a $C_4$-$C_9$ linear and branched olefin and paraffin fuel mixture to a higher molecular weight gasoline and distillate-range hydrocarbon fuel mixture is a styrenic-divinyl benzene functionalized with sulfonic groups —$SO_3H^+$, such as Amberlyst-35™. For example, an ion-exchange resin may be used to catalyze the coupling of 2 olefins to a product having a carbon number that is the sum of the carbon numbers of the original olefins, wherein the ion-exchange resin may be characterized by a high density of active proton sites (≥about 5.0 eq/kg). An ion-exchange resin may also be used to catalyze the coupling of olefins to a product having a carbon number that is the sum of the carbon numbers of the original olefins, where the ion-exchange resin may be characterized by a low-to-moderate acid strength (with Hammett acidity function ($H_o$) of about −2.2).

In addition, the reaction of a $C_4$-$C_9$ linear and branched olefin and paraffin fuel to a distillate-range hydrocarbon fuel may be carried out in the presence of a solvent. A solvent may include at least one non-polar solvent. In other cases, a solvent may include at least one of an aprotic solvent, or mixtures thereof. Some examples of solvents that may be used in coupling process include nonane, pentadecane, ocatane, pentane, cyclopentane, hexane, cyclohexane, benzene, and/or toluene. However, the use of a solvent is optional.

The conversion of a $C_4$-$C_9$ linear and branched olefin and paraffin fuel to a distillate-range hydrocarbon fuel may be completed in the liquid phase in a batch or continuous reactor. An example of a batch reactor includes a stirred reactor with or without baffles. Examples of continuous reactors include a continuous stirred tank reactor and a packed-bed reactor. In some embodiments of the present invention, the coupling of at least one olefin to a second olefin may be carried out in the liquid phase in a batch stirred reactor or a continuously stirred tank reactor that is mechanically agitated using at least one rotating impeller rotating at a rate from 10 to 1000 rpm. In some cases, the reaction of a $C_4$-$C_9$ linear and branched olefin and paraffin fuel to a distillate-range hydrocarbon fuel may be carried out at a reactor temperature that is elevated above normal room temperature. For example, a reaction temperature for converting a $C_4$-$C_9$ linear and branched olefin and paraffin fuel stream to distillate-range hydrocarbon fuel may range from about 40° C. to about 200° C. Alternatively, the reaction temperature may range from about 40° C. to about 150° C. In some cases, the conversion of a $C_4$-$C_9$ linear and branched olefin and paraffin fuel to a distillate-range hydrocarbon fuel may be carried out at a reactor pressure ranging from about 1 atmosphere to about 100 atmospheres. In other cases, the conversion of a $C_4$-$C_9$ linear and branched olefin and paraffin fuel to a distillate-range hydrocarbon fuel may be carried out at a pressure ranging from about 0.6 atmospheres to about 7 atmospheres. The conversion of a $C_4$-$C_9$ linear and branched olefin and paraffin fuel to a distillate-range hydrocarbon fuel may be carried out in a reactor wherein the reaction time ranges from about 1 minute to about 24 hours. In addition, the conversion of a $C_4$-$C_9$ linear and branched olefin and paraffin fuel to a distillate-range hydrocarbon fuel may be carried out in packed bed reactor wherein the particle Reynold's number ranges from about 0.1 to 10, wherein the particle Reynold's number is defined herein as the product of the empty volume velocity and the characteristic particle size, divided by the kinematic viscosity.

In some examples, a coupling reaction of at least one olefin, e.g. triptene, to at least one product having the sum of the carbon numbers in the reactants may be accompanied by at least one of an isomerization reaction, an oligomerization reaction, and/or a cracking reaction. The conversion of a $C_4$-$C_9$ linear and branched olefin and paraffin fuel stream 170 to a gasoline and distillate-range hydrocarbon fuel 195 may be carried out, for example, by passing the $C_4$-$C_9$ linear and branched olefin and paraffin fuel stream 170, in liquid form, over a solid catalyst. Examples of such a solid catalyst include acid catalysts such as acid functionalized ion exchange resins.

As stated above, a coupling process for converting a $C_4$-$C_9$ linear and branched olefin and paraffin fuel to a gasoline and distillate-range hydrocarbon fuel may include a mixture of reactants and numerous reactions to produce a mixture of products. For example, a $C_4$-$C_9$ linear and branched olefin and paraffin fuel stream may include 2,3,3-trimethyl-1-butene (triptene), 2,3-dimethyl-1-butene, and/or 2,4,4-trimethyl-1-pentene. The coupling process may then include one or more of dimerization, coupling, isomerization, oligomerization, and/or cracking reactions to produce a gasoline and distillate-range hydrocarbon fuel containing a variety of species. An exemplary distillate-range hydrocarbon fuel may include 2,2,3,5,5,6,6-heptamethyl-3-heptene (di-triptene), 2,2,4,6,6-pentamethyl-3-heptene, 2,2,3,5,6-pentamethyl-3-heptene, 2,3,5,5,6-pentamethyl-3-heptene, 2,2-dimethyl-3-octene, and/or 2,2,4,6,6,8,8-heptamethyl-4-nonene. Examples of coupling reactants that may be contained in a $C_4$-$C_9$ linear and branched olefin and paraffin fuel stream includes 2-methyl-1-hexene, 2,3,3-trimethyl-1-butene (triptene), 2,3-dimethyl-1-butene, 2,4,4-trimethyl-1-pentene, 2-methylpropene (isobutene), and/or 1-heptene.

It is appreciated that certain features of the invention, which are, for clarity, described in the context of separate embodiments, may also be provided in combination in a single embodiment. Conversely, various features of the invention that are, for brevity, described in the context of a single embodiment, may also be provided separately or in any sub-combination.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

Figure 6:
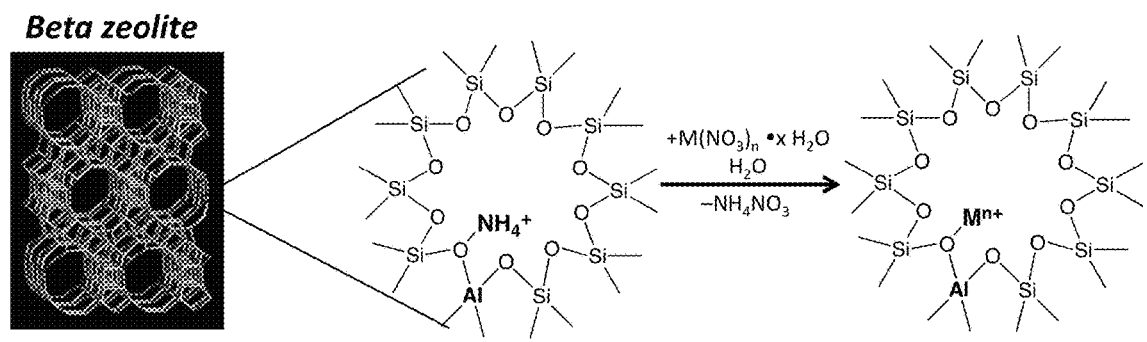
FIG. 6 illustrates a cation exchange method for depositing metal ions onto surfaces of a zeolite, according to exemplary embodiments of the present invention.

Example 1: Conversion of DME to $C_4$-$C_9$ Linear and Branched Olefin and Paraffin Fuels Zeolite type beta (Tosoh, Si:Al=13.5) with metals (Ga, Cu, Zn, La, and Fe) supported on the beta zeolite were used for the conversion of DME to a $C_1$-$C_9$ linear and branched olefin and paraffin containing mixture, that included $C_7$ branched hydrocarbons. The starting beta zeolite catalyst was procured in the ammonium form ($NH_4BEA$) and the metals were deposited on the zeolite ("impregnations") using either ion exchange methods or wet impregnation methods. For ion exchange methods, $NH_4BEA$ (5.0 g) was suspended in 75 mL of DI water with stirring. A solution of $M(NO_3)_3 \cdot xH_2O$ (M=metal, 0.100 g, $3.91 \times 10^{-4}$ mol, 27.3 mg M for anhydrous nitrate) in 25 mL DI water was added dropwise to the zeolite suspension at room temperature over about 5 minutes, where M was Ga. The reaction was heated at 60° C. for 2 hours with stirring. A powder product was isolated via vacuum filtration on a Buchner funnel, rinsing 1×50 mL with DI water. The powder product was dried in an oven at 120° C. for 16 hours. The ion exchange method is shown schematically in FIG. 6. This method yielded materials having approximately 0.5 wt % metal, with results tabulated below in Table 1.

TABLE 1

| Catalyst | $S_{BET}$ (m²/g) | Metal wt % |
|---|---|---|
| NH₄-β | 228 | — |
| Ga-β | — | 0.454 |
| Fe-β | — | 0.475 |
| Cu-β | — | 0.0852 |
| Zn-β | — | 0.0885 |

Table 1 illustrates that $Ga^{3+}$ and $Fe^{3+}$ achieved higher loadings than the $Cu^{2+}$ or $Zn^{2+}$ using the ion exchange method. This may be due to the relative acid strength of the $M^{n+}$ cation. The cations $Ga^{3+}$ and $Fe^{3+}$ are more Lewis acidic than $Cu^{2+}$ and $Zn^{2+}$, and therefore, $Ga^{3+}$ and $Fe^{3+}$ may be expected to form a stronger bond with surface O⁻ anions.

For wet impregnation methods, NH₄BEA (5.0 g) was impregnated drop-wise with a solution of the desired metal using $M(NO_3)$-$xH_2O$ in 9 mL of DI water. The resulting paste was dried at 50-75° C. for 16 hours. The resultant metal loadings achieved ranged from about 1 wt % and to about 5 wt %. The resultant catalysts produced, with a metal active site deposited on a surface of a beta zeolite is referred to herein as Ga/NH₄BEA, Cu/NH₄BEA, Zn/NH₄BEA, La/NH₄BEA, and Fe/NH₄BEA, respectively. A beta zeolite with Ga incorporated into the beta zeolite's framework was also synthesized according to M. A. Camblor et al., *Zeolites*, 1992, 12, 280-286. This catalyst, with Ga incorporated into the zeolites framework, is referred to herein as Ga—Si—Al BEA.

Figure 7:
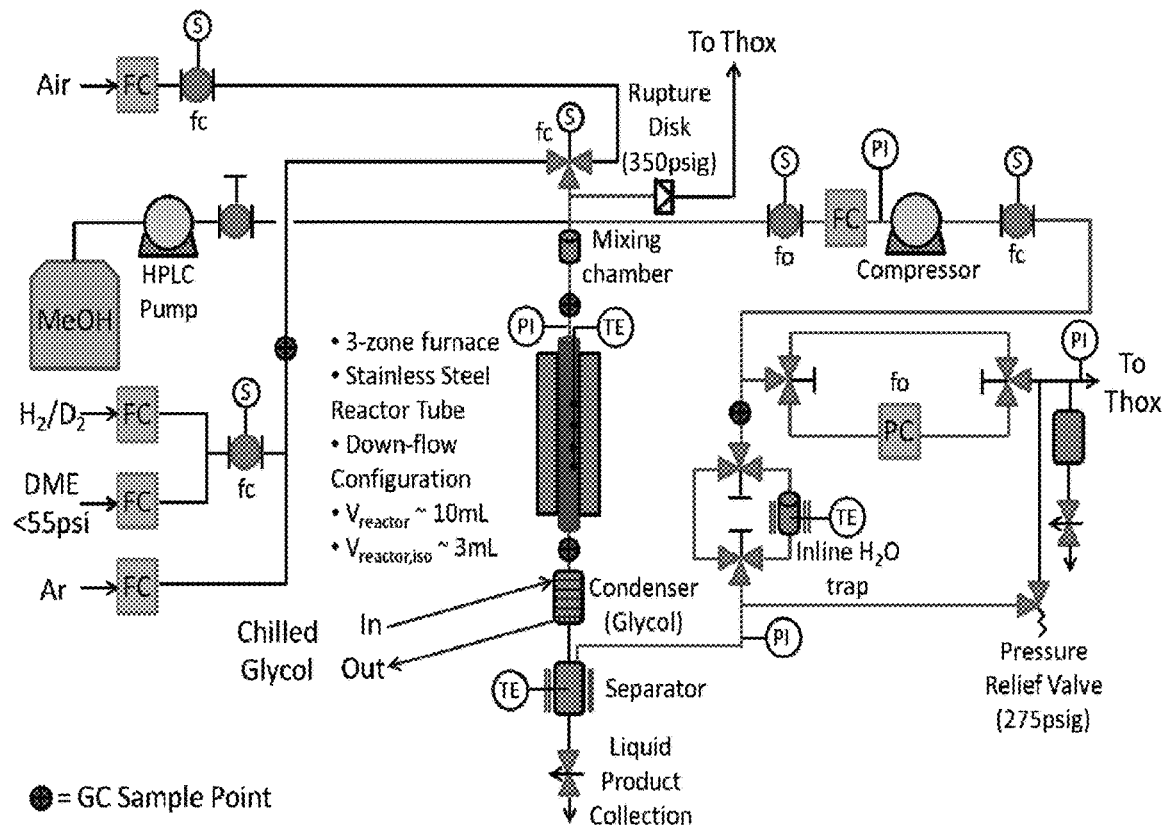
FIG. 7 illustrates a reactor for converting DME and $H_2$ to $C_1$ to $C_9$ linear and branched olefins and paraffins, according to exemplary embodiments of the present invention.

For each of the catalysts produced, catalyst powders were sized between 180-250 μm (60-80 mesh) with no further manipulation. Samples were diluted by mixing 0.6 g of catalyst with 3.6 g inert silicon carbide (SiC) of similar size. Smaller catalyst particles did not impact product distribution, suggesting that the reactor was operating under kinetic limitation, free of mass transfer effects. Blended samples were loaded within the isothermal zone of a vertically-mounted stainless steel plug flow reactor (13 mm ID), supported above and below with quartz chips. The reactor was heated with a three zone clamshell furnace and the reactor tube was tightly wrapped in copper wire to promote uniform heating within the furnace. Reaction temperatures within the reactor were monitored with thermocouples positioned directly above, within, and at the bottom of the catalyst bed and was controlled with a master-slave algorithm. A schematic of the reactor system is shown in FIG. 7.

Unless otherwise specified, each of the catalysts tested in Example 1 were first activated by heating for 10 hours at 500° C. in 120 sccm of a lab-produced mixture of about 21 vol % $O_2$ and about 79 vol % $N_2$ to convert to the proton form (represented as either BEA or HBEA) from the ammonia form. The resultant catalysts are referred to herein Ga/BEA, Cu/BEA, Zn/BEA, La/BEA, and Fe/BEA. Following this activation, 5 wt % Cu/BEA, 5 wt % Zn/BEA, and 5 wt % La/BEA were further activated in $H_2$ for 10 h at 120 sccm at 300° C. (Cu) or 500° C. (Zn and La). Hydrocarbon synthesis (DME homologation) experiments were performed at 200° C. at atmospheric pressure for 24 hours. The gas feed was either i) 4.9 sccm Argon and 7.1 sccm DME, or ii) 1 sccm Argon, 7.1 sccm DME, and 7.1 sccm $H_2$. These two feed mixtures were used to probe the impact of $H_2$ on catalyst performance.

Reactor inlet and outlet gases were sampled through heated lines to an Agilent 7890 GC equipped with FID and TCD detectors for analysis of oxygenates/hydrocarbons and permanent gases/water, respectively. The GC responses for $C_1$-$C_4$ hydrocarbons, n-pentane, n-hexane, pentane, and permanent gases were calibrated using Scott Master Class gas standards. Responses for other hydrocarbons were estimated through response factors, derived from extrapolations of calibration data. Water was calculated using tabulated response factors for $CO_2$ and water and the $CO_2$ calibration curve. Product identifications were achieved by loading gas-bag samples on a separate GC with a mass spectrometer (MS), with species suggested by NIST spectral libraries and confirmed by chemical standards. Catalyst performance was evaluated solely from inlet flow and GC measurements using Ar as an internal standard.

Figure 8:
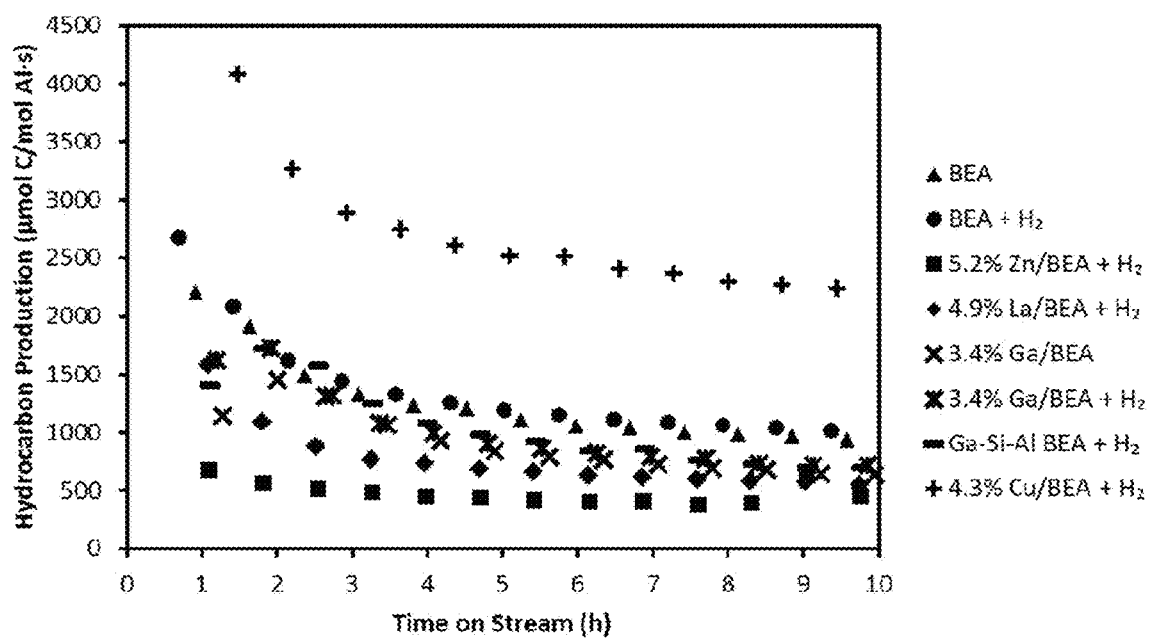
FIG. 8 compares the hydrocarbon productivity of the various catalysts made by an incipient wetness method and used in the reaction of DME and $H_2$, according to exemplary embodiments of the present invention.
Figure 9:
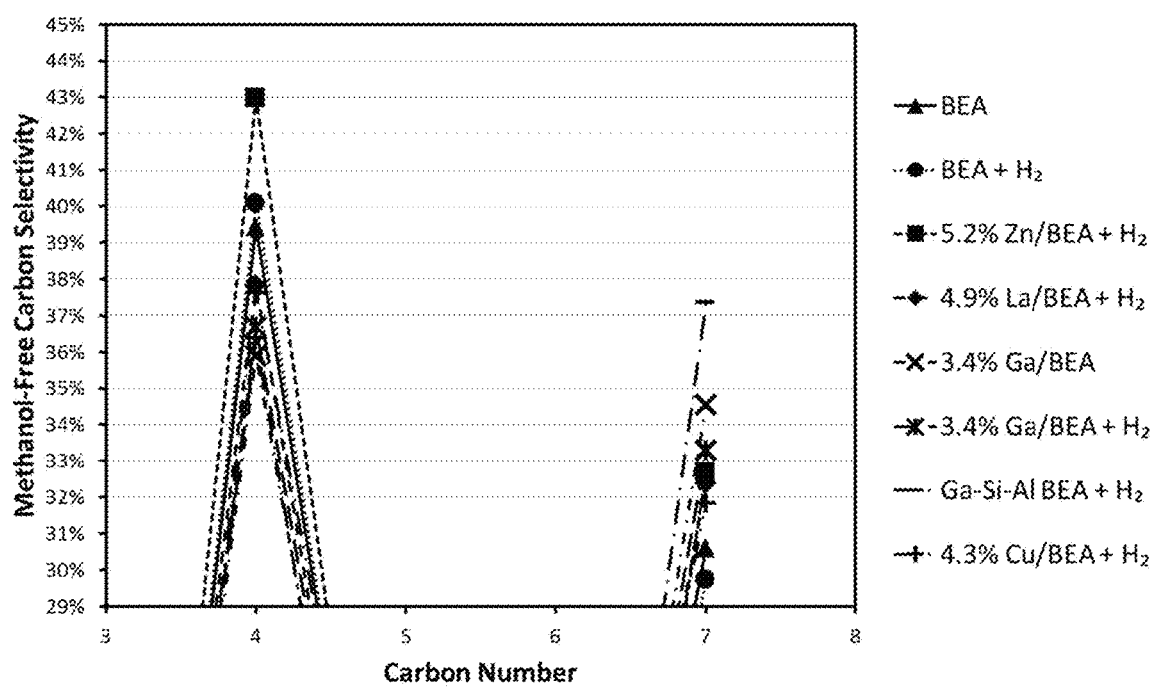
FIG. 9 compares the carbon selectivity of the various catalysts made by an incipient wetness method and used in the reaction of DME and $H_2$, according to exemplary embodiments of the present invention.
Figure 10:
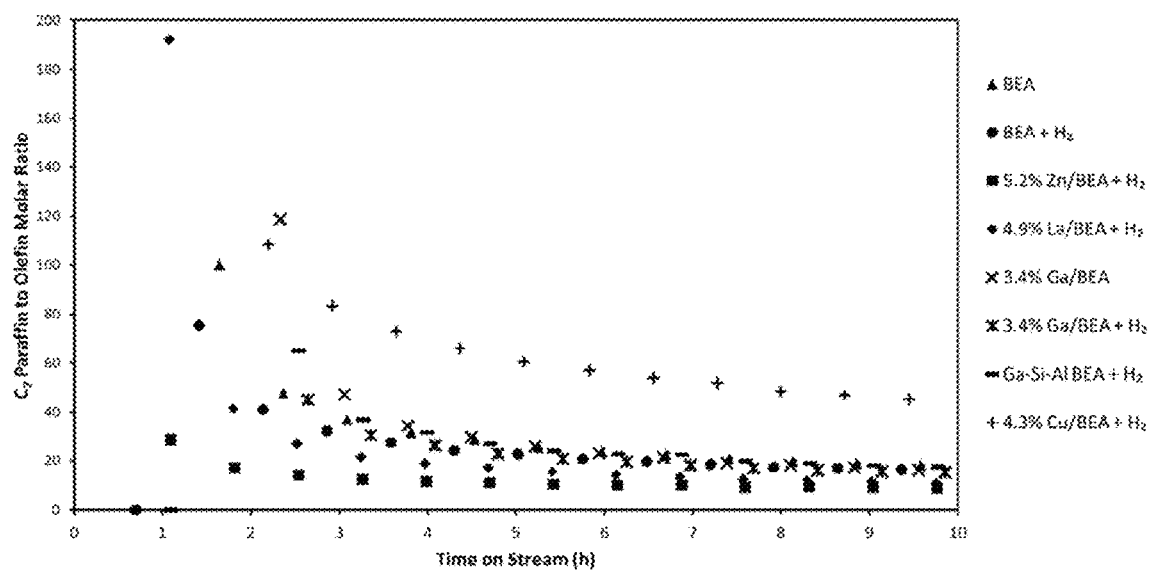
FIG. 10 compares the $C_7$ paraffin/olefin selectivity of the various catalysts made by an incipient wetness method and used in the reaction of DME and $H_2$, according to exemplary embodiments of the present invention.

FIGS. 8-10 illustrate and compare the performances of the catalysts synthesized by the wet impregnation method. FIG. 8 compares the hydrocarbon productivity of the various catalysts to the starting BEA catalyst (absent any kind of metal active site). This figure shows that the Cu/BEA catalyst exhibited a 2× higher hydrocarbon productivity than the BEA catalyst, without a metal active site. All of the other catalysts demonstrated hydrocarbon productivities that were less than the BEA catalyst, including the Ga—Si—Al BEA catalyst. FIG. 9 illustrates the carbon selectivity for the same catalysts. This figure shows that the Ga—Si—Al BEA catalyst showed in increased selectivity to C7 hydrocarbons while the Cu/BEA catalyst showed a selectivity that was similar to unmodified BEA catalyst. FIG. 10 illustrates the paraffin/olefin selectivity for the same catalysts. This figure shows that the Cu/BEA catalyst exhibited the highest selectivity to paraffins. In general, the paraffin/olefin ratio decreased as a function of time on stream.

Example 2: Cu/BEA Catalysts for the Conversion of DME to $C_4$-$C_9$ Linear and Branched Olefin and Paraffin Fuels A Cu/HBEA catalyst for the conversion of DME to $C_4$-$C_9$ linear and branched olefins and paraffins was prepared as follows. Beta zeolite (BEA) having a $SiO_2/Al_2O_3$ ratio of about 27 was obtained in ammonium-form. The NH₄BEA powder was used as received, and had a particle/agglomerate size range of about 45 μm to about 125 μm. To produce Cu/BEA catalysts, an aqueous solution of $Cu(NO_3)_2$.2.5 $H_2O$ (~0.961 g in ~9 mL deionized water) was added dropwise to powdered NH₄BEA (~4.95 g) to reach the incipient wetness point. The slurry was briefly mixed, and then dried in an oven at about 50° C. overnight to give Cu/NH₄BEA. The targeted Cu loading was about 5 wt %, and the actual measured loading (by elemental analysis) was about 4.3 wt %. The measured weight loading corresponds to ~60% of the theoretical ion-exchange capacity of the parent NH₄BEA. A ~5% Cu/SiO₂ control sample was also prepared by the analogous incipient wetness method by adding $Cu(NO_3)_2$.2.5 $H_2O$ (~0.92 g in 27 mL water) to silica (~4.75 g: particle size ~50 μm). The measured Cu loading was about 5.3 wt %.

The NH₄BEA and Cu/NH₄BEA catalysts were activated prior to characterization and catalytic testing. The NH₄BEA catalyst was activated in a flowing oxidizing mixture (air, ~1% $O_2$/He, or ~10% $O_2$/Ar depending upon the experiment) and while heating to about 500° C. at about 2° C./min. The catalyst was then held at about 500° C. for a minimum of about 5 hours. This procedure converted the BEA from the ammonium-form (NH₄BEA) to the proton-form (HBEA). This catalyst is denoted as HBEA in this example. The Cu/NH₄BEA catalyst was activated as described for NH₄—BEA (and will be referred to as ox-Cu/BEA in this example). In some cases, this material was cooled to about 300° C. directly after activation, and exposed to flowing $H_2$ for a minimum of about 2 hours to reduce Cu (and will be referred to as red-Cu/BEA in this example).

Example 2: Cu/BEA Catalysts for the Conversion of DME to $C_4$-$C_9$ Linear and Branched Olefin and Paraffin Fuels—Catalyst Characterization Elemental analysis of Cu was determined using inductively coupled plasma atomic emission spectroscopy. Powder X-ray diffraction data were collected using a Rigaku Ultima IV diffractometer with a Cu Kα source. Diffractograms were collected in the 2θ range of about 10 degrees to about 60 degrees at a scan rate of about 2°/minutes. Samples (ranging from about 10 mg to about 20 mg) were supported on a glass sample holder with a 0.2 mm recessed sample area and were pressed into the recession with a glass slide to obtain a uniform z-axis height. Cu and CuO crystallite sizes were calculated using the Scherrer equation.

TEM was performed on red-Cu/BEA on an FEI G20 Tecnai TEM operating at 200 kV. Following reduction, a sample of the red-Cu/BEA was dispersed in anhydrous toluene under air-free conditions and dropped onto a carbon coated Cu mesh grid. Air exposure was minimized prior to TEM imaging.

Temperature-programmed reduction (TPR) experiments were carried out in a U-shaped quartz tube under atmospheric pressure. The reactor was loaded with a mixture of about 50 mg of Cu/NH$_4$BEA catalysts and about 300 mg of quartz chips (from about 30 mesh to about 40 mesh). The catalyst sample was activated by heating to about 500° C. at about 2° C./min and holding at ~500° C. for about 2 hours in flowing 1% O$_2$/He (20 mL/min). The sample was then cooled to room temperature in flowing He before heating to about 600° C. at ~10° C./min in ~2% H$_2$/He (20.4 mL/min). The gas composition was monitored by a mass spectrometer.

The total number of acid sites was determined using NH$_3$ TPD on an Altamira Instruments AMI-390 system with gas flow rates of about 25 mL/min. Catalyst samples (about 250 mg) were loaded into a ½" quartz U-tube reactor and held as a fixed bed between plugs of quartz wool. Samples were calcined in flowing ~10% O$_2$/Ar at about 2° C./min to about 500° C., and then held at this temperature for about 5 hours. For the red-Cu/BEA catalyst, the sample was subsequently reduced in flowing ~10% H$_2$/Ar at about 300° C. for about 5 hours. The samples were cooled to about 120° C. in flowing He and then saturated with flowing ~10% NH$_3$/He for about 30 minutes. Excess and/or physisorbed NH$_3$ was removed by holding the samples at ~120° C. in flowing He for about 1 hour. TPD of NH$_3$ was performed by heating the sample from about 120° C. to about 500° C. at ~30° C./min. The temperature was then held at about 500° C. for about 30 minutes to allow any remaining NH$_3$ to desorb without increasing the temperature above the 500° C. activation temperature. Desorbed NH$_3$ was measured with a thermal conductivity detector, and calibration was performed after each experiment by introducing 5 pulses of ~10% NH$_3$/He from a 5 mL sample loop into a stream of flowing He.

The relative amounts of Lewis and Brønsted acid sites were determined using py-DRIFTS, which were recorded on a Thermo Nicolet iS50 FT-IR spectrometer operating at 4 cm$^{-1}$ resolution with a Harrick praying mantis attachment and Si windows operated at ambient pressure. As-prepared materials were activated in-situ at about 500° C. in flowing air (~50 mL/min, ~2° C./min from ambient, ~10 hour soak), and then purged with flowing nitrogen at about 150° C. for about 30 min. For red-Cu/BEA, the catalyst was reduced in ~5% H$_2$ at about 300° C. for about 4 hours. After pretreatment, the sample was held at about 150° C., and saturated pyridine vapor was introduced with N$_2$ for ~5 minutes. The sample was then heated to about 300° C. under flowing nitrogen (or ~5% H$_2$ for red-Cu/BEA) to remove excess and/or physisorbed pyridine. The absorption peaks at 1545 cm$^{-1}$ (Brønsted) and 1445 cm$^{-1}$ (Lewis) and their relative absorption coefficients ($\epsilon_B/\epsilon_L$=0.76) were used to determine the relative Brønsted/Lewis acid site ratios.

The amount of HMB remaining on the catalyst after reaction was determined using $^1$H NMR spectroscopy. Solution-phase $^1$H and $^2$H NMR spectra were recorded using a Varian Inova 400 MHz spectrometer. Post-reaction catalyst samples (about 100 mg) were combined with solvent (~0.7 mL CDCl$_3$ for $^1$H; ~0.7 mL CHCl$_3$ for $^2$H) and internal standard (~10 μl CH$_2$Cl$_2$) in a sealed NMR tube. The tube was shaken briefly, and analyzed for solubilized organics.

H-D exchange experiments were carried out in a U-shaped quartz tube at atmospheric pressure. Samples of as-prepared materials (about 50 mg) were converted to the proton-form in-situ by heating at ~2° C./min to about 500° C. and holding for about 2 hours under flowing ~1% O$_2$/He (~20 mL/min). For the red-Cu/BEA catalyst, the sample was reduced at about 300° C. for about 2 hours under flowing H$_2$ (~20 mL/min, undiluted, 99.999%). The samples were cooled to room temperature in He, and then heated at ~10° C./min to about 800° C. in flowing D$_2$ (Matheson, 99.999%) at ~20 mL/min. A mass spectrometer was used to measure the effluent gas composition.

The dehydrogenation of isobutane was performed in a U-shaped quartz tube at atmospheric pressure. The as-prepared catalyst (about 100 mg) was mixed with about 300 mg of quartz chips (from about 30 mesh to about 40 mesh) and then loosely packed into the reactor with quartz wool. Catalysts were activated by heating to about 500° C. at about 2° C./min in flowing ~1% O$_2$/He (20 mL/min), and holding at about 500° C. for about 2 hours. For red-Cu/BEA, the catalyst was reduced at ~300° C. for about 2 hours in flowing H$_2$ (~20 mL/min, undiluted, 99.999%). After pre-treatment, the catalyst sample was heated from room temperature to about 600° C. at about 10° C./min in ~1% isobutane/He at a flow rate of about 5 mL/min. A mass spectrometer was used to monitor the reaction products.

X-ray absorption measurements were acquired on the bending magnet beam line (10-BM) of the Materials Research Collaborative Access Team (MRCAT) at the Advanced Photon Source, Argonne National Laboratory. Photon energies were selected using a water-cooled, double-crystal Si(111) monochromator, which was detuned by approximately 50% to reduce harmonic reflections. Measurements were made in transmission mode, and data points were acquired in three separate regions (energies relative to the elemental Cu K edge): a pre-edge region (−250 to −30 eV, step size=10 eV, dwell time=0.25 s), the X-ray absorption near edge structure (XANES) region (−30 to +30 eV, step size=0.5 eV, dwell time=0.25 s), and the extended X-ray absorption fine structure (EXAFS) region (to 13 Å$^{-1}$, step size=0.07 Å$^{-1}$, dwell time=1 s). The ionization chambers were optimized for the maximum current with linear response (~10$^{10}$ photons detected/s) with 10% absorption (93% N$_2$ and 7% He) in the incident ion chamber and 70% absorption (50% N$_2$ and 50% Ar) in the transmission detector. A Cu foil spectrum (edge energy=8979.0 eV) was acquired simultaneously with each measurement for energy calibration.

Catalysts were treated in a continuous-flow reactor, constructed of a quartz tube (1 inch OD, 10 inch length) sealed with Kapton windows by two Ultra-Torr fittings. Ball valves were welded to each Ultra-Torr fitting and served as the gas inlet and outlet. An internal K type thermocouple (Omega) was placed against the catalyst sample holder to monitor temperature. Catalyst samples were pressed into a cylindrical sample holder constructed of six wells, forming a self-supporting wafer. The catalyst loading was pre-determined to ensure an absorbance (μx) of approximately 1.0. The catalysts were treated at the indicated temperature in air or $H_2$ and cooled to room temperature before obtaining spectra to minimize contributions due to thermal effects. XANES and EXAFS spectra taken at high temperature (500° C. and 300° C.) were similar to those at RT except for the thermal disorder in the EXAFS. Traces of oxygen and moisture in the He were removed by means of a purifier (Matheson PUR-Gas Triple Purifier Cartridge).

The edge energy of the XANES spectrum was determined from the inflection point in the leading edge, i.e., the maximum in the first derivative of the XANES spectrum. Experimental Cu—O phase shift and back scattering amplitude were obtained from the reference compound copper(II) acetylacetonate ($Cu(acac)_2$; 4 Cu—O at 1.92 Å) and used to fit the data. Background removal and normalization procedures were carried out using standard methods. The coordination parameters were obtained by a least square fit in R-space of the nearest neighbor, $k^2$-weighted Fourier transform data.

Figure 11:
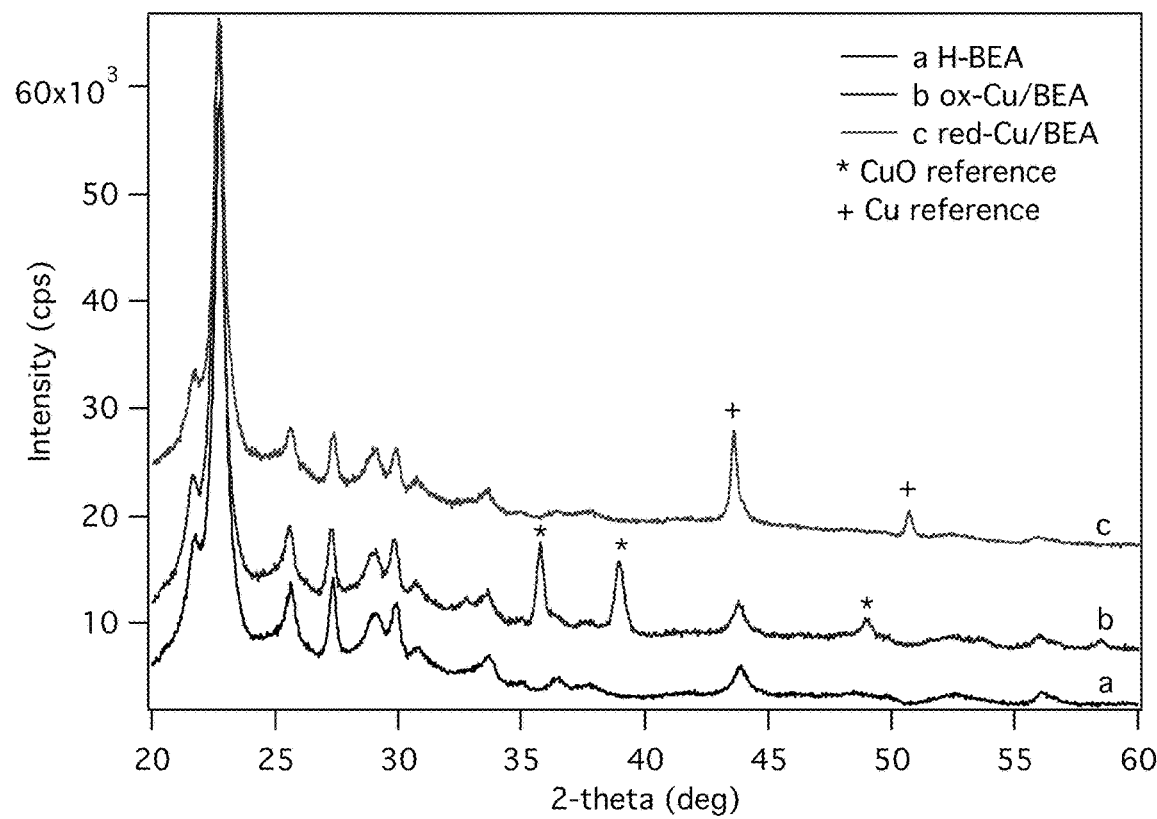
FIG. 11 illustrates powder X-ray diffraction (XRD) patterns for H-BEA, ox-Cu/BEA, and red-Cu/BEA, according to exemplary embodiments of the present invention.
Figure 12:
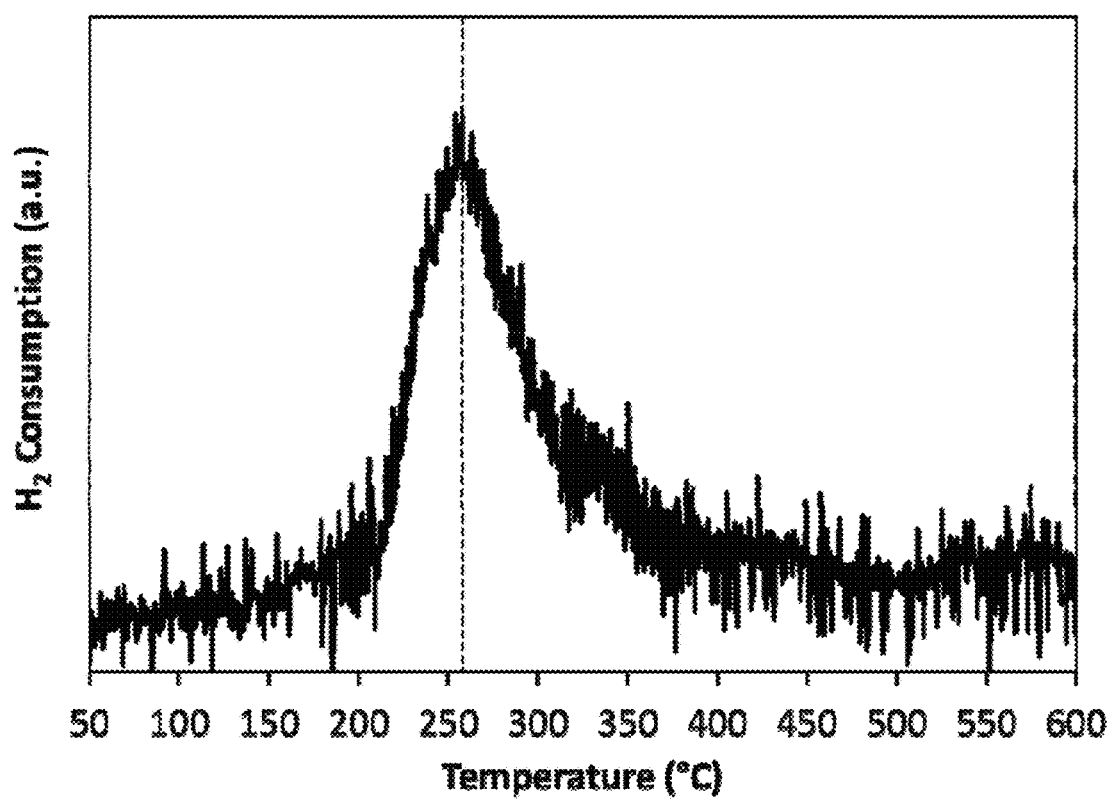
FIG. 12 illustrates the $H_2$ temperature programmed reduction of Cu—$NH_4$—BEA following activation at 500° C. in 1% $O_2$/He, according to exemplary embodiments of the present invention.
Figure 13A:
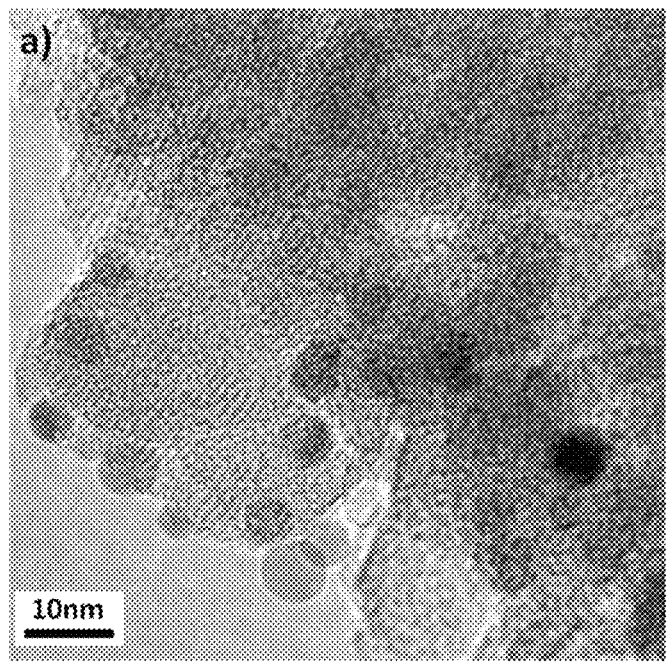
FIGS. 13a and 13b illustrate transmission electron microscopy (TEM) images of red-Cu/BEA illustrating the range of Cu particle sizes, according to exemplary embodiments of the present invention.
Figure 13B:
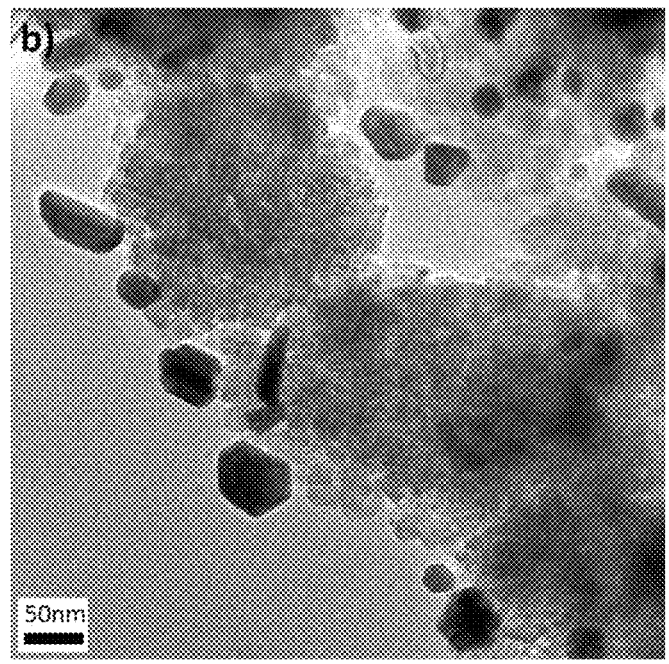

The H-BEA (nomenclature the same as HBEA used elsewhere in this document) and Cu/BEA catalysts were characterized using a variety of bulk and surface sensitive techniques to probe their chemical and structural properties. The bulk crystal structure of H-BEA matched the known reported structure for BEA zeolite, as confirmed by XRD shown in FIG. 11. The addition of Cu resulted in CuO domains (crystallite size of about 30 nm) for ox-Cu/BEA and metallic Cu domains (crystallite size of about 43 nm) for red-Cu/BEA. The formation of large CuO domains upon air oxidation at about 500° C. is due to the high Cu loading and the deposition of Cu via incipient wetness (instead of ion exchange methods). However, it is likely that a small amount of Cu was ion-exchanged into the BEA pores during impregnation. The $H_2$ TPR profile of ox-Cu/BEA showed only one strong peak at approximately ~255° C., attributed to the one-step reduction of CuO to metallic Cu. See FIG. 12. TEM images confirmed the presence of metallic Cu nanoparticles, as shown in FIGS. 13a and 13b. The nanoparticles were poly-disperse with diameters ranging from about 2 nm to about 60 nm.

Figure 14A:
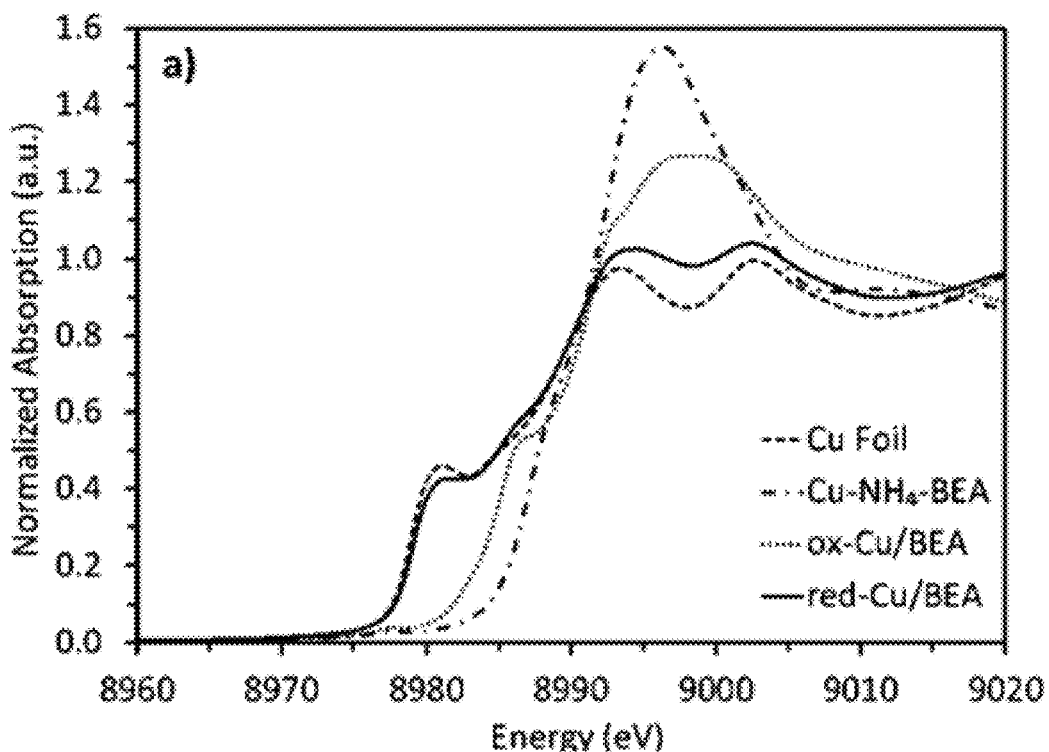
FIGS. 14a and 14b illustrate X-ray absorption spectra (XAS) for as-prepared Cu/BEA following various treatments: (a) X-ray absorption near edge structure (XANES) and (b) extended X-ray absorption fine structure (EXAFS), according to exemplary embodiments of the present invention.
Figure 14B:
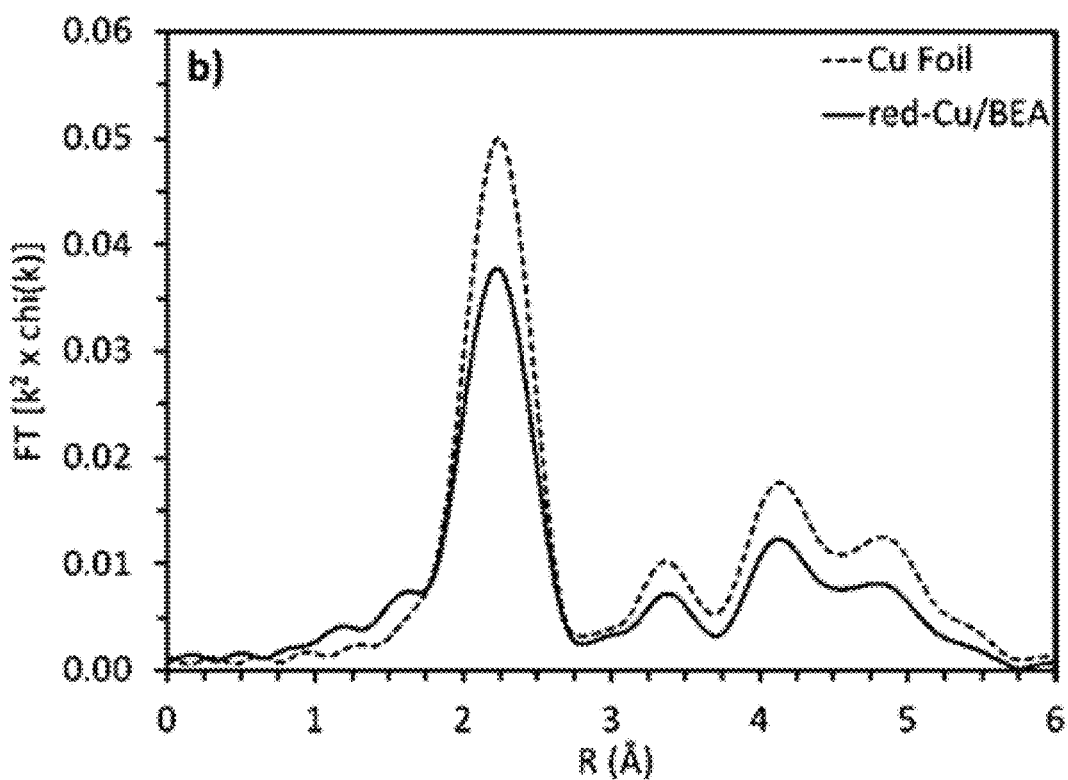

FIGS. 14a and 14b show the XANES spectra collected at the Cu K-edge for the as-synthesized Cu—$NH_4$—BEA in air at room temperature, ox-Cu/BEA, red-Cu/BEA, and Cu foil. The ox-Cu/BEA sample has a small pre-edge feature characteristic of Cu(II), while the edge energy of the red-Cu/BEA catalyst is identical to Cu foil. The XANES spectrum of the reduced sample, however, has a slightly different shape than that of Cu foil consistent with a small fraction of oxidized Cu.

The XANES spectra were fit using a linear combination of Cu(0), Cu(I), and Cu(II) standards to estimate the relative concentrations of each phase. Cu foil was used as the standard for Cu(0), Cu(I)-SSZ-13 (Cu(I)-zeolite) and $Cu_2O$ were used as Cu(I) references, and Cu(II)-SSZ-13 (Cu(II)-zeolite) and CuO were used as Cu(II) references. For ox-Cu/BEA, the best fit was a mixture of CuO and Cu(II)-zeolite with relative concentrations of about 45% and about 55%, respectively. Inclusion of Cu(I) standards gave similar quality fits, but only amounted to less than about 5% Cu(I). For red-Cu/BEA, there was a high fraction of metallic Cu (~86%), but a residual fraction that was unreduced. The best fit suggests that the unreduced portion is a mixture of Cu(I)-zeolite (~4%) and Cu(II)-zeolite (~10%). About 10% of the Cu remained as Cu(II). The presence of Cu(II) in the red-Cu/BEA sample is likely due to the low concentration of ion-exchanged Cu (the fraction of Cu present as Cu(II) in the red-Cu/BEA sample corresponds to about 8% of the ion exchange capacity of the parent $NH_4$—BEA).

The $k^2$-weighted magnitude of the Fourier transform of the red-Cu/BEA was evaluated along with Cu foil. In the region typical of Cu—O bonds (i.e., ~1.7 Å), there was a small feature; however, this feature was too small to fit directly since the scattering from metallic Cu is much larger than that of Cu—O. In order to fit the Cu—O contribution, the Cu—Cu coordination was first determined (9.5 at 2.54 Å). By scaling chi from the Cu foil to the Cu—Cu coordination number in the catalyst, the metallic Cu scattering was subtracted from the red-Cu/BEA spectrum leaving only the Cu—O scattering contribution. The Cu—O coordination number was determined to be about 1.3 with a bond distance of 1.92 Å. The presence of oxidized Cu and the low Cu—O coordination number suggests the presence of ion-exchanged Lewis acidic cationic Cu.

Figure 15A:
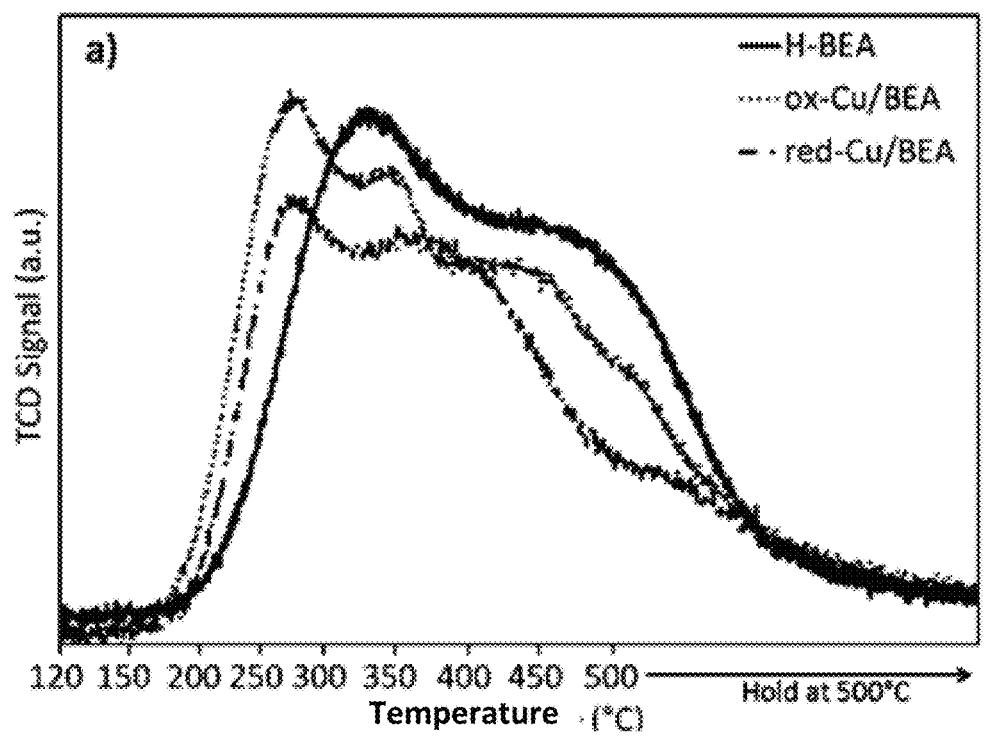
FIGS. 15a and 15b summarize surface acidity characterization for the H-BEA, ox-Cu/BEA, and red-Cu/BEA catalysts using (a) $NH_3$-temperature programmed desorption (TPD) and (b) pyridine diffuse reflectance infrared Fourier transform spectroscopy (py-DRIFTS), according to exemplary embodiments of the present invention.

Acid site densities for these catalysts were determined by $NH_3$-TPD (see FIG. 15a) and are summarized in Table 2.

TABLE 2

Acidity results based on $NH_3$-TPD and py-DRIFTS.

| Catalyst | Total Acid Sites[a] (μmol/g) | Brønsted/ Lewis Ratio[b] | Brønsted Acid Sites (μmol/g) | Lewis Acid Sites (μmol/g) | $NH_3$ Desorption Peak Temperature (° C.) | | | |
|---|---|---|---|---|---|---|---|---|
| | | | | | 1 | 2 | 3 | 4 |
| H-BEA | 1642 | 16.8 | 1550 | 92 | 334 | 470 | — | — |
| ox-Cu/BEA | 2058 | 0.6 | 772 | 1286 | 277 | 342 | 427 | 500[c] |
| red-Cu/BEA | 1918 | 2.3 | 1337 | 581 | 275 | 371 | 500[c] | — |

[a]Total acid site density determined from $NH_3$-TPD. Catalyst sample weight after activation procedure was used to normalize the results.
[b]Brønsted/Lewis acid site ratio was determined from py-DRIFTS.
[c]Desorption peak occurred during 30 minute hold at 500° C.

The H-BEA TPD profile exhibited two distinct desorption peaks at about 334° C. and about 470° C., attributed to weak and strong acid sites, respectively. The addition of Cu resulted in an increase in the total number of acid sites and additional features in the TPD profile compared to H-BEA, specifically a low temperature desorption peak at ~275° C. The ox-Cu/BEA profile also exhibited a sharp peak at about 342° C., attributed to the decomposition of a Cu ammonia complex. The lack of this sharp peak for the red-Cu/BEA sample is in agreement with the XAS results, showing that only a small amount of cationic Cu was present for the red-Cu/BEA sample.

Figure 15B:
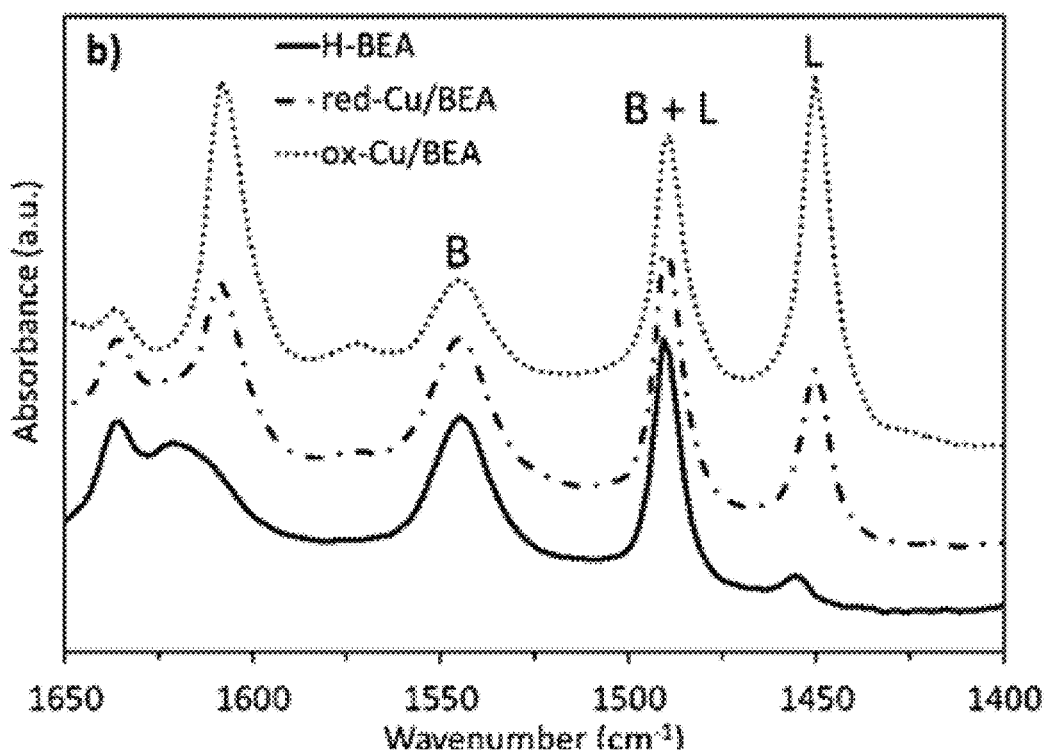

Py-DRIFTS was performed to investigate the acidic character (i.e., Lewis vs Brønsted) of the catalysts. FIG. 15b presents the IR spectra ranging from about 1400 cm$^{-1}$ to about 1650 cm$^{-1}$ for H-BEA, ox-Cu/BEA, and red-Cu/BEA after adsorption of pyridine at about 150° C. followed by purging with Ar. The peaks at 1545 cm$^{-1}$, 1490 cm$^{-1}$, and ~1450 cm$^{-1}$ correspond to pyridine bound to Brønsted sites, Brønsted and Lewis sites, and Lewis sites, respectively. By comparing the integrated area of the peaks at 1545 cm$^{-1}$ and 1450 cm$^{-1}$, the relative ratio of Brønsted to Lewis sites can be determined. The Brønsted/Lewis ratios for H-BEA, ox-Cu/BEA, and red-Cu/BEA were ~16.8, ~0.6, and ~2.3, respectively. The addition of Cu decreased the density of Brønsted sites compared to H-BEA, due to conversion of Brønsted sites into Lewis sites by ion-exchanged Cu and pore blocking by large CuO and Cu domains. A small peak at about 1575 cm$^{-1}$ was also observed for the Cu-containing samples (more prominent for ox-Cu/BEA), and is attributed to pyridine adsorption to a Cu(II)-OH site. Cu provided an additional Lewis site (~1608 cm$^{-1}$), weaker than tetrahedral-Al(III) (~1635 cm$^{-1}$) and comparable in strength to octahedral-Al(III) (~1612 cm$^{-1}$). The intensity of this Cu-based Lewis site at about 1608 cm$^{-1}$ decreased after reduction, consistent with Brønsted/Lewis ratios determined from peak area integrations at 1545 cm$^{-1}$ and 1450 cm$^{-1}$. These results demonstrate the significant increase in Lewis acidity with the presence of Cu, suggesting Cu(I) or Cu(II) sites, which is in good agreement with the NH$_3$ TPD and XAS fits.

Example 2: Cu/BEA Catalyst for the Conversion of DME to C$_4$-C$_9$ Linear and Branched Olefin and Paraffin Fuels-DME Conversion to C$_1$-C$_9$ Linear and Branched Olefin and Paraffin Production Catalytic Measurements Catalyst powders (~0.6 g) were diluted with low surface area, inert silicon carbide in a mass ratio of about 1:6 catalyst:diluent to prevent channeling, avoid problems with axial dispersion, and minimize temperature gradients in the bed. The catalysts were loaded into a stainless steel tubular packed bed reactor, and positioned within the isothermal zone using quartz chips and quartz wool. A four-point thermocouple positioned within the catalyst bed was used to monitor reaction temperature. Reaction temperature during an experiment was maintained within ±0.5° C. of the set point. Prior to reaction rate measurements, the catalysts were activated by ramping from room temperature to 500° C. at about 2° C./min in flowing dry air at about 150 mL min$^{-1}$ g$_{cat}^{-1}$ and holding at 500° C. for about 10 hours. For the red-Cu/BEA catalyst, the sample was cooled to 300° C. in inert gas following air activation at 500° C., and then exposed to H$_2$ flowing at about 150 mL min$^{-1}$ g$_{cat}^{-1}$. The catalyst was held at 300° C. in H$_2$ for about 5 hours before cooling to the reaction temperature. A physical mixture of ~5% Cu/SiO$_2$ and NH$_4$BEA (~0.3 g of each material) was also tested (denoted H-BEA-Cu/SiO$_2$), and was activated using the same procedure as the red-Cu/BEA catalyst.

All reactions were performed at 200° C. and atmospheric pressure, and DME conversion was maintained below about 20%. Two feed mixtures were tested: (1) about 7.1 mL/min DME and about 4.9 mL/min Ar (~60 mol % DME and ~40 mol % Ar) and (2) about 7.1 mL/min DME, about 7.1 mL/min H$_2$, and about 1 mL/min Ar (~47 mol % DME, ~47 mol % H$_2$, and ~6 mol % Ar). Single-component gases were fed to the reactor via calibrated Brooks thermal mass flow controllers. Reactor inlet and outlet gases were sampled through heated (170° C.) lines to an Agilent 7890 GC equipped with a flame ionization detector for analysis of oxygenates and hydrocarbons and two thermal conductivity detectors for analysis of permanent gases and water. GC responses for reactants and products were calibrated using Scott Master Class gas standards and gravimetrically-prepared liquid standards. The effluent was sampled about every 45 min. Catalyst performance was evaluated solely from inlet flow and GC measurements using Ar as an internal standard. Hydrocarbon production rates were normalized by the total number of acid sites as determined by NH$_3$-TPD.

The catalytic performance of ox-Cu/BEA, red-Cu/BEA, and a physical mixture of Cu/SiO$_2$ with H-BEA (H-BEA-Cu/SiO$_2$) was compared to the parent H-BEA, with the results summarized in FIGS. 16a-d. The initial C—C bond formation for DME homologation may be facilitated by trace amounts of hydrocarbon (i.e., olefin) contaminants in the DME feed. The C$_1$-C$_7$ hydrocarbon production rate for H-BEA was similar with and without H$_2$ co-feed (FIG. 4a). At 1.6 hours time on stream (TOS), the H-BEA catalyst exhibited a hydrocarbon production rate of ~827 μmol C mol$_{site}^{-1}$ s$^{-1}$. The red-Cu/BEA catalyst without H$_2$ in the feed exhibited a slightly lower hydrocarbon production rate than H-BEA, while ox-Cu/BEA without H$_2$ showed no detectable hydrocarbon production. However, when H$_2$ was included in the feed, the production rate for red-Cu/BEA was ~2 times greater than H-BEA on both a gravimetric and per site basis (~1689 μmol C mol$_{site}^{-1}$ s$^{-1}$ at 1.5 h TOS). A similar increase in performance was also observed for the physical mixture of Cu/SiO$_2$ and H-BEA, suggesting that metallic Cu may be responsible for the improved production rate. In further support, the presence of H$_2$ for ox-Cu/BEA resulted in an increase in hydrocarbon productivity between 1-3 h TOS (achieving rates similar to red-Cu/BEA), likely due to reduction of CuO to metallic Cu.

Figure 16A:
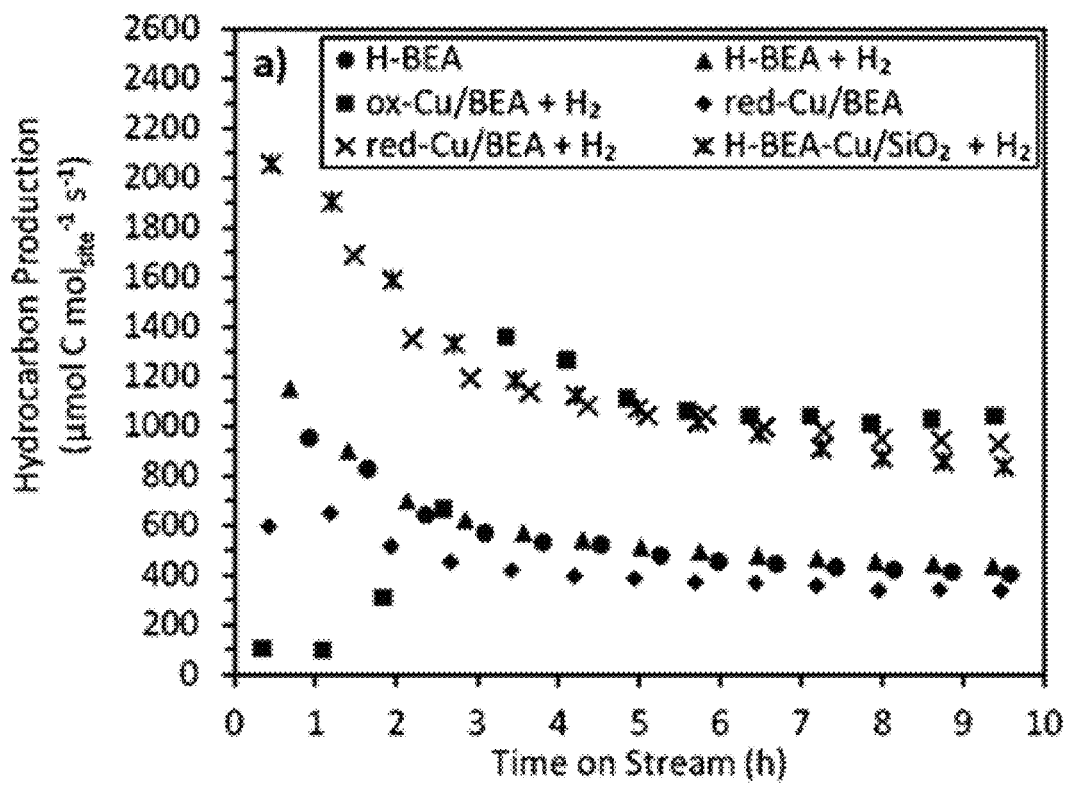
FIGS. 16a-d illustrate DME homologation rates and product selectivities, (a) hydrocarbon production rates, (b) methanol-free carbon selectivities at 6 h time on stream (TOS), (c) $C_7$ paraffin/olefin molar ratios, and (d) percent difference in $C_4$-$C_7$ paraffin/olefin molar ratios compared to H-BEA at 6 hours TOS, according to exemplary embodiments of the present invention.
Figure 16B:
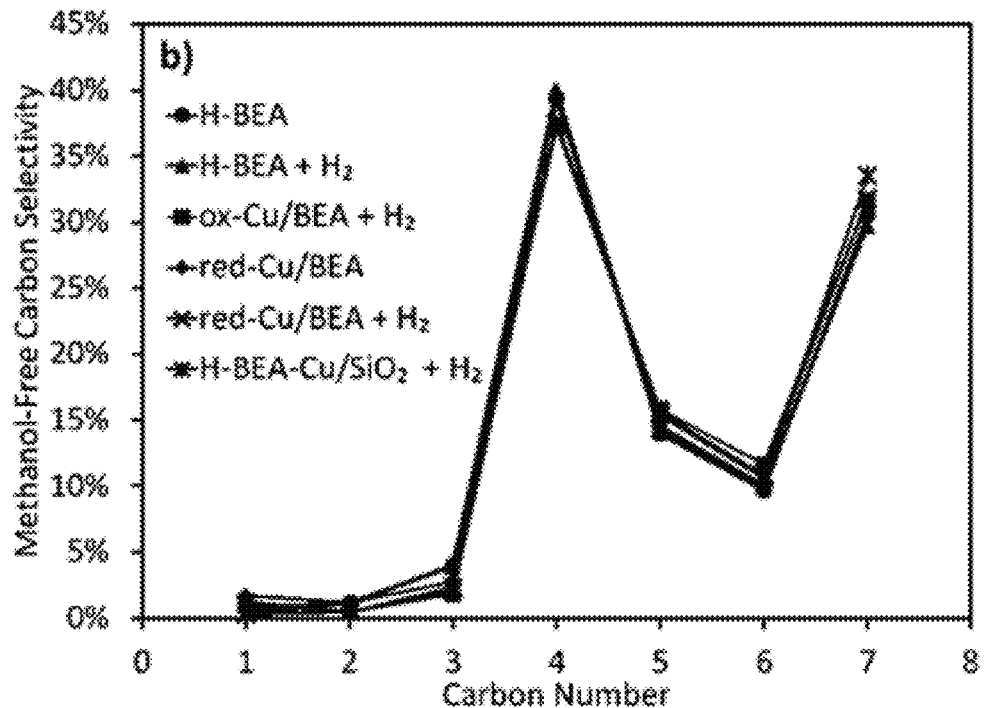
Figure 16C:
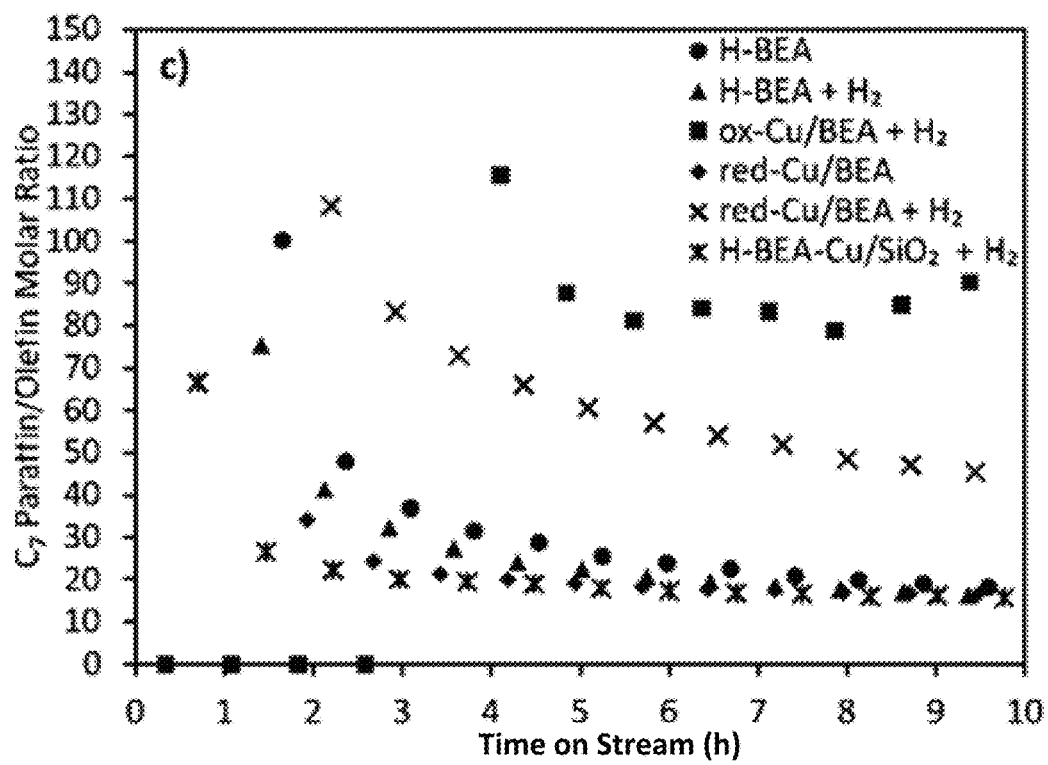
Figure 16D:
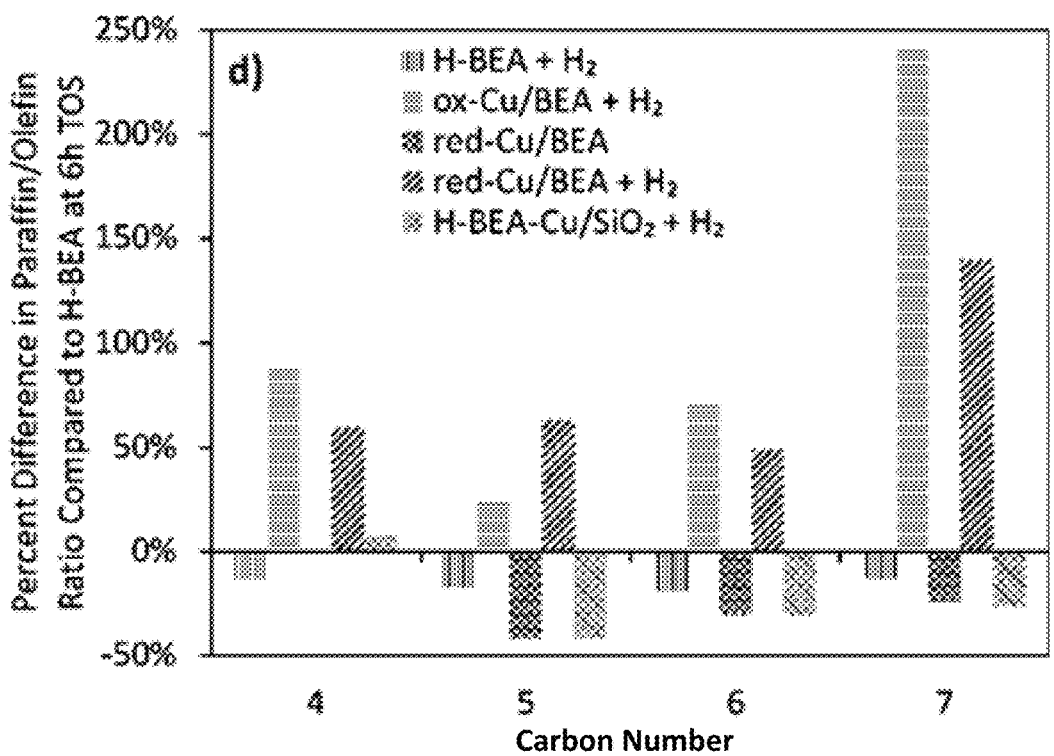
Figure 17A:
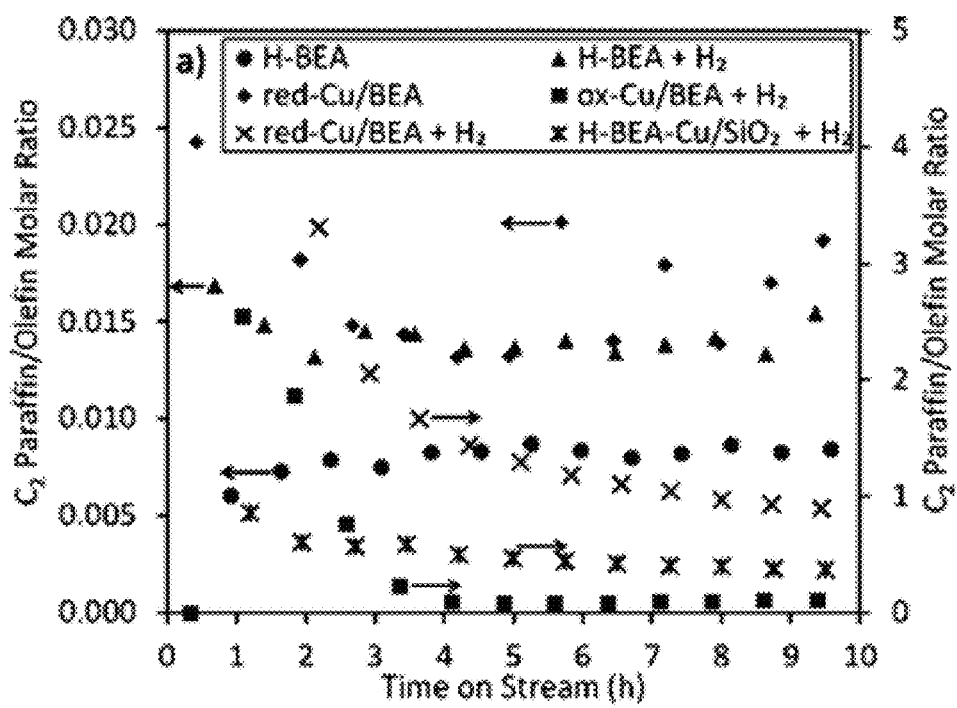
FIGS. 17a-e illustrate paraffin/olefin molar ratios for (a) $C_2$, (b) $C_3$, (c) $C_4$, (d) $C_5$, and (e) $C_6$ hydrocarbons as a function of TOS, according to exemplary embodiments of the present invention.
Figure 17B:
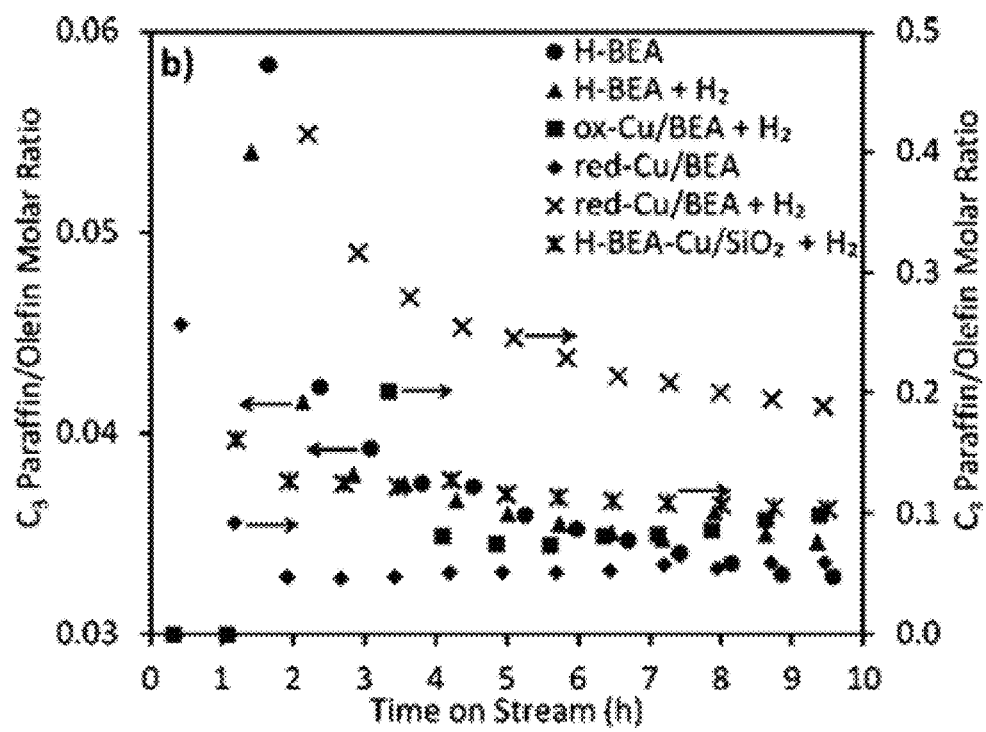
Figure 17C:
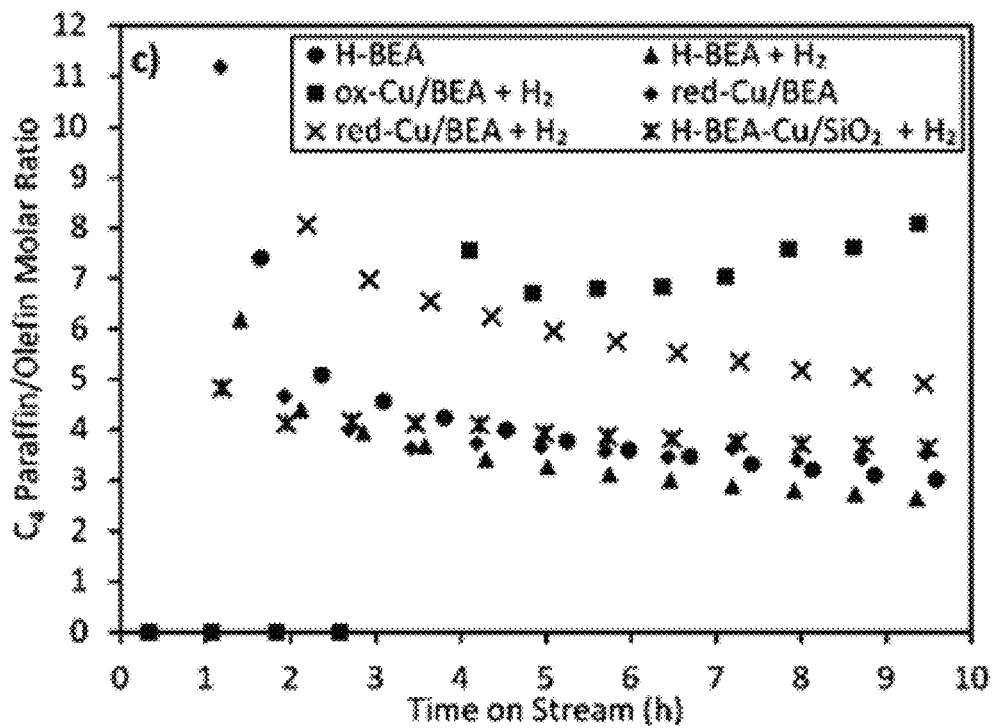
Figure 17D:
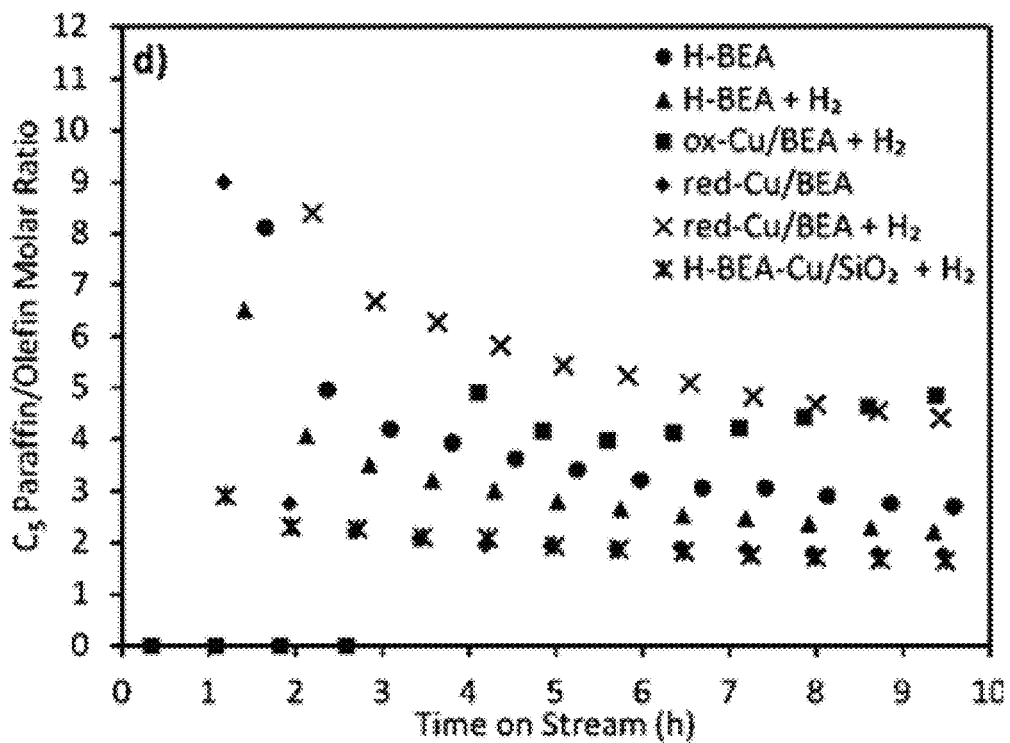
Figure 17E:
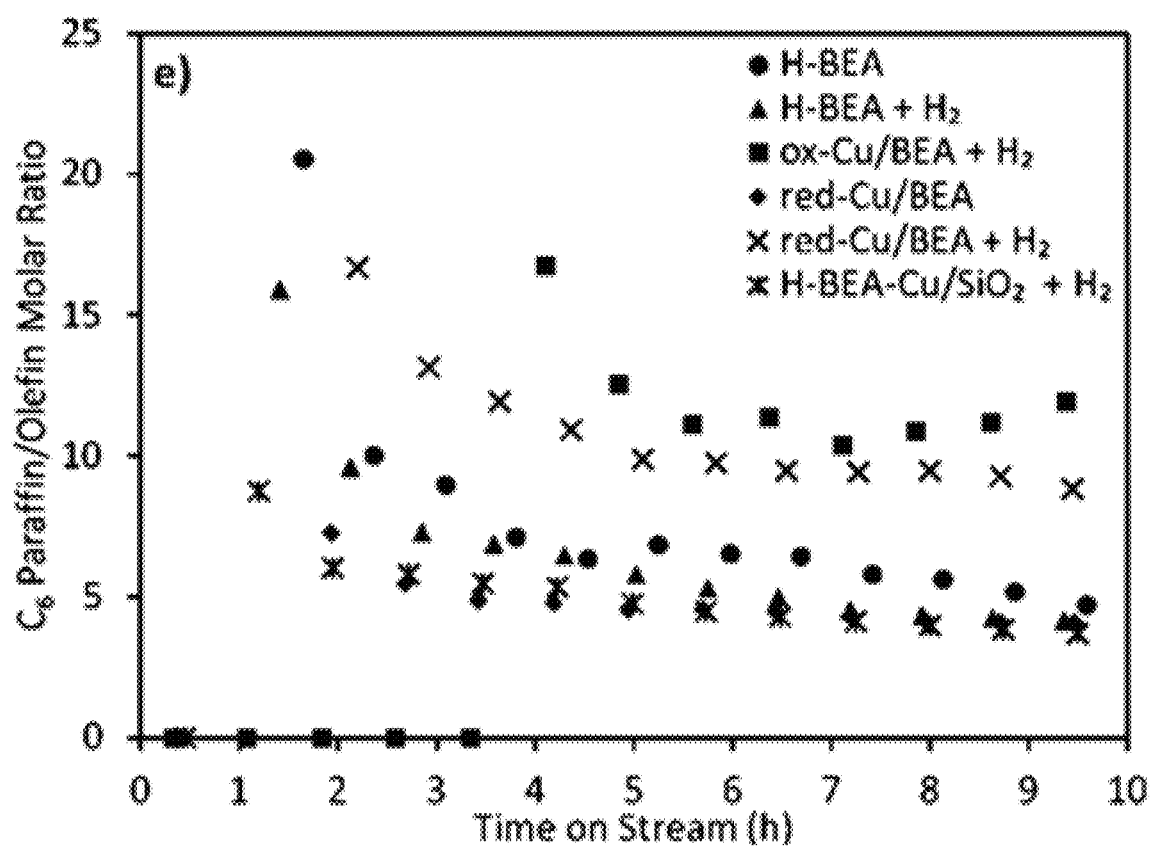
Figure 18A:
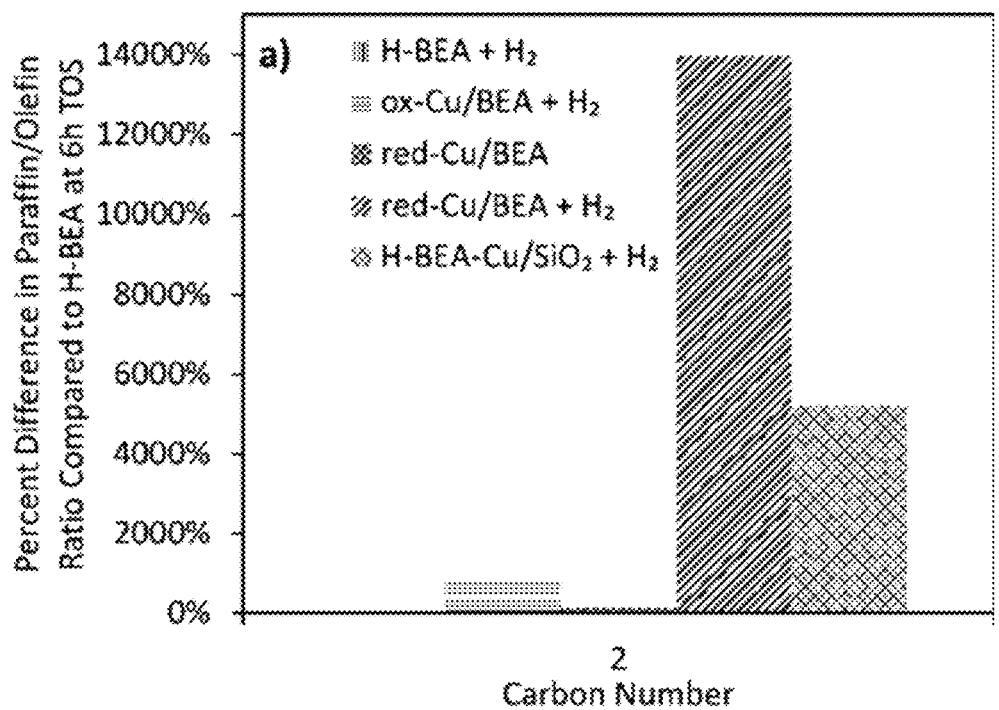
FIGS. 18a-b illustrate percent difference in paraffin/olefin molar ratios compared to H-BEA at 6 h TOS for (a) $C_2$ and (b) $C_3$, according to exemplary embodiments of the present invention.
Figure 18B:
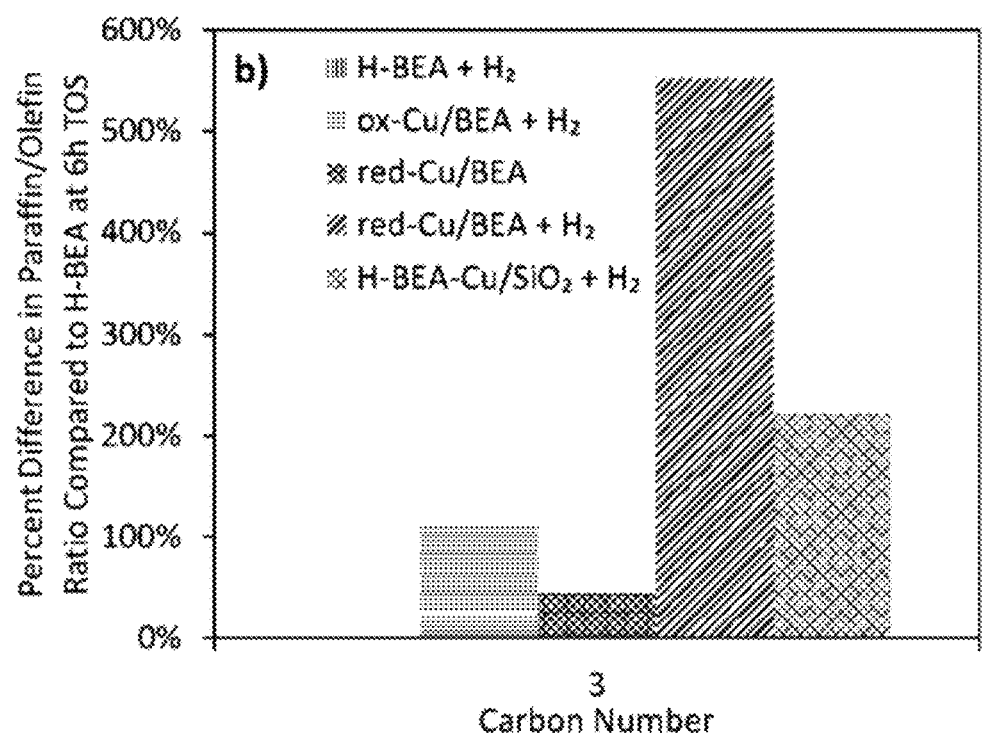

The significant increase in productivity for the red-Cu/BEA catalyst in the presence of H$_2$ appeared to have a negligible effect on the methanol-free carbon selectivity, as shown in FIG. 16b. High selectivity was achieved to both C$_4$ and C$_7$ hydrocarbons. The C$_7$ selectivities at ~6 h TOS for H-BEA, H-BEA+H$_2$, ox-Cu/BEA+H$_2$, red-Cu/BEA, red-Cu/BEA+H$_2$, and H-BEA-Cu/SiO$_2$+H$_2$ were 31%, 30%, 32%, 30%, 32%, and 33%, respectively (error on measurements is ±1%). H$_2$ co-feed also had minimal effect on the product selectivity of H-BEA. However, Cu-containing catalysts modified the degree of product saturation compared to H-BEA, as shown in FIGS. 16c and 16d. The C$_7$ paraffin/olefin molar ratio over red-Cu/BEA+H$_2$ (and ox-Cu/BEA+H$_2$ after 3 h TOS) was more than 2.5 times greater than that of H-BEA (FIG. 16c). Interestingly, the physical mixture of H-BEA and Cu/SiO$_2$ behaved similarly to H-BEA, suggesting minimal hydrogenation of triptene and other C$_7$ olefins by metallic Cu supported on SiO$_2$. In general, the red-Cu/BEA catalyst with H$_2$ co-feed yielded products with significantly increased paraffin/olefin ratios for all carbon numbers compared to H-BEA (see FIGS. 16d, FIGS. 17a-e, and FIGS. 18a-b). The physical mixture of H-BEA and Cu/SiO$_2$ did increase paraffin/olefin ratios over H-BEA, but only for C$_2$ and C$_3$ hydrocarbons. These results suggest that (1) metallic Cu performs olefin hydrogenation of ethylene and propylene primarily, (2) the increased selectivity towards paraffins for C$_4$-C$_7$ hydrocarbons over red-Cu/BEA+H$_2$ was due to either close proximity of the metallic Cu to the BEA zeolite active site and/or the presence of cationic Cu within the BEA pores, and (3) the increased hydrocarbon production rate for red-Cu/BEA+$H_2$ and H-BEA-Cu/$SiO_2$+$H_2$ is related to the increase in paraffin/olefin ratio for $C_2$ and $C_3$ hydrocarbons.

Figure 19:
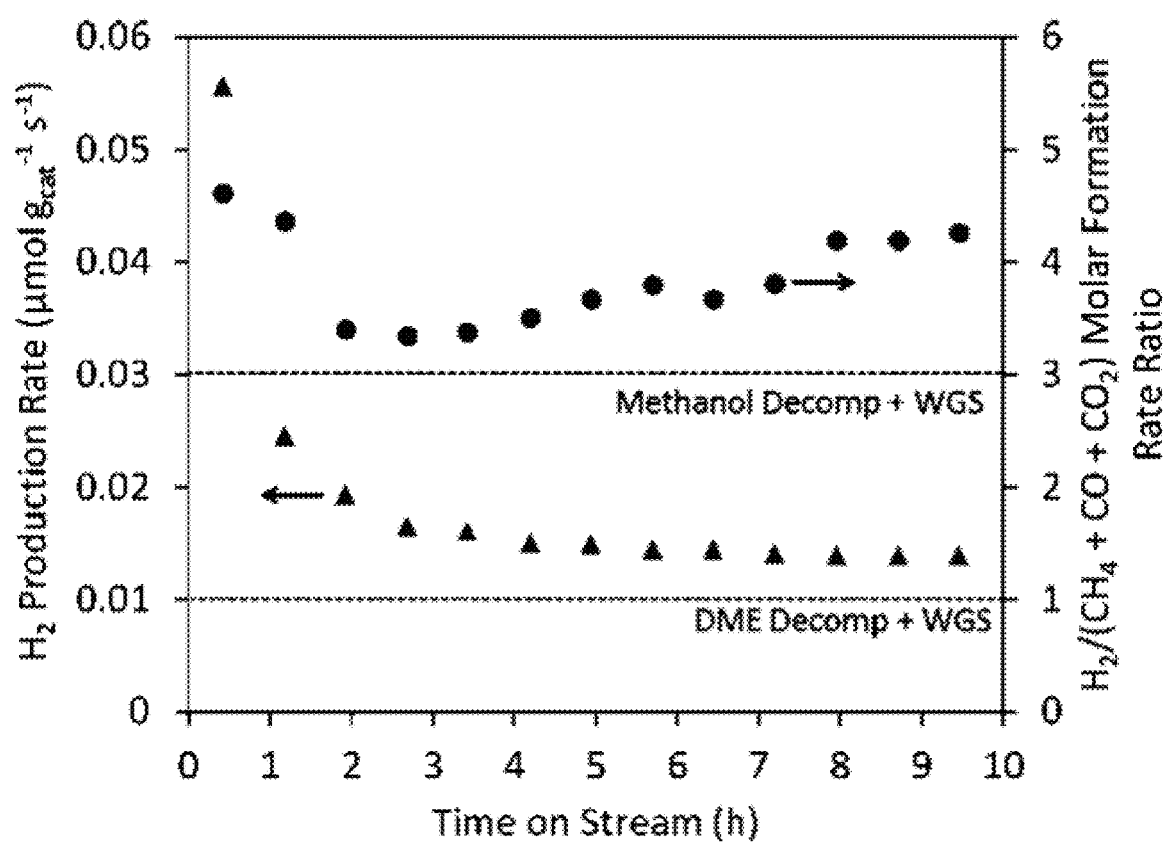
FIG. 19 illustrates $H_2$ production rate and $H_2/(CH_4+CO+CO_2)$ molar formation rate ratio as a function of TOS for a red-Cu/BEA experiment, where the dashed lines correspond to the maximum $H_2/(CH_4+CO+CO_2)$ values achievable based on only methanol decomposition-Water Gas Shift (WGS) or only DME decomposition-WGS, according to exemplary embodiments of the present invention.

Without $H_2$ in the feed, red-Cu/BEA demonstrated a higher selectivity towards $C_5$-$C_7$ olefins compared to H-BEA (FIGS. 16c and 16d, and FIGS. 17a-e). The paraffin/olefin ratio over red-Cu/BEA for $C_5$, $C_6$, and $C_7$ hydrocarbons at 6 hours TOS decreased by 41%, 31%, and 24% compared to H-BEA, respectively. Additionally, $H_2$ production was observed during DME homologation over red-Cu/BEA, as shown in FIG. 19. No $H_2$ production was observed over H-BEA. The production of $H_2$ could occur via DME/methanol decomposition over metallic Cu or alkane dehydrogenation over Lewis acidic cationic Cu sites. The decomposition of DME may result in the formation of $H_2$, $CH_4$, and CO at a stoichiometry of 1:1:1, whereas the decomposition of methanol may produce $H_2$ and CO at a stoichiometry of 2:1. However, since metallic Cu is an active water-gas shift (WGS) catalyst and water is produced as a product of DME homologation, CO could also undergo WGS to produce $CO_2$ and $H_2$. Thus, assuming that $H_2$ is being produced only via decomposition and WGS, the maximum attainable value for a ratio of the molar formation rates of $H_2$/($CH_4$+CO+$CO_2$) would be about 3 for only methanol decomposition combined with WGS and about 1 for only DME decomposition combined with WGS (corresponding to the dashed lines in FIG. 19). The $H_2$/($CH_4$+CO+$CO_2$) molar formation rate ratio is shown in FIG. 19 for red-Cu/BEA, and the values were greater than about 3 throughout the experiment. The high concentration of DME in the feed and the increase in $CH_4$ selectivity observed for red-Cu/BEA (FIG. 16b; ~1.7% for red-Cu/BEA vs. ~0.7% for H-BEA) suggest that DME decomposition likely contributed to more $H_2$ production than methanol decomposition. These results suggest that, while methanol/DME decomposition was occurring during DME homologation over red-Cu/BEA, it was not the only source of $H_2$ production; alkane dehydrogenation was likely also occurring.

Figure 20:
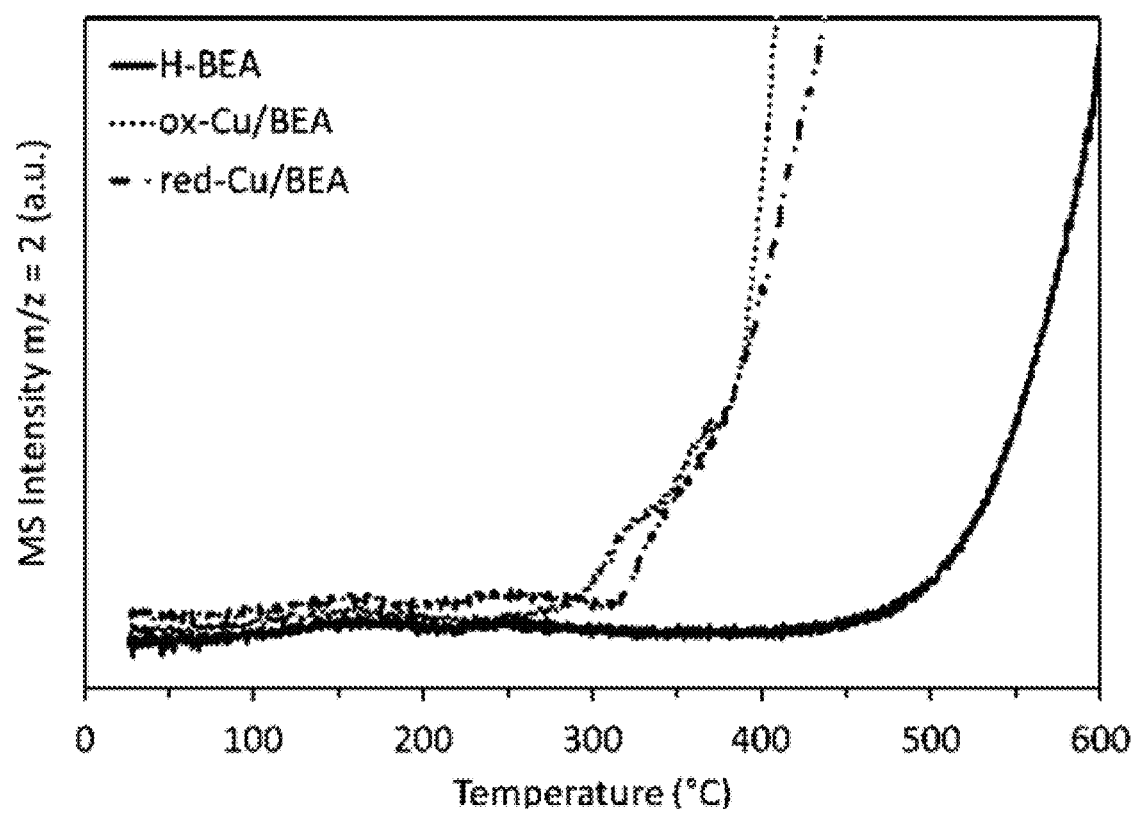
FIG. 20 illustrates $H_2$ (m/z=2) evolution during isobutane dehydrogenation experiments for H-BEA, ox-Cu/BEA, and red-Cu/BEA, according to exemplary embodiments of the present invention.

Temperature programmed reactions with isobutane were performed to test the dehydrogenation activity of the H-BEA, ox-Cu/BEA, and red-Cu/BEA catalysts, and the results are provided in FIG. 20 $H_2$ evolution over H-BEA did not occur until ~500° C., whereas it was observed in for temperatures ranging from about 275° C. to about 300° C. for ox-Cu/BEA and red-Cu/BEA. The only products observed were $H_2$ and isobutylene. The similarity of the $H_2$ evolution onset temperature for ox-Cu/BEA and red-Cu/BEA suggests that cationic Cu sites were responsible for the dehydrogenation, not metallic sites.

Alkane dehydrogenation requires C—H bond activation (i.e., hydrogen abstraction) and recombinative desorption of hydrogen atoms to form $H_2$. Isobutane dehydrogenation over H-BEA was not observed until approximately 500° C. as shown in FIG. 20. The rate limiting step for alkane dehydrogenation over zeolites is believed to be hydrogen recombination. These results suggest that cationic Cu species catalyze recombinative hydrogen desorption. Thus, for DME homologation over red-Cu/BEA without co-fed $H_2$, hydrogen abstracted from branched alkanes can either be transferred to alkoxides on the zeolite surface via a bimolecular hydride-transfer step or recombine and desorb on cationic Cu species. As this result supports the formation of cationic Cu—$H_x$ or $CuO_x$—H species under reaction conditions, co-fed $H_2$ likely dissociates on these cationic Cu species, resulting in hydrogenation of olefins or hydrogen transfer to surface alkoxides. This proposed phenomenon agrees with the trend in paraffin/olefin ratios observed for red-Cu/BEA+$H_2$ compared to H-BEA-Cu/$SiO_2$+$H_2$ (FIGS. 16d and FIGS. 18a-b), which suggests that cationic Cu species are required to achieve an increase in $C_4$-$C_7$ paraffin/olefin ratios.

Figure 21:
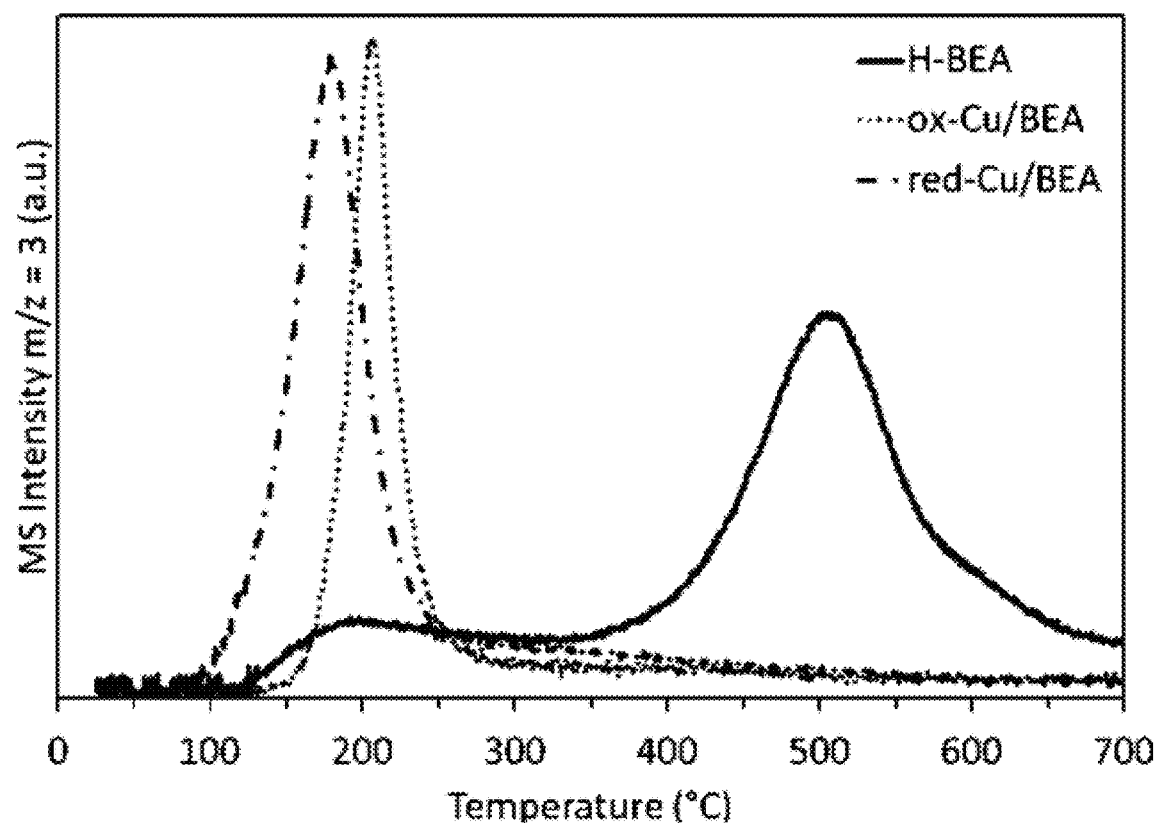
FIG. 21 illustrates HD (m/z=3) evolution during H-D (hydrogen-deuterium) exchange experiments for H-BEA, ox-Cu/BEA, and red-Cu/BEA, according to exemplary embodiments of the present invention.

Due to the significant increases in productivity and paraffin selectivity for red-Cu/BEA+$H_2$, experiments probing the activation of $H_2$ over H-BEA, ox-Cu/BEA, and red-Cu/BEA using H-D exchange experiments were completed. FIG. 21 shows the evolution of HD during isotopic exchange of $D_2$ with hydrogen atoms over the activated catalysts. The hydrogen comes from —OH groups on the catalyst surface, including Brønsted protons from zeolitic-bridged —OH groups, silanols, or —OH groups at extra-framework Al and Cu atoms (e.g., Cu(II)—OH). The red-Cu/BEA catalyst was capable of activating $D_2$ and evolving HD at a significantly lower temperature than H-BEA. The maximum rate of HD evolution was observed at ~180° C. for red-Cu/BEA and ~500° C. for H-BEA. The ox-Cu/BEA sample also exhibited a low temperature peak for HD evolution (~200° C.); however, $D_2O$ production was also observed at this temperature indicating that CuO particles were reduced to metallic Cu from the $D_2$ in the feed (in agreement with DME homologation results showing an increase in hydrocarbon productivity after 3 hours TOS). The total amount of HD evolved (i.e., the area under the curve) was nearly identical for H-BEA and red-Cu/BEA, suggesting that the $D_2$ activated by the Cu can reach all of the H atoms present within the zeolite. The total amount of HD evolved for ox-Cu/BEA was approximately 65% of that for H-BEA. These results indicate that activated hydrogen is available during DME homologation over red-Cu/BEA for hydrogen transfer or hydrogenation reactions that may occur at defect sites, cationic Cu sites, metallic Cu sites, or on carbonaceous deposits.

Figure 22A:
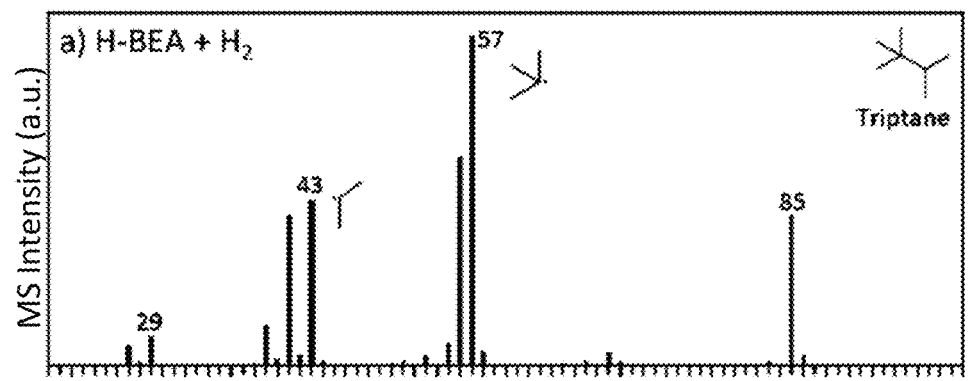
FIGS. 22a-c illustrate mass spectra for triptane collected at 6 hours TOS from (a) H-BEA+$H_2$, (b) H-BEA+$D_2$, and (c) red-Cu/BEA+$D_2$ experiments, according to exemplary embodiments of the present invention.
Figure 22B:
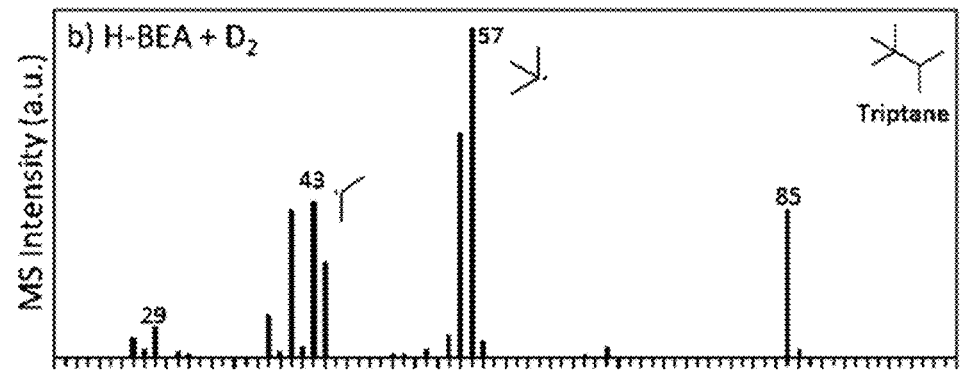
Figure 22C:
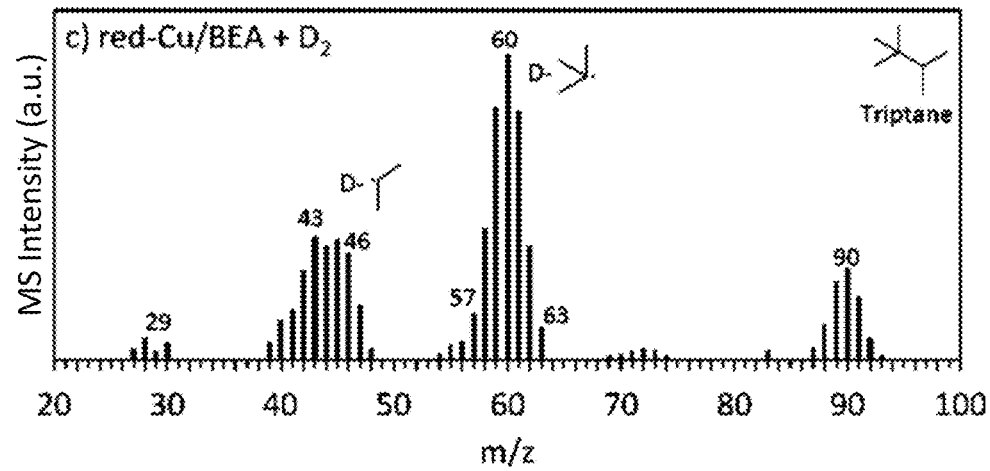
Figure 23A:
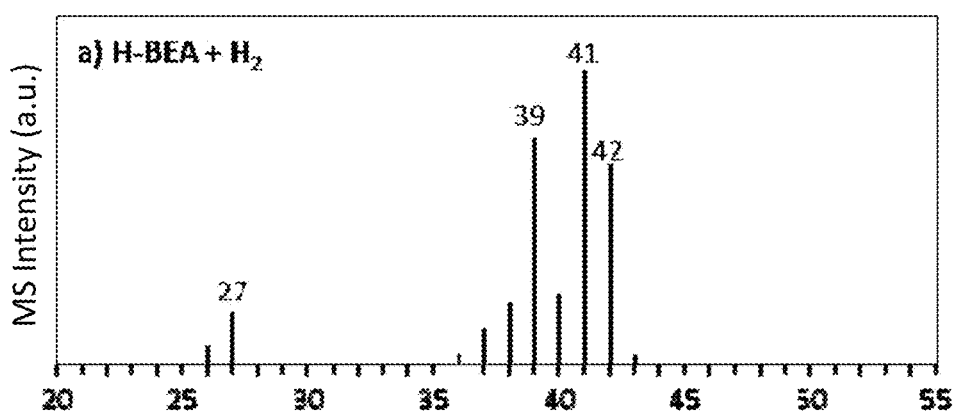
FIGS. 23a-c illustrate mass spectra for propylene collected at 6 hours TOS from a) H-BEA+$H_2$, b) H-BEA+$D_2$, and c) red-Cu/BEA+$D_2$, according to exemplary embodiments of the present invention.
Figure 23B:
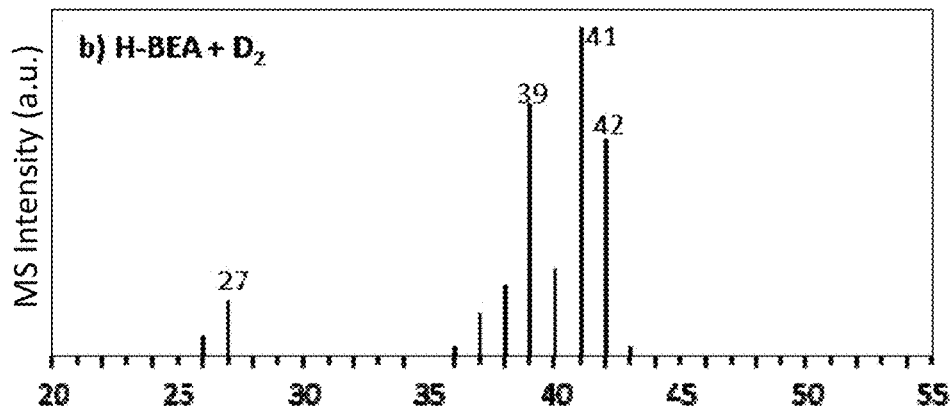
Figure 23C:
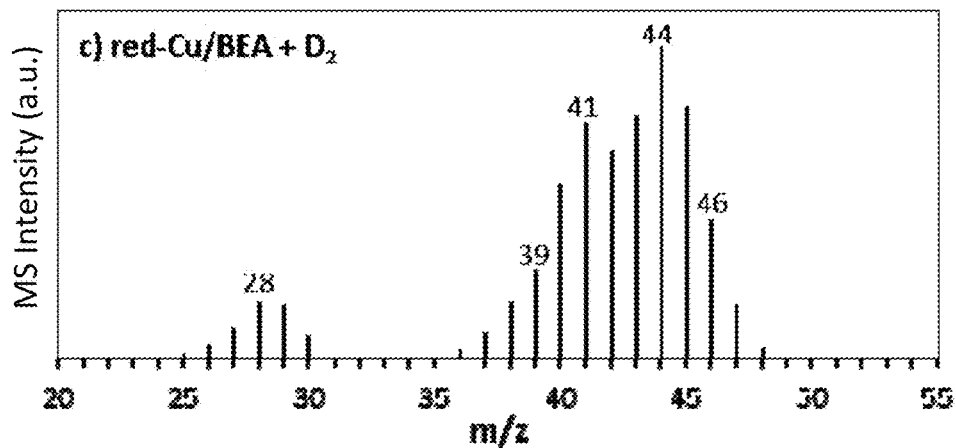
Figure 24A:
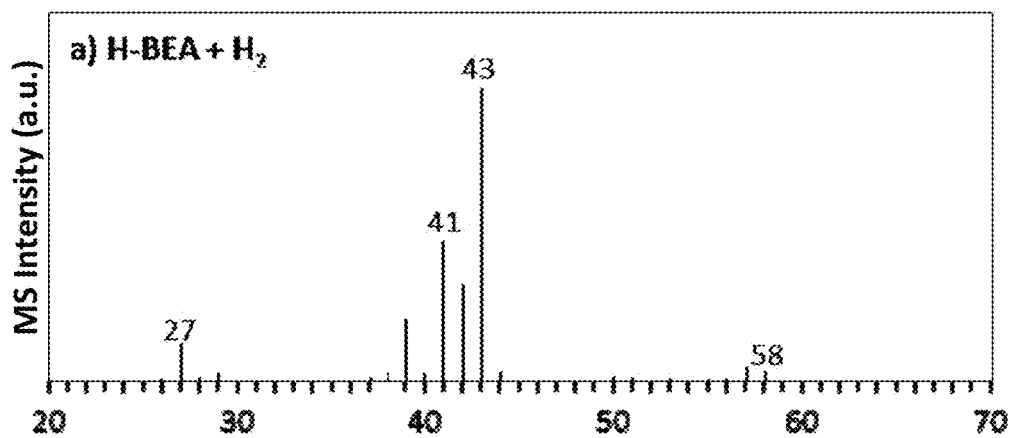
FIGS. 24a-c illustrate mass spectra for isobutane collected at 6 hours TOS from a) H-BEA+$H_2$, b) H-BEA+$D_2$, and c) red-Cu/BEA+$D_2$, according to exemplary embodiments of the present invention.
Figure 24B:
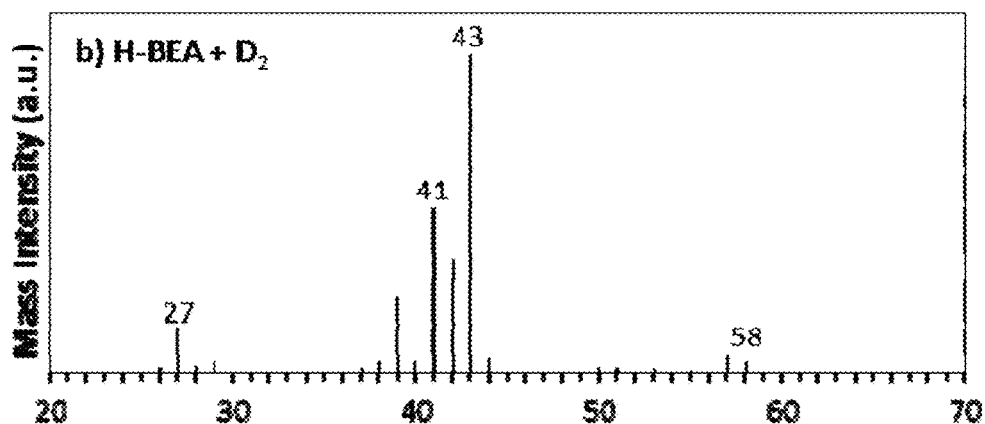
Figure 24C:
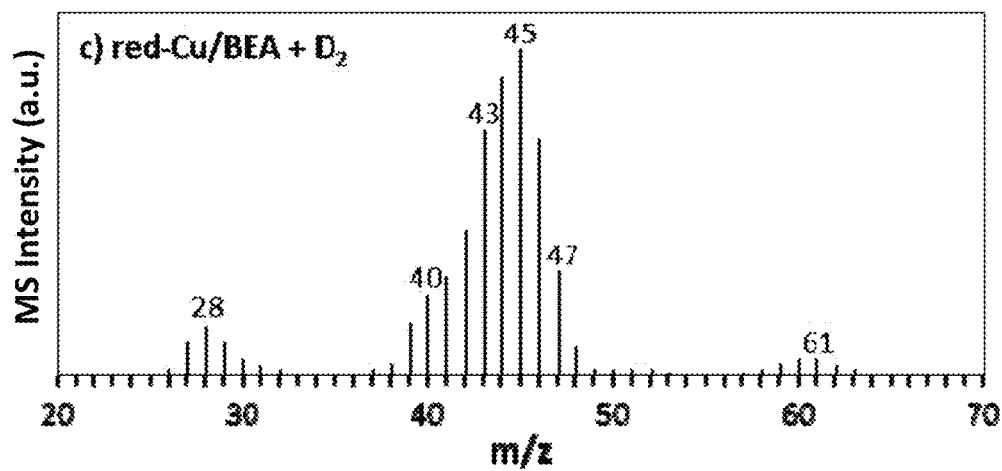
Figure 25:
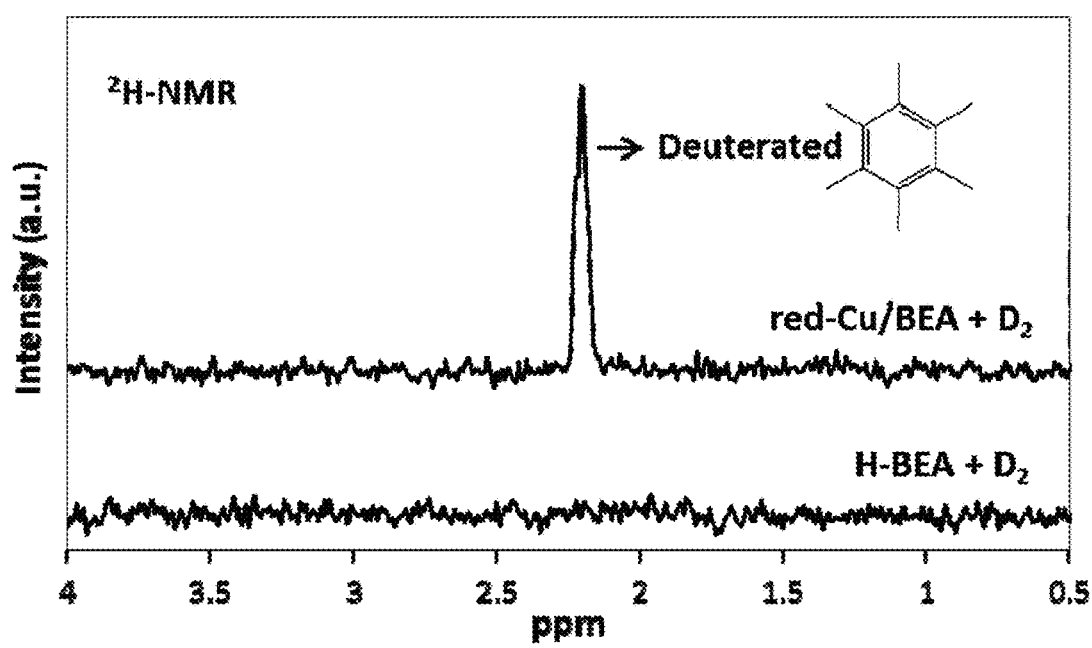
FIG. 25 illustrates $^2$H-Nuclear Magnetic Resonance (NMR) spectra of spent catalyst washing solution for H-BEA+$D_2$ and red-Cu/BEA+$D_2$, according to exemplary embodiments of the present invention.

The activation and incorporation of $H_2$ was further explored through isotopically-labeled experiments. $D_2$ was co-fed with DME over H-BEA and red-Cu/BEA and the incorporation of deuterium into the hydrocarbon products was monitored using mass spectrometry. The mass spectra for triptane collected at 6 hours TOS are shown in FIGS. 22a-c. When $H_2$ is replaced with $D_2$ over H-BEA, there is no change in the resulting mass spectrum for triptane. In contrast, over red-Cu/BEA, significant incorporation of deuterium into the desired product was observed. This deuterium incorporation was observed for all representative products, including HMB (see FIGS. 23a-c, FIGS. 24a-c, and FIG. 25).

As discussed earlier, the direct homologation of DME to alkanes is hydrogen-deficient. The necessary hydrogen atoms are provided by the formation of alkylated aromatic by-products, such as HMB. For the red-Cu/BEA catalyst, hydrogen atoms are provided by the activation of gaseous $H_2$ and are incorporated into the hydrocarbon products, suggesting that the formation of alkylated aromatics may be reduced.

Figure 26:
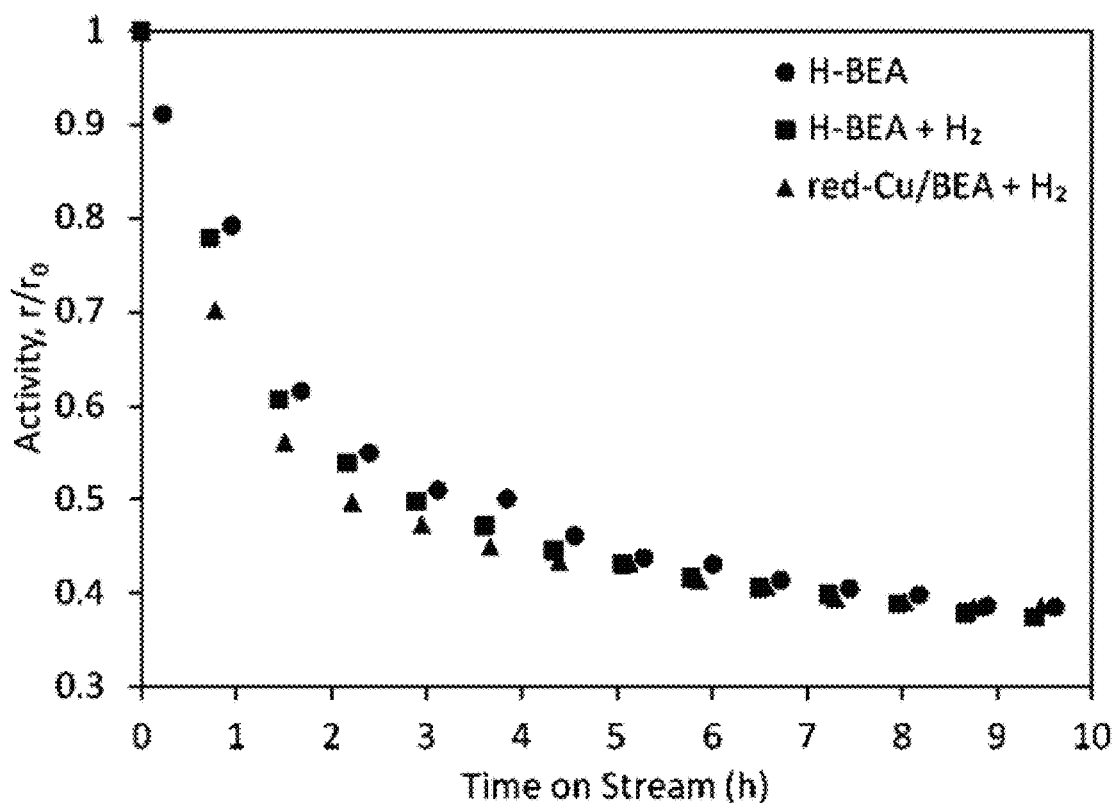
FIG. 26 illustrates deactivation profiles plotted as activity ($r/r_0$) versus TOS for H-BEA, H-BEA+$H_2$, and red-Cu/BEA+$H_2$, according to exemplary embodiments of the present invention.

Table 3 provides the ratios of ethylene and ethane ($C_2$) to 2 MB and the ratio of carbon present in HMB to carbon present in hydrocarbons ($C_{HMB}/C_{HC}$) for the catalysts with and without co-fed $H_2$. Ethane was included with ethylene due to probable olefin hydrogenation over metallic Cu. Calculated at either the same TOS or at the same conversion, red-Cu/BEA+$H_2$ and H-BEA-Cu/$SiO_2$+$H_2$ exhibited lower $C_2$/2 MB ratios than H-BEA, suggesting that the addition of metallic Cu promoted propagation of the olefin cycle. This shift was further confirmed by the $C_{HMB}/C_{HC}$ ratios. Red-Cu/BEA+$H_2$ exhibited a $C_{HMB}/C_{HC}$ ratio of about 0.04 compared to that of about 0.12 for H-BEA. Interestingly, for both the $C_2/2$ MB ratio at 6 hours TOS and the $C_{HMB}/C_{HC}$ ratio, the value for H-BEA was approximately 3 times higher than for red-Cu/BEA+$H_2$, suggesting good agreement between both measurement methods. The decreased HMB production for red-Cu/BEA+$H_2$ is not likely due to hydrogenation of HMB on metallic Cu. As discussed previously, the ox-Cu/BEA+$H_2$ behaved similarly to red-Cu/BEA+$H_2$ as the co-fed $H_2$ resulted in the reduction of CuO to metallic Cu under reaction conditions. The red-Cu/BEA without co-fed $H_2$ exhibited the highest values for $C_2/2$ MB and $C_{HMB}/C_{HC}$ ratios, consistent with previous results showing its increased selectivity towards olefins via dehydrogenation. Although red-Cu/BEA+$H_2$ exhibited a decreased selectivity towards HMB, its deactivation profile was similar to H-BEA (see FIG. 26), suggesting that either (1) formation of alkylated aromatic and poly-aromatic residues is not the primary cause of catalyst deactivation during the initial 10 h TOS or (2) HMB is not a representative surrogate for these heavy aromatic coke precursors. Other possible causes of deactivation include $H_2O$ inhibition and competitive adsorption between DME-derived methoxide species and larger alkoxides.

TABLE 3

Effect of Cu addition on product selectivity.

| Experiment | $r^a_{Ethane+Ethylene}/r_{2-methylbutane(ene)}$ | $r^b_{Ethane+Ethylene}/r_{2-methylbutane(ene)}$ | $C^c_{HMB}/C_{HC}$ |
|---|---|---|---|
| H-BEA | 0.23 | 0.16 | 0.12 |
| H-BEA + $H_2$ | 0.21 | 0.15 | 0.07 |
| ox-Cu/BEA + $H_2$ | 0.08 | 0.07 | 0.03 |
| red-Cu/BEA | 0.24 | 0.24 | 0.14 |
| red-Cu/BEA + $H_2$ | 0.08 | 0.08 | 0.04 |
| H-BEA-Cu/$SiO_2$ + $H_2$ | 0.08 | 0.09 | 0.03 |

[a]Ratio of molar formation rate of ethane and ethylene to molar formation rate of 2-methylbutane and 2- methyl-butenes at 6 h TOS.
[b]Ratio of molar formation rate of ethane and ethylene to molar formation rate of 2-methylbutane and 2-methyl-butenes at a DME conversion of 11% (different TOS).
[c]Ratio of total carbon present in HMB to total carbon in $C_1$-$C_7$ hydrocarbons produced over an entire experiment.

Considering the above results, the red-Cu/BEA catalyst possesses both metallic Cu sites and Lewis acidic cationic Cu sites, and both types of sites appear to affect increases in hydrocarbon productivity, increases in paraffin/olefin ratios, and decreases in selectivity towards aromatics. Based on TEM, a large fraction of the metallic Cu nanoparticles were larger than the diameter of the H-BEA pores, and thus were located on the external surface of the zeolite. Given the comparison to Cu/$SiO_2$, the metallic Cu sites activate $H_2$ at low temperature, decompose some DME into $H_2$, CO, and $CH_4$, and hydrogenate ethylene and propylene. Although $C_2$ and $C_3$ hydrocarbons accounted for less than about 10% of the carbon in the products, the hydrogenation of ethylene and propylene over metallic Cu sites appeared to be directly responsible for both increased hydrocarbon productivity and decreased selectivity towards aromatics, i.e. HMB.

Based on these findings, it appears that the removal of ethylene from the reaction sequence via hydrogenation to ethane may result in an increase in productivity per site because the sites may be more accessible to the larger, more reactive olefins (i.e., ethylene inhibits the reaction as it adsorbs readily, but reacts slowly compared to larger olefins). The decrease in aromatic selectivity may be attributed to a decrease in ethylene and propylene aromatization due to the decreased concentration of these olefins.

The cationic Cu sites had low Cu—O coordination numbers and their XAS spectra resembled those for other Cu ion-exchanged zeolites, suggesting that the cationic Cu of the red-Cu/BEA catalyst was ion-exchanged within the pores of the zeolite. These cationic Cu species clearly introduced significant Lewis acidity based on py-DRIFTS, and these sites catalyzed alkane dehydrogenation (i.e., hydrogen recombinative desorption). These findings suggest the formation of cationic Cu—$H_x$ or $CuO_x$—H species under reaction conditions that can, either independently or in conjunction with a Brønsted acid site, activate C—H bonds, abstract hydrogen, and perform recombinative hydrogen desorption. The dehydrogenation activity of these Cu species suggests that they can facilitate reincorporation of "terminal" alkanes into the chain growth pool during DME homologation via direct dehydrogenation or hydride abstraction and intermolecular hydrogen transfer between an alkane and a surface alkoxide. In the presence of $H_2$, it is proposed that these cationic Cu species activate $H_2$ and either hydrogenate olefins or transfer hydrogen to surface alkoxide species to produce alkanes, as evidenced by the increase in $C_4$-$C_7$ paraffin/olefin ratios for red-Cu/BEA+$H_2$.

Example 3: $C_4$-$C_9$ Linear and Branched Olefin and Paraffin Fuel Conversion to Distillate-Range Hydrocarbon Fuels The catalyst used for this study was Amberlyst-35™ (dry) as supplied by Rohm & Haas. Chemical reagents were purchased from Sigma Aldrich and were used as supplied without any purification. 2-methyl-1-hexene (96%), 2,3,3-trimethyl-1-butene (triptene, 98%), 2,3-dimethyl-1-butene (97%), 2,4,4-trimethyl-1-pentene (96%) and 1-heptene (97%) were used as reactants. N-nonane (≥99%) and pentadecane (≥99%) were used as solvents. Reactions were performed in a 100 $cm^3$ 3-neck round-bottom glass flask that was designed to model a stirred-batch liquid phase reactor. A hot plate was used to heat the flask in the temperature range of 60-100° C. Temperature was measured continuously by a thermometer which was always in contact with the reaction mixture. The contents of the flask were mixed vigorously via a stir bar. The reaction head-space was continuously purged with nitrogen. The flask was connected to a water-cooled condenser to ensure liquid phase conditions and to prevent loss of reactants via vaporization. One of the necks on the glass flask served as a port for online-sampling. All the reactions were carried out at atmospheric pressure.

The coupling reactions to produce a $C_7$+ product were carried out at three different temperatures: 60, 80 and 100° C. For each run, only one olefin was used so that the reaction performance of each olefin could be studied distinctly. The solvents used in the experiments were either nonane or pentadecane. For a typical run, the first step involved mixing the catalyst (used without pre-treatment) in the desired solvent via vigorous stirring in the reaction flask accompanied with heating of the reaction mixture to the desired reaction temperature. Once the desired steady temperature was reached, the reactant was injected into the mixture and immediately after this a small sample was removed manually via a syringe (typically ≤1 mL of reaction mixture per sample). This marked the start of the reaction. This was followed by liquid sampling at different intervals during the reaction. The reaction in the sample volume was stopped by quenching the sealed sample vial in an ice-bath. The contents of the sample were analyzed via an offline Gas Chromatography-Mass Spectrometry (GC-MS). The typical length of one batch-reaction was 220 minutes accompanied with intermittent sampling. The amounts of reagents and catalysts used in a typical batch were 0.5-3.8 g of Amberlyst-35™, 18.5-37.0 ml of the solvent and 2.5-5.0 ml of the reactant. The sample volume was further diluted by 100 times (by volume) using nonane before the GC analysis begins. The stirring speed of 600 rpm (or more) was typically considered sufficient for overcoming any intraparticle mass transfer diffusion limitations in the macroporous resins (Amberlyst-35™).

The concentration of reactants and products in a given sample were calculated based on the area under the FID peak and the FID response factor corresponding to the sample component of interest. Response factors for each reactant and all major products were determined by using standard solutions with known concentrations of different possible reaction batch components. For few compounds ($\geq C_{16}$), response factor was estimated by extrapolating the carbon number-response factor relationship obtained from standard solutions.

The extent of thermal and/or chemical deactivation of catalyst at different conditions was estimated by measuring the change in the density of acid sites after each reaction run using the aqueous phase titration. The effects of olefin length, branching and position of the double bond were also examined by studying the reaction with various olefins having different skeletal structures. The extent of side reactions, like cracking and polymerization, was determined by examining the GC/MS data for different possible products.

Time-based composition data was obtained by analyzing the reaction samples at different times via a GC/MS technique. In typical analysis, 0.2 μL of diluted liquid sample (100-fold dilution) is injected into a Hewlett-Packard GC. The GC is equipped with a capillary column and a mass selective detector. The injector temperature was set to 260° C.

Figure 27:
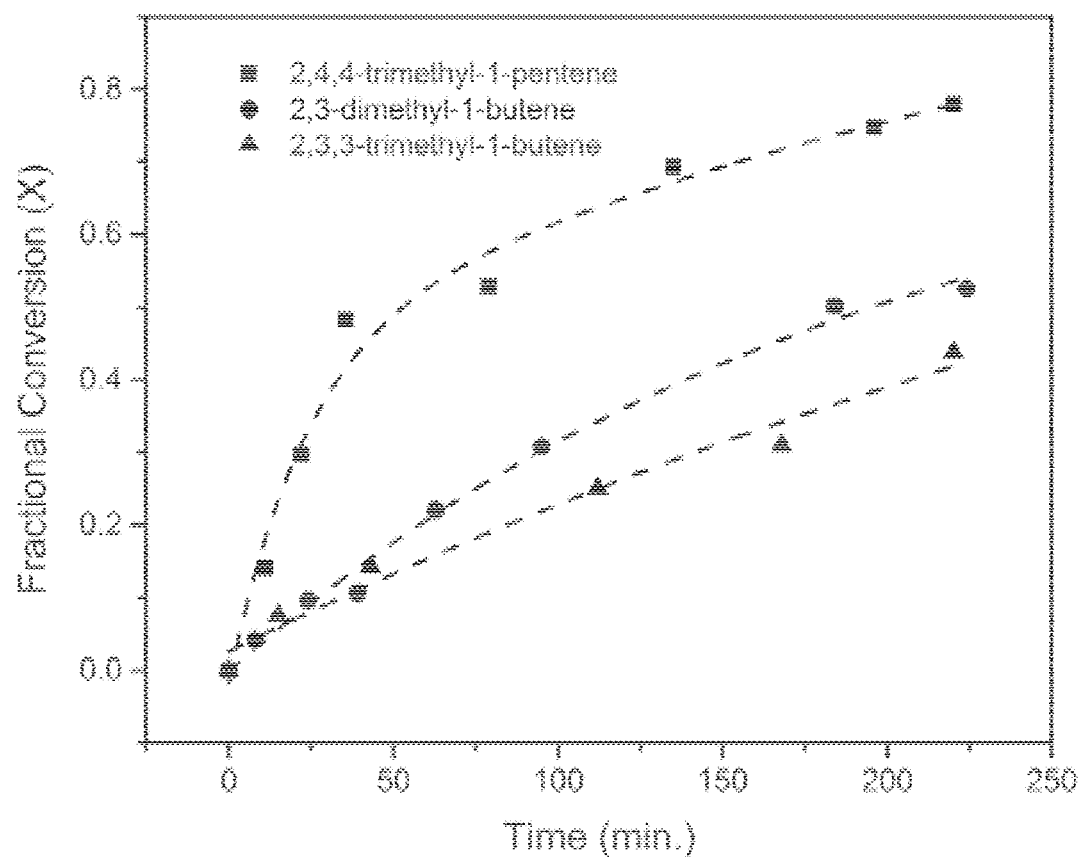
FIG. 27 illustrates the change in conversion of different olefins versus time at a reaction temperature of 100° C., according to exemplary embodiments of the present invention.

Example 3: $C_4$-$C_9$ Linear and Branched Olefin and Paraffin Fuel Conversion to Distillate-Range Hydrocarbon Fuels—The Effect of Olefin Chain Length The reactivity and selectivity of each olefin during the coupling reaction over Amberlyst-35™ may differ, thus affecting the overall product composition and the resulting fuel properties. The coupling of three different olefins, 2,3-dimethyl-1-butene ($C_6H_{12}$), 2,3,3-trimethyl-1-butene ($C_7H_{14}$, triptene) and 2,4,4-trimethyl-1-pentene ($C_8H_{16}$), were compared. FIG. 27 shows the conversion-time profiles for all the three olefins. The conversion-time profiles shown in FIG. 27 suggest that the 2,4,4-trimethyl-1-pentene and 2,3-dimethyl-1-butene are more reactive. However, it was found that the reactions of these two olefins demonstrated much lower coupling selectivity. Both of these olefins rapidly converted to less reactive isomers, for which the dimerization was slower than the parent α-olefin.

Figure 28:
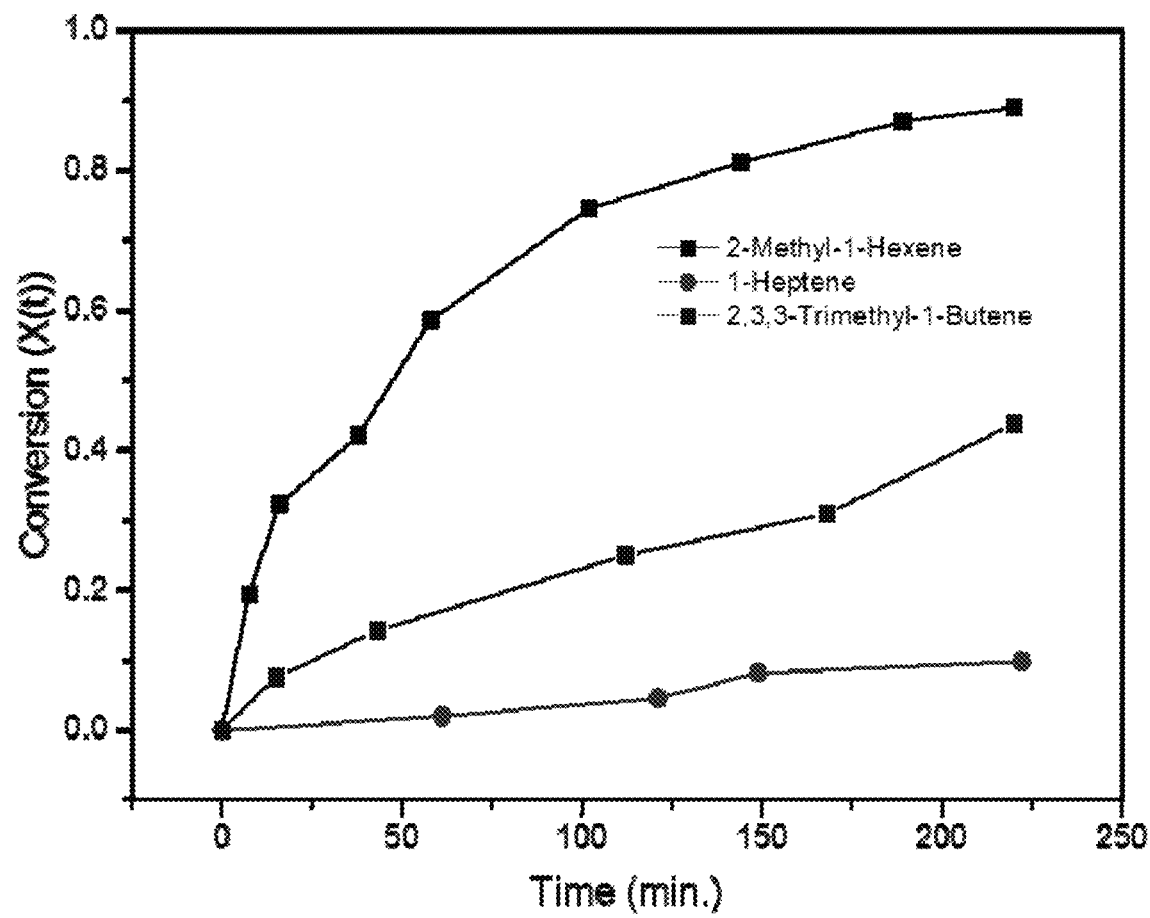
FIG. 28 compares the reactivity of olefins with different skeletal structures at a reaction temperature of 100° C. to produce higher molecular weight mixtures, according to exemplary embodiments of the present invention.
Figure 29:
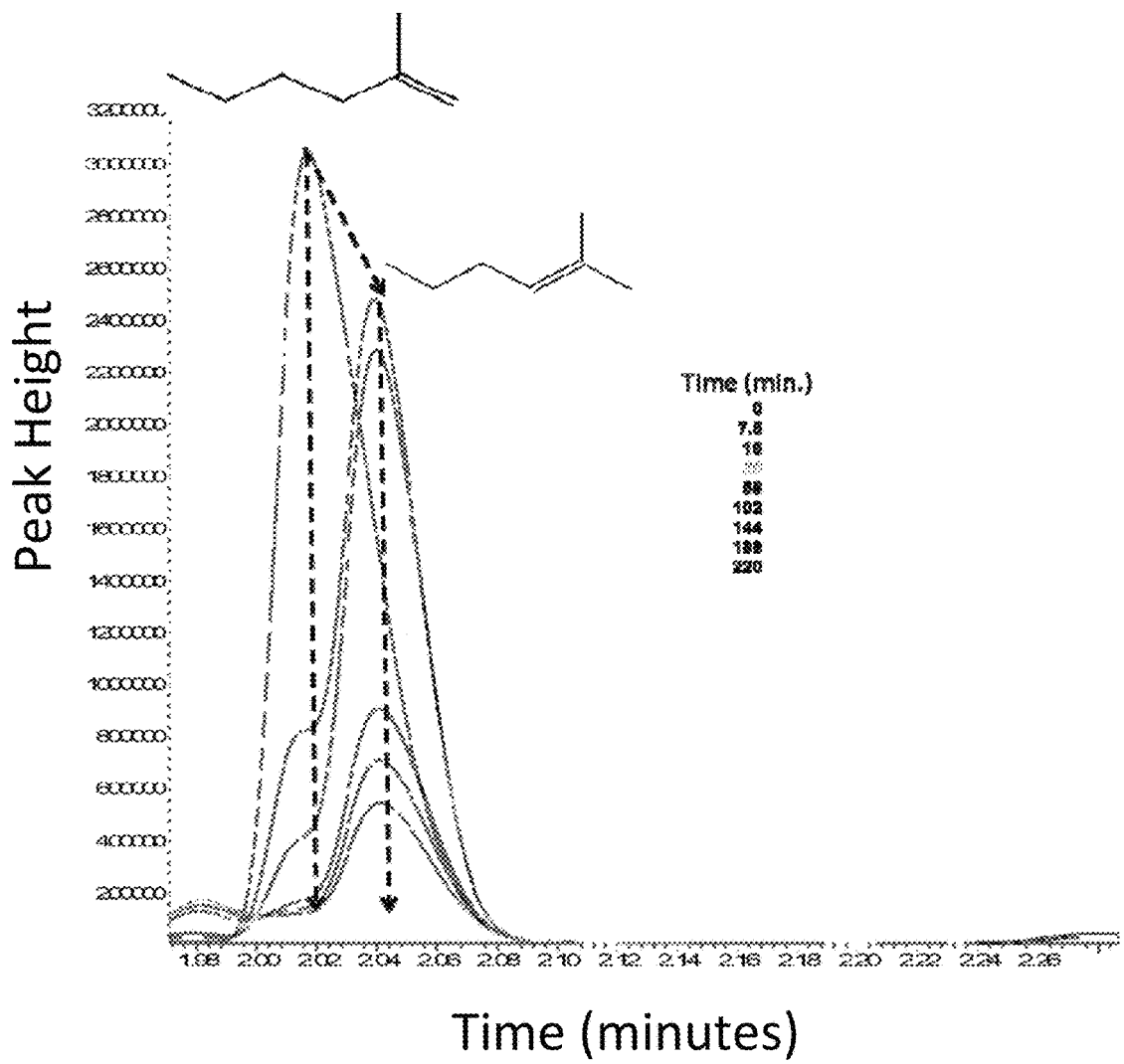
FIG. 29 illustrates experimental data obtained, according to exemplary embodiments of the present invention, from an flame ionization detector (FID) showing peaks at different times corresponding to 2-methyl-1-hexene and 2-methyl-2-hexene. 2-methyl-1-hexene isomerizes very rapidly to 2-methyl-2-hexene. Both the molecules continue to crack and couple over Amberlyst-35™.

Example 3: $C_4$-$C_9$ Linear and Branched Olefin and Paraffin Fuel Conversion to Distillate-Range Hydrocarbon Fuels—The Effect of Olefin Branching In order to compare the coupling of 2,3,3-trimethyl-1-butene (triptene) with that of less branched $C_7$ olefins, coupling reactivities of two additional reagents, namely 1-heptene and 2-methyl-1-hexene, were examined. All these olefins have a terminal double bond position (α-olefins). FIG. 28 compares the conversion-time profiles of these three olefins. All the other reaction variables were kept constant. 1-heptene was the least reactive for dimerization over Amberlyst-35™. This observation may be explained by the fact that the reaction intermediate, which is a primary or secondary carbenium ion, may be less stable and more difficult to form compared to the tertiary carbenium ion, which is formed in the case of 2-methyl-1hexene and triptene. The higher conversion of 2-methyl-1-hexene with respect to triptene may be attributed to the fact that the carbocation intermediate has to add to another parent olefin molecule. Since a triptene molecule provides larger steric hindrance to addition reactions than a 2-methyl-1-hexene molecule, the reactivity is higher for 2-methyl-1-hexene. In the case of 2-methyl-1-hexene, isomerization did occur, but the isomer disappeared quickly, as shown in FIG. 29. However, the desired coupled product and intermediate $C_8$-$C_{12}$ products did not appear to form or were formed at very low rates. This finding suggests a possibility that, compared to other olefins, pre-coupling cracking may be much more predominant in 2-methyl-1-hexene and consequently, the selectivity for the dimers was much smaller.

Example 3: $C_4$-$C_9$ Linear and Branched Olefin and Paraffin Fuel Conversion to Distillate-Range Hydrocarbon Fuels—Product Properties Relevant to Fuel-Specific Applications Gas chromatographic based distillation, 13C NMR and GC-MS analysis were used to assess the chemical composition and the physical characteristics of the final product. Fuel performance properties that were examined included boiling range distribution, heat of combustion, carbon-number distribution, and cloud point. The product used for this analysis was obtained after the completion of a long batch reaction with duration of greater than about 780 minutes. The results are compared herein with existing jet/diesel fuels. The results confirm that some properties of the resultant coupled product may be suited for applications as transportation fuel.

The cloud point measurements indicate that freezing does not occur above −47° C., as required for Jet-A grade fuel. The cloud points of the products, as measured using ASTM D5773, varied from −75° C. to −55° C. for the mixed olefin product. For both products, DSC analysis (with a slower cooling rate) indicated a glass transition temperature at −48° C., but freezing did not occur down to −80° C. A low freeze point is critical for jet applications given the low ambient temperatures at high altitude.

The higher and lower heating values, as measured per ASTM D240, were 45.8 MJ/kg and 42.8 MJ/kg respectively for the product from triptene, and 45.6 and 42.6 MJ/kg respectively for the product obtained from mixed olefin feed. Table 4 below compares the properties of the product mixture obtained from this invention with that of Jet A, a commercial jet fuel.

TABLE 4

Physical Property Comparison

| | | As-measured values | |
|---|---|---|---|
| Fuel properties | Known values for typical fuels Commercial fuels | Synthetic fuel from triptene | Synthetic fuel from mixed olefin feed |
| Cloud point (° C.) | −48 (Jet-A) | −75 | −55 |
| Lower heating value (LHV) (MJ/kg) | 42.8 (Jet-A) | 42.8 | 42.6 |
| Boiling point range (° C.) | Diesel(#2) Jet-A | | |
| IBP | 180 ~160 | 204 | 193 |
| T10 | 211 180 | 220 | 209 |
| T90 | 315 251 | 329 | 327 |

TABLE 4-continued

Physical Property Comparison

| Fuel properties | Known values for typical fuels Commercial fuels | | Synthetic fuel from triptene | Synthetic fuel from mixed olefin feed |
|---|---|---|---|---|
| FBP | 350 | 274 | 369 | 391 |
| Flash point (° C.) | 52 | 38 | 62.9‡ | |
| Density (g/mL) | 0.775-0.840 | | >0.78 | |

‡(for pure di-triptene $C_{14}H_{28}$)

The boiling ranges of the final products are shown in FIG. 36 and listed in Table 4. The boiling points of the product mixtures from coupling of gasoline-range feeds varied from approximately 200° C. to 400° C. Approximately 80% of the coupled product from both feeds is potentially useful for blending with jet fuel. Approximately 95% of the total product is potentially blendable with diesel. Higher boiling fractions are potentially suitable for heating oil and lubricant applications.

Figure 30A:
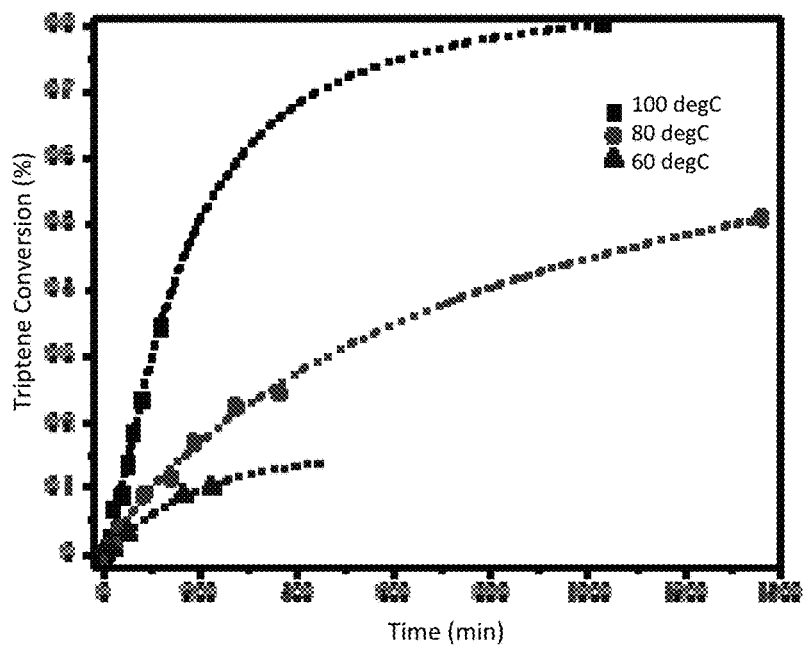
FIG. 30a-b illustrate a) triptene conversion (X) and b) corresponding dimer yield (Y) at three different temperatures with nonane as solvent, according to exemplary embodiments of the present invention.

FIG. 30a compares the conversion of triptene at three different temperatures with nonane as the solvent. As expected, at any given time, the extent of triptene consumption was larger at higher temperatures. The final conversions, as measured at 60, 80 and 100° C. (at different total reaction times), were approximately 18%, 51% and 80%, respectively.

Figure 30B:
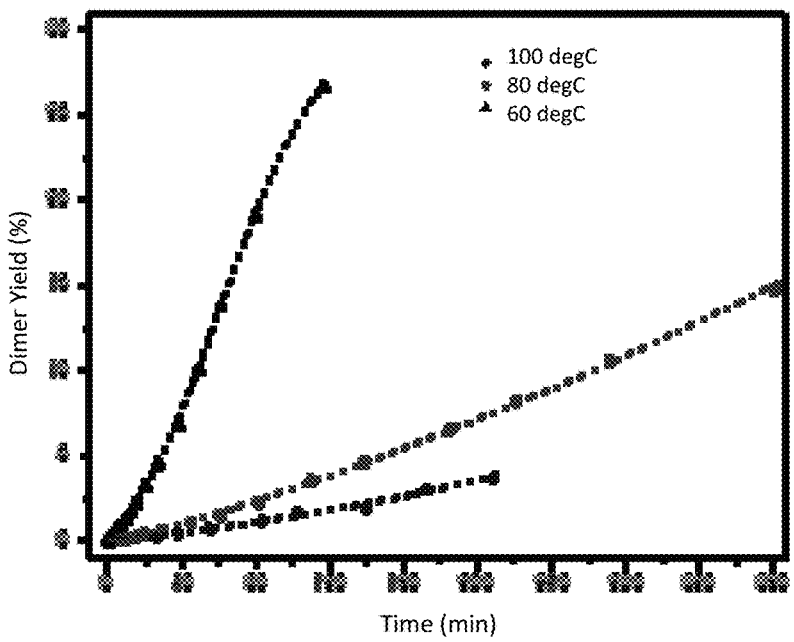

FIG. 30b is a plot of the dimer (di-triptene) yield versus time, corresponding to the three different temperatures. As expected, the conversion of triptene to dimers increased with temperature. At about 100° C., the dimer yield increased rapidly and reached a value of about 26.6% within the first 2 hours of the reaction. In comparison, the yields achieved during the same time at 80° C. and 60° C. were only about 4.2% and about 1.7%, respectively. The highest total distillate product yield of approximately 50% was achieved at 80° C.

Figure 31:
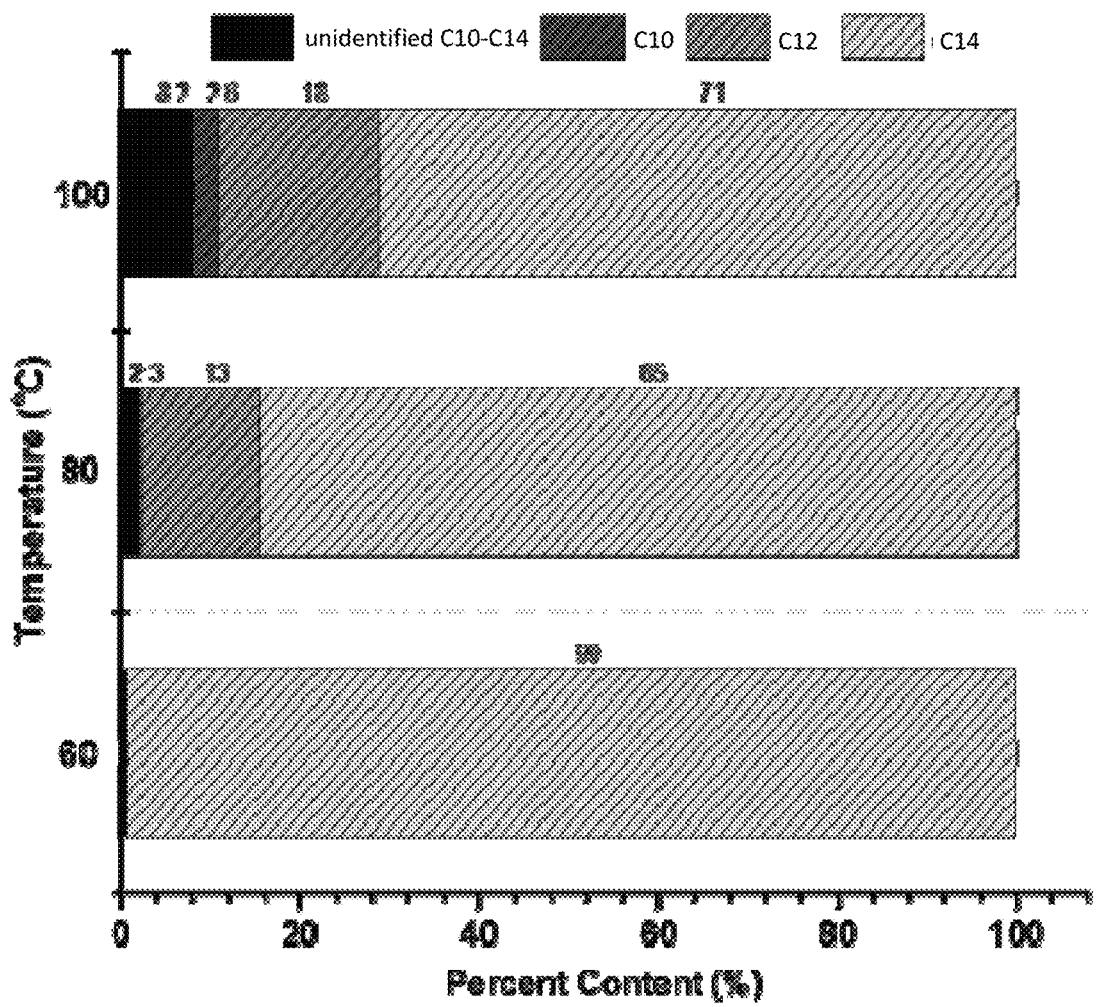
FIG. 31 illustrates the effect of temperature on product composition from triptene coupling after a fixed reaction duration (~2 h), according to exemplary embodiments of the present invention.

FIG. 31 compares the percent content of the products for different temperatures as analyzed after a fixed reaction time (about 2 hours). Although the conversion of triptene to dimer increased with increasing temperature, the production of cracked side products also increased at higher temperatures and consequently, the selectivity towards stoichiometric dimer product decreased. The selectivity towards dimers was higher at lower temperatures (maximum >90% at 60° C.) at the expense of lower reaction rates. During the first 2 hours of the reaction, the best case scenario was achieved at 100° C. with nonane as the solvent. This resulted in the production of the desired coupled hydrocarbon product (2,2,3,5,5,6,6-heptamethyl-3-heptene or di-triptene) with a conversion of approximately 35% and a selectivity of about 75%.

Figure 32:
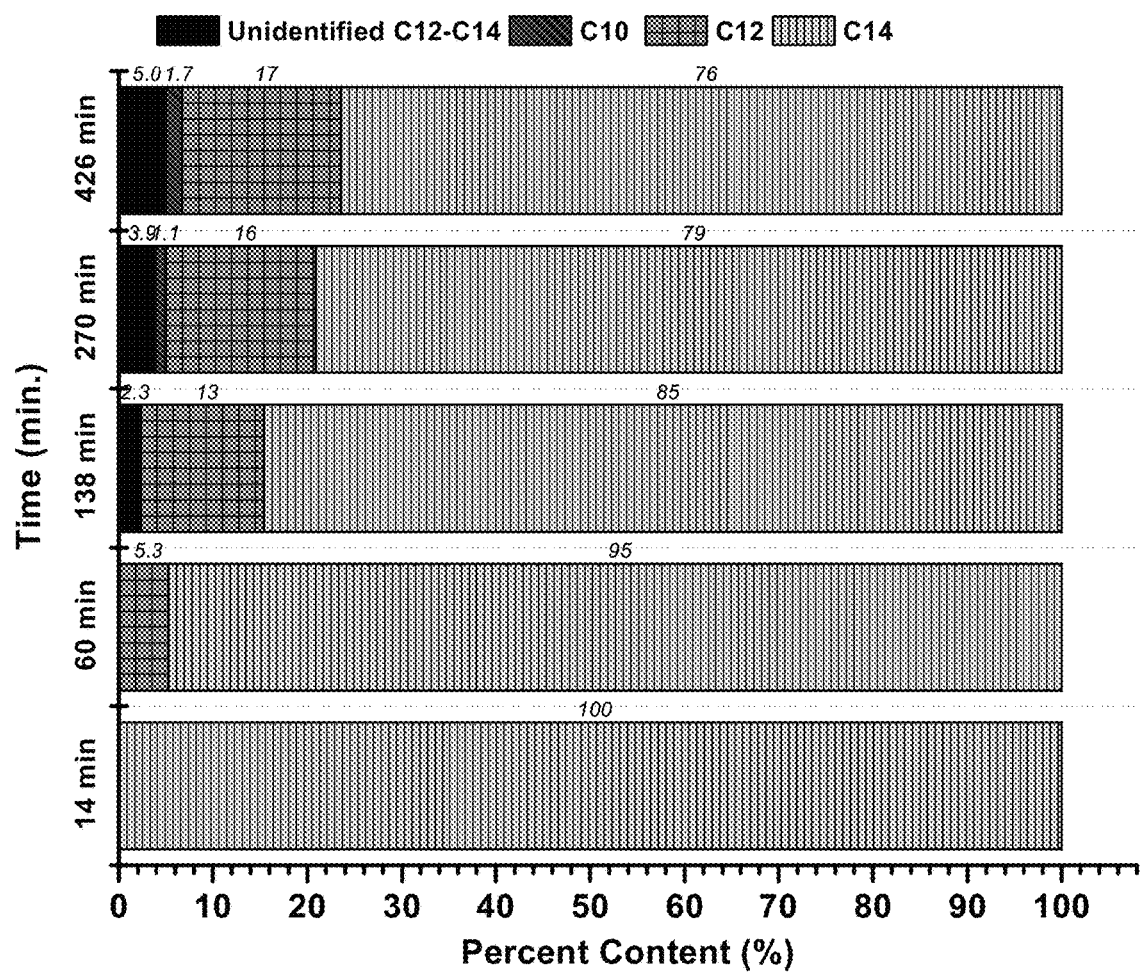
FIG. 32 illustrates the effect of reaction duration on the product composition from triptene coupling at 80° C. with nonane as solvent, according to exemplary embodiments of the present invention.

However, for 100° C., in the later stages of the reaction run, the selectivity and resultant dimer yield started to decrease with time. On the other hand, the yield for the reaction run at 80° C. continued to increase gradually. After about 16 hours, the dimer yield at 80° C. was about 46.6%. This suggests that at higher reaction temperatures, the coupled product forms quickly but may also be more susceptible to being converted into side products, possibly via the process of thermal cracking. The loss of selectivity was comparatively much slower at 80° C. (see FIG. 32). After about 7 hours, the selectivity for dimers gradually decreased to around 76% of reaction where the conversion was about 27%. As expected, rate of formation of cracked products was less severe at lower temperatures.

Based on these results, it appears that the selection of a temperature to maximize the coupled product yield depends upon the duration for which the reaction would be run. If the reaction is for short durations, for example, less than 4 hours, a higher coupled product yield may be expected when operating at higher temperatures. Alternatively, when operating for longer durations, higher yields for the coupling reactions can be achieved at 80° C., or lower than 100° C.

Figure 33:
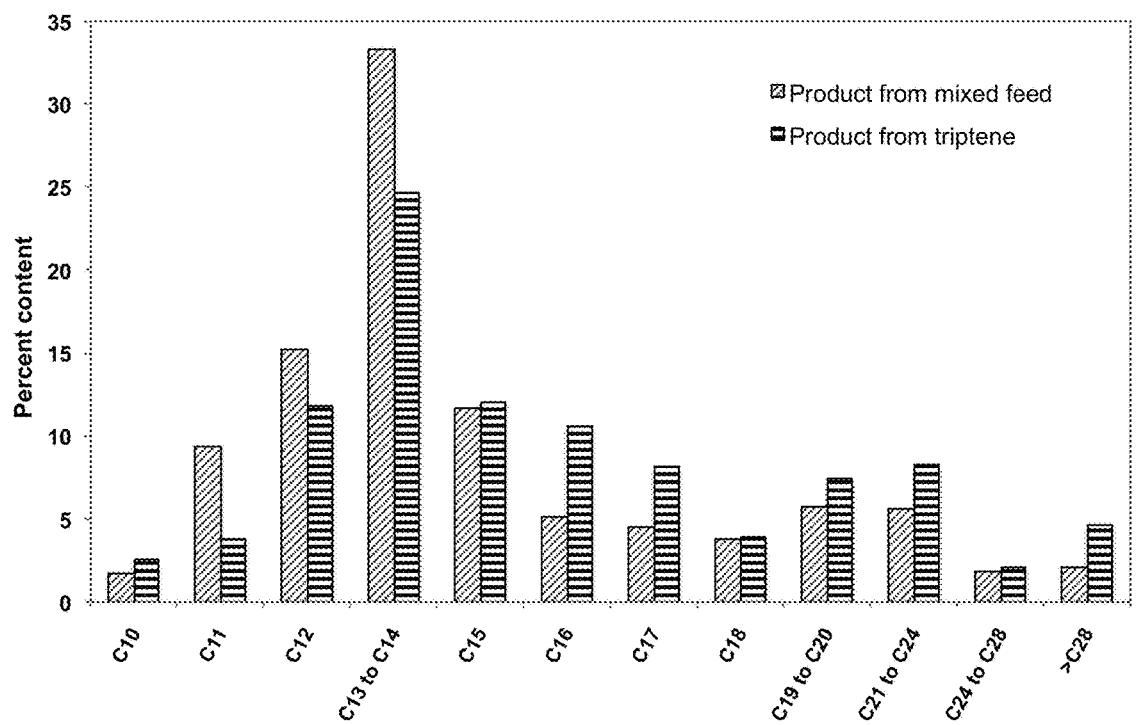
FIG. 33 illustrates the relative amounts of different carbon chain lengths present in the product (reaction was carried out with triptene or a mixture of $C_6$-$C_8$ olefins in nonane at 100° C. for 780 minutes), according to exemplary embodiments of the present invention.

Typically, during the initial several hours of reaction (~4 hours), no trimers or heavier products were observed. Most of the side products obtained were in the $C_{10}$-$C_{12}$ range and were highly branched (such as 2,2,3,5,6-pentamethyl-3-heptene; 2,3-dimethyl-3-octene etc.). Due to the mild conditions employed during the reaction, thermal cracking was minimal and products smaller than $C_{10}$ were absent or were present in relatively small amounts, which is unlike most other solid-acid catalysts, which may cause severe cracking because most of their catalytic activity is accessible mainly at higher reaction temperatures, which tends to promote thermal cracking. Although the extent of cracking was smaller here, the amount of side products, particularly oligomers, present in the product mixture increased with time. The side products obtained after long durations (~13 hours) showed a wider spread in carbon number ($C_{10}$-$C_{20+}$). Hydrocarbons heavier than $C_{20}$ contributed to approximately 15% of the FID signal area, as shown in FIG. 33. Such heavier hydrocarbons are likely a result of re-oligomerization of the cracked products from the main dimer.

Figure 34A:
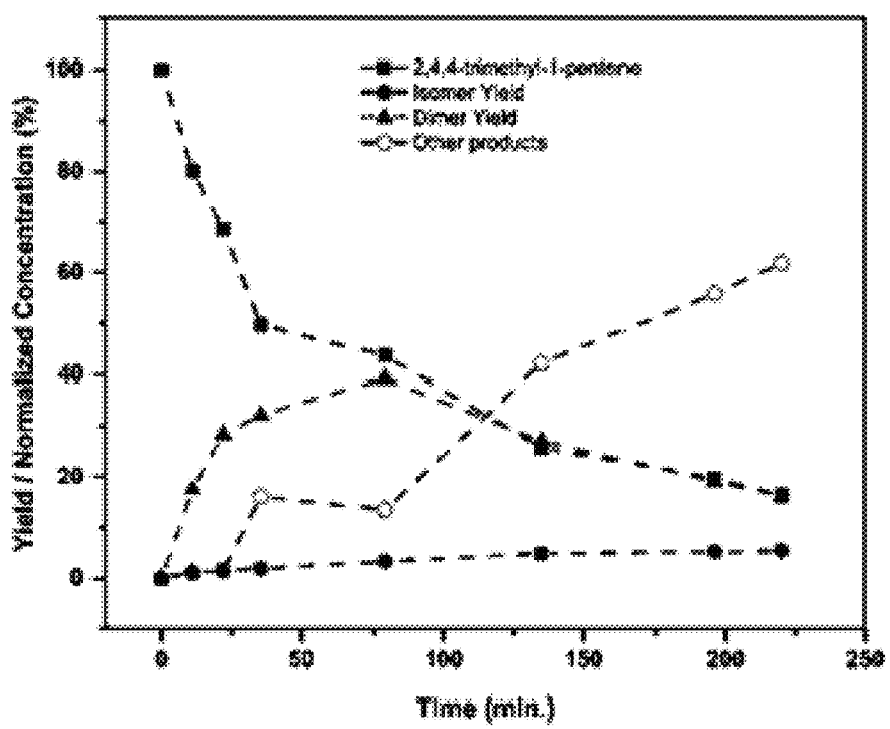
FIGS. 34a-c illustrate reactant concentrations and product yields resulting from conversion of a) 2,4,4-trimethyl-1-pentene, b) 2,3-dimethyl-1-butene and c) 2,3,3-trimethyl-1-butene (triptene) in pentadecane at 100° C., according to exemplary embodiments of the present invention
Figure 34B:
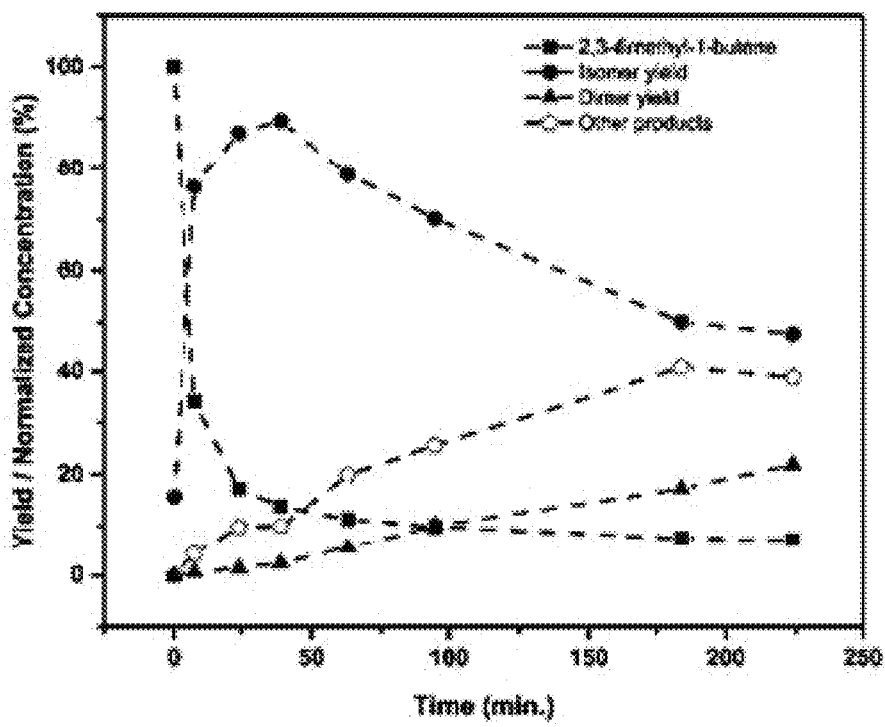
Figure 34C:
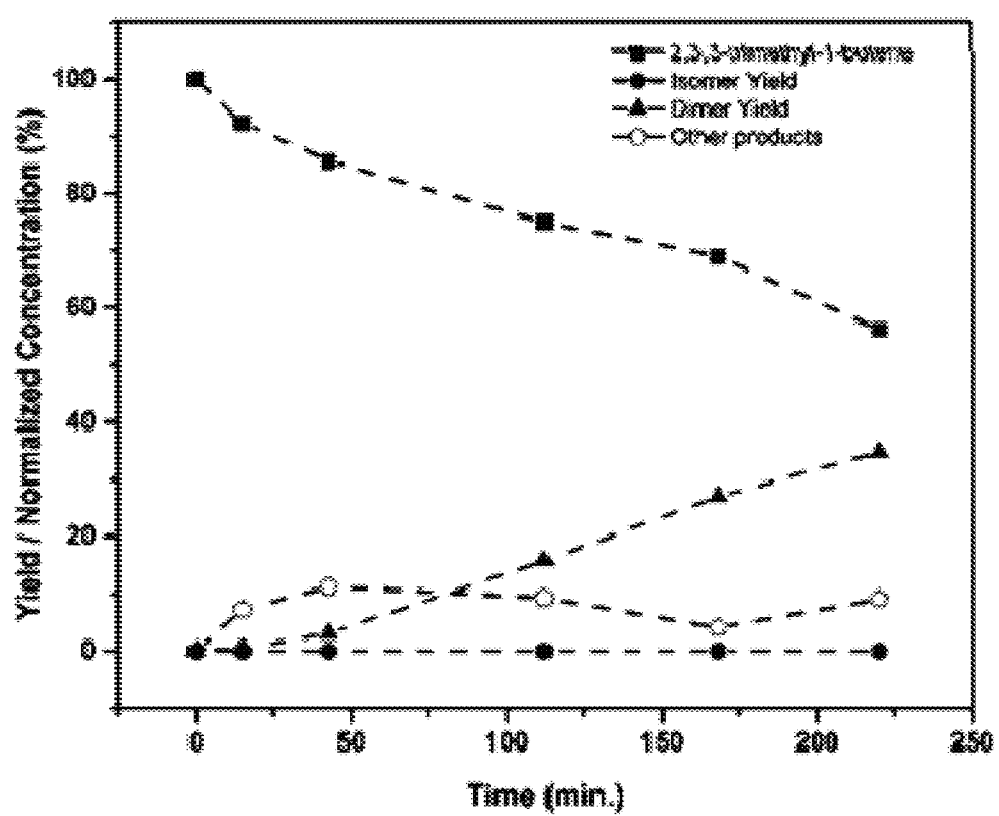

The performance of triptene coupling was compared with that of other $C_6$-$C_8$ olefins that have different skeletal structure, including 2,3-dimethyl-1-butene, 1-heptene and 2,4,4-trimethyl-1-pentene. The basis for selection of olefins was the similarity of these molecules, in terms of carbon number and branching, with the products from low-temperature acid-catalyzed DME homologation. In order to understand the role of branching and chain length of these olefins, the conversion of substrate and the corresponding dimer yield was examined. FIGS. 34a-c compare the conversion of the different olefins (100° C.). The rate of olefin disappearance provided an estimate of the overall reactivity of the corresponding olefin over the ion exchange resin. 2,4,4-trimethyl-1-pentene and 2,3-dimethyl-1-butene were overall more reactive, but larger fractions of these olefins were used in side reactions such as in isomerization and cracking reactions. Consequently, unlike the other olefins, the dimer yield for triptene increased continuously with increasing time.

In the case of 2,4,4-trimethyl-1-pentene, the dimer formation was fast initially but the resultant $C_{16}$ dimer showed high tendency to cracking, which explains the fast erosion of the dimer yield initiated within the first hour. Coupled products formed from the smaller olefins, triptene and 2,3-dimethy-1-pentene, presented much smaller amount of cracking. Comparison of the dimer yield and side products revealed that only in the case of triptene, neither cracking nor isomerization impeded the desired reaction and the di-triptene yield increased relatively unimpeded for longer times.

Figure 35:
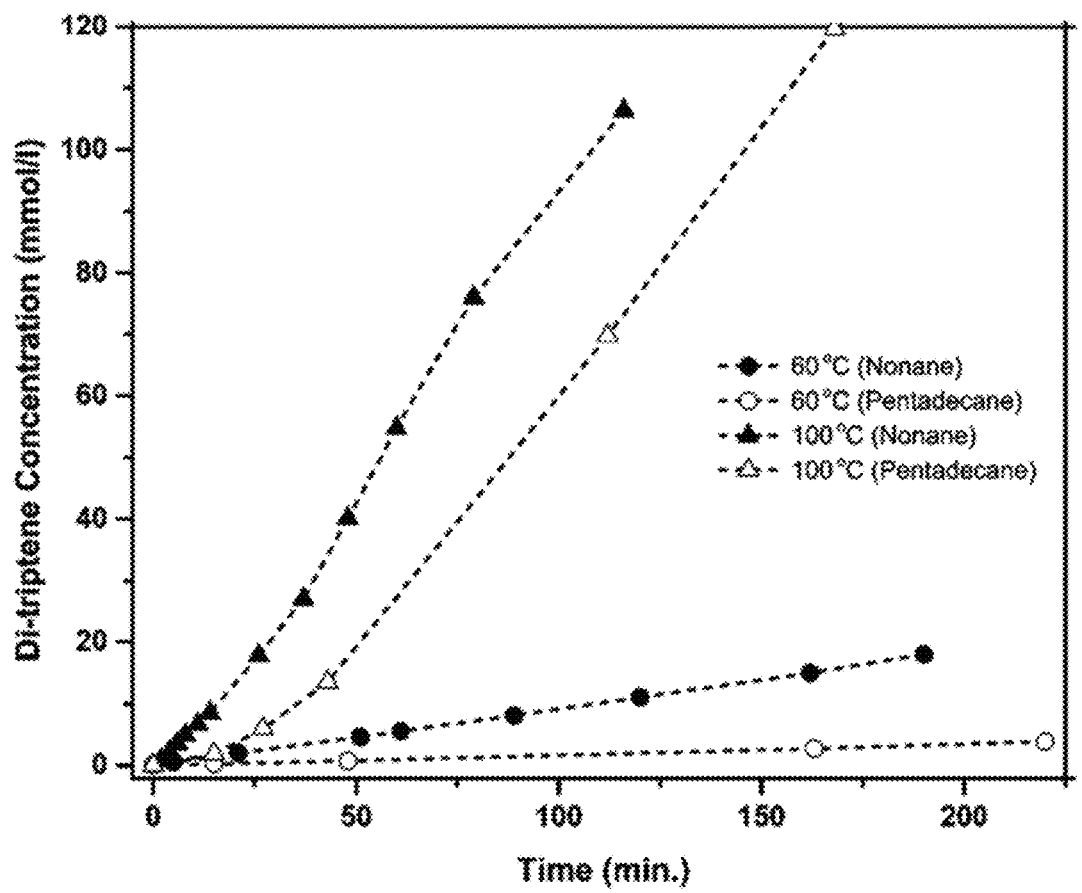
FIG. 35 illustrates the effect of solvent on triptene dimer production: di-triptene concentration with time for two different solvents at two different temperatures, according to exemplary embodiments of the present invention.
Figure 37:
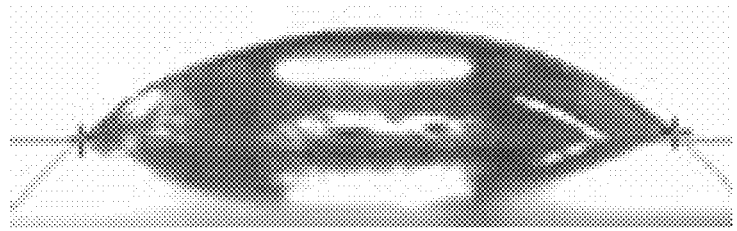
FIG. 37 illustrates the contact angles of pentadecane (Panel A) and nonane (Panel B) with a sulfonated surface similar to Amberlyst-35™ (Nafion-117 membrane).
Figure 37:
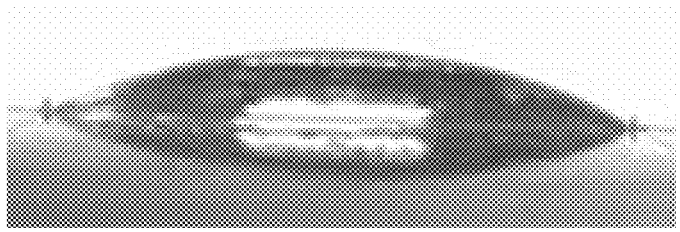

The solvent, in which the feed olefins were dissolved, also affected the selectivity and the overall conversion, with a lower molecular weight solvent yielding higher dimerization rates. FIG. 35 compares the production of ditriptene with time for two different solvents, nonane and pentadecane, at two different temperatures. For both temperatures, the initial dimerization rate was found to be higher in nonane. One of the possible causes for this could be the different wetting of the catalyst achieved by the different solvents. Table 5 compares the contact angle of nonane and pentadecane with a sulfonated surface similar to Amberlyst-35™ (Nafion-117 membrane). FIG. 37 shows photographs of the contact angles of pentadecane (Panel A) and nonane (Panel B) with a sulfonated surface similar to Amberlyst-35™ (Nafion-117 membrane). Clearly, the contact angle is much lower for nonane (25.5°) when compared to pentadecane (40°). This is probably due to the fact that the pentadecane is several orders of magnitude more hydrophobic than nonane whereas the —SO$_3$H-clad surface of Amberlyst-35™ is hydrophilic. Therefore, nonane may wet the surface more than pentadecane and as a result, nonane may transport the triptene molecule to the surface of the catalyst more effectively.

TABLE 5

Measurement of contact angle of the different solvents with a sulfonated surface

| Solvent | Pentadecane | Nonane |
|---|---|---|
| Contact angle (degrees) | 40.0° | 25.5° |

The dominant factor that influences the morphological properties of Amberlyst-type resins may be the polarity of the solvent. However, in the present case, both the solvents are sufficiently non-polar and were observed to cause equivalently minimal amount of swelling. Only in the polar reaction mixtures, the catalyst swelled to a greater extent and larger amount of active sites were freed from the internal network due to the higher disruption of the internal hydrogen bonding among the bound SO$_3$H groups. Hence, it is inferred that the difference in the wettability of Amberlyst-35™ in these two solvents is likely to be the primary cause for the observed activity differences and it is unlikely that differences in the observed activity for the two solvents are due to differences in the physical changes to the catalyst morphology.

ABSTRACT

Catalysts and processes designed to convert DME and/or methanol and hydrogen (H$_2$) to desirable liquid fuels are described. These catalysts produce the fuels efficiently and with a high selectivity and yield, and reduce the formation of aromatic hydrocarbons by incorporating H$_2$ into the products. Also described are process methods to further upgrade these fuels to higher molecular weight liquid fuel mixtures, which have physical properties comparable with current commercially used liquid fuels.

What is claimed is:

1. A liquid fuel comprising:
   2,2,3,5,5,6,6-heptamethyl-3-heptene, wherein:
   the liquid fuel has a density between 0.7 g/cm$^3$ and 0.85 g/cm$^3$;
   the liquid fuel has a boiling point between 180° C. and 400° C.;
   the liquid fuel has a heat of combustion between 40 MJ/kg and 50 MJ/kg; and
   the liquid fuel has a cloud point of less than −50° C.

2. The liquid fuel of claim 1, wherein the liquid fuel further comprises at least one of 2,2,4,6,6-pentamethyl-3-heptene, 2,2,3,5,6-pentamethyl-3-heptene, 2,3,5,5,6-pentamethyl-3-heptene, 2,2-dimethyl-3-octene, or 2,2,4,6,6,8,8-heptamethyl-4-nonene.

* * * * *